United States Patent
Tan et al.

(10) Patent No.: US 11,360,080 B2
(45) Date of Patent: Jun. 14, 2022

(54) AHR-ROR-γT COMPLEX AS A BIOMARKER AND THERAPEUTIC TARGET FOR AUTOIMMUNE DISEASE AND IL-17A-ASSOCIATED DISEASE

(71) Applicant: NATIONAL HEALTH RESEARCH INSTITUTES, Miaoli County (TW)

(72) Inventors: Tse-Hua Tan, Irvine, CA (US); Huai-Chia Chuang, Miaoli County (TW)

(73) Assignee: NATIONAL HEALTH RESEARCH INSTITUTES, Miaoli County (TW)

(*) Notice: Subject to any disclaimer, the term of this patent is extended or adjusted under 35 U.S.C. 154(b) by 499 days.

(21) Appl. No.: 16/541,851

(22) Filed: Aug. 15, 2019

(65) Prior Publication Data

US 2020/0057047 A1    Feb. 20, 2020

Related U.S. Application Data

(60) Provisional application No. 62/719,416, filed on Aug. 17, 2018.

(51) Int. Cl.
*G01N 33/50* (2006.01)
*C12N 5/0783* (2010.01)
(Continued)

(52) U.S. Cl.
CPC ....... *G01N 33/505* (2013.01); *A61K 48/0066* (2013.01); *C07K 16/2803* (2013.01);
(Continued)

(58) Field of Classification Search
CPC ............. G01N 33/505; G01N 33/5023; G01N 33/5041; G01N 33/53; G01N 33/541; G01N 33/6875; G01N 2333/70567; G01N 33/6872; G01N 2500/10; G01N 2500/00; A61K 48/0066; A61K 31/155; A61K 31/409; C07K 16/2803; C07K 16/44;
(Continued)

(56) References Cited

U.S. PATENT DOCUMENTS

| | | | |
|---|---|---|---|
| 2012/0244543 A1* | 9/2012 | Manel | C12N 5/0636 435/7.1 |
| 2020/0057047 A1* | 2/2020 | Tan | G01N 33/541 |

* cited by examiner

*Primary Examiner* — Jennifer Wecker
*Assistant Examiner* — Michael Paul Shimek
(74) *Attorney, Agent, or Firm* — Hsiu-Ming Saunders; Intellectual Property Connections, Inc.

(57) ABSTRACT

A method for identifying an AhR-phospho-RORγt protein complex inhibitor, comprising: (a) providing a cell culture, in which cells in the culture express AhR protein and phospho-RORγt protein; (b) incubating the cell culture in the presence of a test agent; (c) assaying the level of the AhR-phospho-RORγt protein complex in the presence of the test agent; (d) comparing the level of the AhR-phospho-RORγt protein complex in the presence of the test agent with a control; and (e) identifying the test agent as the inhibitor of the AhR-phospho-RORγt protein complex when the comparing step indicates that there is a reduction in the level of the AhR-phospho-RORγt protein complex in the presence of the test agent as compared with the control. A method for identifying a GLK–IQGAP1 protein complex inhibitor is also disclosed. Use of identified inhibitors in the manufacture of a medicament for treating a disease is also disclosed.

20 Claims, 21 Drawing Sheets

Specification includes a Sequence Listing.

(51) Int. Cl.
    *G01N 33/541*     (2006.01)
    *C07K 16/28*     (2006.01)
    *G01N 33/68*     (2006.01)
    *A61K 48/00*     (2006.01)
    *G01N 33/53*     (2006.01)

(52) U.S. Cl.
    CPC ....... *C12N 5/0636* (2013.01); *G01N 33/5023* (2013.01); *G01N 33/5041* (2013.01); *G01N 33/53* (2013.01); *G01N 33/541* (2013.01); *G01N 33/6875* (2013.01); *G01N 2333/70567* (2013.01)

(58) Field of Classification Search
    CPC .... C07K 2317/34; C07K 16/28; C07K 16/40; C12N 5/0636; A01K 2217/05; A01K 2217/075; A01K 2227/105; A61P 35/00
    See application file for complete search history.

US 11,360,080 B2

AHR-ROR-γT COMPLEX AS A BIOMARKER AND THERAPEUTIC TARGET FOR AUTOIMMUNE DISEASE AND IL-17A-ASSOCIATED DISEASE

REFERENCE TO RELATED APPLICATION

The present application claims tike priority to U.S. Provisional Application Ser. No. 62/719,416, filed Aug. 17, 2018, which is herein incorporated by reference in its entirety.

FIELD OF THE INVENTION

The present invention relates generally to autoimmune disease, and more specifically to GLK-induced AhR-ROR gamma T complex as a therapeutic target for IL-17 production and IL-17-mediated diseases.

BACKGROUND OF THE INVENTION

Autoimmune diseases arise from immune system overactivation. T helper 17 cells (Th17, IL-17A-producing CD4$^+$ T cells) and IL-17A play critical roles in the pathogenesis in autoimmune diseases. The transcription factor RORγt binds to IL-17A promoter and controls IL-17A gene transcription. Aryl hydrocarbon receptor (AhR) promotes Th17 polarization through inducing IL-17A transcription and inhibiting the negative regulator STAT1 during Th17 differentiation. T-cell-specific AhR knockout mice have impaired Th17 differentiation and are resistant to Th17-mediated experimental autoimmune arthritis. Various pathogenic Th17 subpopulations can be derived in vitro under different conditions. The in vivo roles of these distinct Th17 subpopulations in the pathogenesis of autoimmune diseases remain unclear.

MAP4K3 (also named GLK) is a mammalian Ste20-like serine/threonine kinase. Clinical samples from patients with autoimmune diseases such as systemic lupus erythematosus (SLE), rheumatoid arthritis (RA) or adult-onset Still's disease (AOSD) show dramatically increased GLK expression in T cells. However, it remains unclear how GLK overexpression contributes to multiple human autoimmune diseases.

SUMMARY OF THE INVENTION

In one aspect, the invention relates to a method for identifying an inhibitor of AhR-phospho-RORγt protein complex, comprising: (a) providing a cell culture, in which cells in the culture express Aryl hydrocarbon Receptor (AhR) protein and phospho-Retinoic-acid-receptor-related orphan nuclear receptor gamma t (RORγt) protein; (b) incubating the cell culture in the presence of a test agent; (c) assaying the level of the AhR-phospho-RORγt protein complex in the presence of the test agent; (d) comparing the level of the AhR-phospho-RORγt protein complex in the presence of the test agent with a control; and (e) identifying the test agent as the inhibitor of the AhR-phospho-RORγt protein complex when the comparing step indicates that there is a reduction in the level of the AhR-phospho-RORγt protein complex in the presence of the test agent as compared with the control.

In one embodiment, the assaying step performs immunoblotting using an anti-phospho-RORγt [Ser489] antibody.

In another embodiment, the cells are selected from the group consisting of T cells of Lck-GLK transgenic mice, GLK-overexpressing T cells, TCR-activated T cells, and AhR+RORγt+IKKβ overexpressing cells.

In another embodiment, (i) the providing step provides cells that are co-transfected with CFP-AhR, YFP-RORγt, and IKKβ plasmids; (ii) the assaying step performs a fluorescence resonance energy transfer (FRET) assay; and (iii) the identifying step identifies the test agent as the inhibitor of the AhR-phospho-RORγt protein complex when the comparing step indicates that there is a reduction of fluorescence intensity emitted by the YFP-RORγt in the presence of the test agent as compared with the control.

In another embodiment, (i) the providing step provides cells that are co-transfected with an epitope tagged AhR, Myc-RORγt, and IKKβ plasmids; (ii) the assaying step is performed using ALPHA assay with anti-Myc antibody-conjugated acceptor beads and anti-epitope antibody-coated donor beads; and (iii) the identifying step identifies the test agent as the inhibitor of the AhR-phospho-RORγt protein complex when the comparing step indicates there is a reduction of signal emitted by the anti-Myc antibody-conjugated acceptor beads in the presence of the test agent as compared with the control; wherein the epitope consists of the sequence of SEQ ID NO: 1.

In another embodiment, (i) the providing step provides cells selected from the group consisting of T cells of Lck-GLK transgenic mice, GLK-overexpressing T cells, TCR-activated T cells and AhR+RORγt+IKKβ overexpressing cells; (ii) the assaying step performs an in situ proximity ligation assay (PLA) using anti-AhR antibody and anti-RORγt or anti-phospho-RORγt [Ser489] antibody as primary antibodies, secondary antibodies as PLA probes, and fluorescent-labeled complementary oligonucleotide probes for signal detection; and (iii) the identifying step identifies the test agent as the inhibitor of the AhR-phospho-RORγt protein complex when the comparing step indicates there is a fluorescence signal reduction in the presence of the test agent as compared with the control.

In another embodiment, (i) the providing step provides cells that are co-transfected with Myc-AhR, an epitope tagged RORγt, and IKKβ plasmids; (ii) the assaying step performs a co-immunoprecipitation assay by incubating cell extracts with anti-epitope agarose beads or anti-Myc agarose beads to precipitate the AhR-phospho-RORγt protein complex and immunoblotting the AhR-phospho-RORγt complex immunoprecipitated with an anti-Myc or an anti-epitope antibody; and (iii) the identifying step identifies the test agent as the inhibitor of the AhR-phospho-RORγt protein complex when the comparing result indicates there is a reduction of signal in the presence of the test agent as compared with the control; wherein the epitope consists of the sequence of SEQ ID NO: 1.

In another embodiment, (i) the providing step provides cells selected from the group consisting of T cells of Lck-GLK transgenic mice, GLK-overexpressing T cells, TCR-activated T cells and AhR+RORγt+IKKβ overexpressing cells; (ii) the assaying step performs a chromatin immunoprecipitation (ChIP)-DNA sequencing assay using an anti-RORγt antibody to immunoprecipitate the AhR-phospho-RORγt protein complex and performing a PCR using a pair of primers comprising an AhR-binding site nucleotide sequence in IL-17A promoter DNA sequence to obtain a PCR product; and (iii) the identifying step identifies the test agent as the inhibitor of the AhR-phospho-RORγt complex when the comparing step indicates there is a reduction in the quantity of the PCR product in the presence of the test agent as compared with the control.

In another aspect, the invention relates to a method for identifying an inhibitor of GLK–IQGAP1 protein complex, comprising: (a) providing a cell culture, in which cells in the culture express GLK protein and IQGAP1 protein; (b) incubating the cell culture in the presence of a test agent; (c) assaying the level of the GLK–IQGAP1 protein complex in the presence of the test agent; (d) comparing the level of the GLK–IQGAP1 protein complex in the presence of the test agent with a control; and (e) identifying the test agent as the inhibitor of the GLK–IQGAP1 protein complex when the comparing step indicates that there is a reduction in the level of the GLK–IQGAP1 protein complex in the presence of the test agent as compared with the control.

In one embodiment, (i) the providing step provides cells selected from the group consisting of GLK transgenic mice, GLK-overexpressing cells, and GLK+IQGAP1-overexpressing cells; (ii) the assaying step performs an in situ proximity ligation assay (PLA) using anti-IQGAP1 antibody and anti-GLK or anti-phospho-IQGAP1 [Ser480] antibody as primary antibodies, secondary antibodies as PLA probes, and fluorescent-labeled complementary oligonucleotide probes for signal detection; and (iii) the identifying step identifies the test agent as the inhibitor of the GLK–IQGAP1 protein complex when the comparing step indicates that there is a fluorescence signal reduction in the presence of the test agent as compared with the control. in another embodiment, the assaying step performs immunoblotting using an anti-phospho-IQGAP1 [Ser480] antibody.

Further in another aspect, the invention relates to a method for treating an IL-17A associated disease, comprising administering an effective amount of an AhR-phospho-RORγt protein complex inhibitor identified by the method of the invention to a subject in need thereof to treat the IL-17A associated disease in the subject in need thereof.

In one embodiment, the AhR-phospho-RORγt protein complex inhibitor is selected from the group consisting of verteporfin and alexidine dihydrochloride.

In another embodiment, the IL-17A associated disease is selected from the group consisting of an autoimmune disease, GLK-overexpressing cancer cell metastasis, and GLK-overexpressing cancer cell recurrence.

In another embodiment, the method of the invention treats the autoimmune disease in the subject in need thereof and the administering step administers the AhR-phospho-RORγt protein complex inhibitor verteporfin or alexidine dihydrochloride.

In another embodiment, the method of the invention treats GLK-overexpressing cancer cell metastasis in the subject in need thereof and the administering step administers the AhR-phospho-RORγt protein complex inhibitor verteporfin or alexidine dihydrochloride.

In another embodiment, the method of the invention treats GLK-overexpressing cancer cell metastasis in the subject in need thereof and the administering step administers the AhR-phospho-RORγt protein complex inhibitor verteporfin.

In another aspect, the invention relates to a method for treating GLK-overexpressing cancer cell metastasis, comprising administering an effective amount of an inhibitor of GLK–IQGAP1 protein complex identified by the method of the invention to a subject in need thereof to treat the GLK-overexpressing cancer cell metastasis in the subject in need thereof.

In one embodiment, the inhibitor of GLK–IQGAP1 protein complex is verteporfin or alexidine dihydrochloride.

In another embodiment, the method for treating GLK-overexpressing cancer cell metastasis comprises administering an effective amount of verteporfin to a subject in need thereof to treat the GLK-overexpressing cancer cell metastasis in the subject in need thereof.

Figure 8:
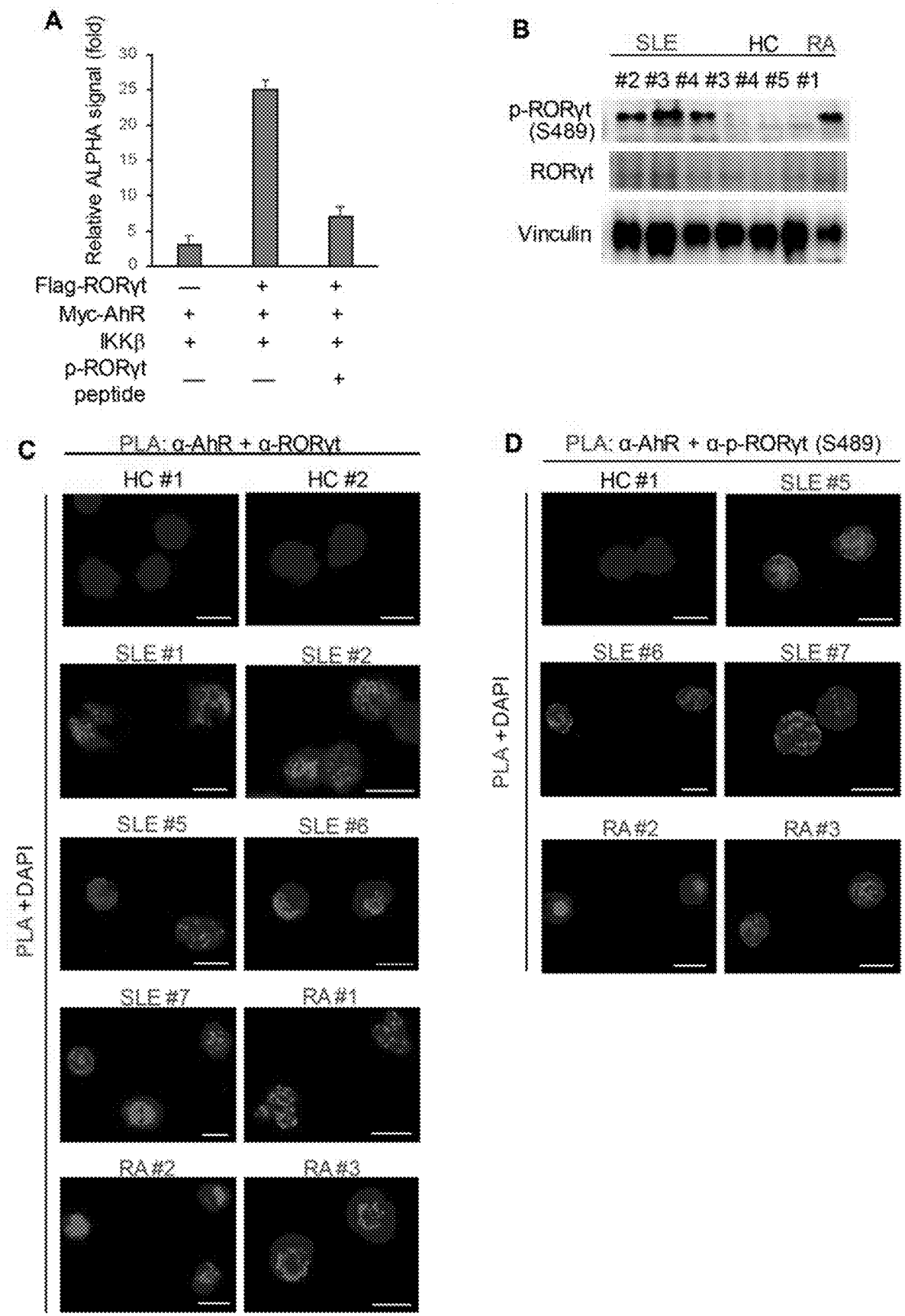

FIG. 8 shows that phosphorylated RORγt interacts with AhR in human autoimmune T cells. (A) Signals of the interaction (<200 nm) between Myc-AhR and Flag-RORγt in lysates of HEK293T cells determined by amplified luminescent proximity homogeneous assays (ALPHA). Means±SD are shown. p-RORγt peptide denotes S489-phosphorylated RORγt peptide, $^{482}$LFSTDVE{pS}PEGLSK$^{-495}$. (B) Immunoblotting of p-RORγt (Ser-489) and RORγt in peripheral blood T cells freshly isolated from 3 SLE patients, 1 RA patient, and 3 HC. (C) Confocal microscopy of PLA for the interaction between AhR and RORγt in peripheral blood T cells, which were freshly isolated from 5 SLE patients, 3 RA patients, and 2 healthy controls. (D) Confocal microscopy of PLA for the interaction between endogenous AhR and phosphorylated RORγt in peripheral blood T cells from 2 SLE patients, 2 RA patients, and 1 healthy control. SLE, systemic lupus erythematosus; RA, rheumatoid arthritis; HC, healthy control. Original magnification, ×630; bar, 10 μm.

Figure 9:
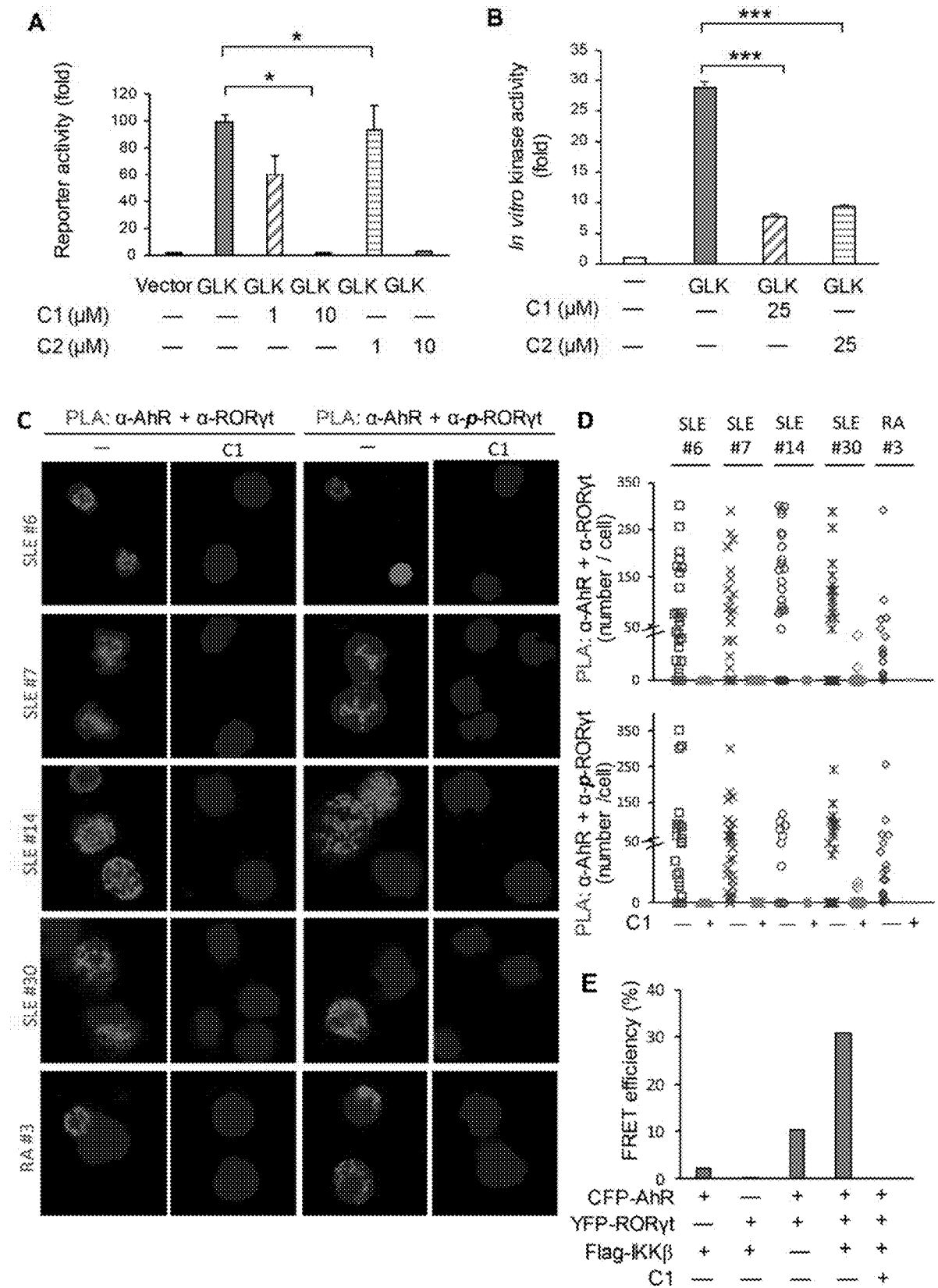

FIG. 9 shows that the GLK inhibitor C1 (verteporfin) blocks the AhR-RORγt complex. (A) Luciferase activity of NF-κB-driven reporter assays in stable GLK-transfected CHO-K1 cells that were treated with or without the GLK inhibitor C1 (verteporfin) under the indicated concentration. The fold changes are presented relative to the value of vector control. (B) Recombinant proteins of GLK kinase domain plus recombinant proteins of GST-tagged kinase-dead PKCθ (K409W) were subjected to in vitro kinase assays in the presence or absence of the GLK inhibitor C1 (verteporfin). Means±SD of are shown. *, P value<0.05; **, P value<0.01 (two-tailed Student's t-test). (C) The AhR-RORγt complex was inhibited by the GLK inhibitor. Confocal microscopy of proximity ligation assays (PLA) for the interaction between AhR and either RORγt or phospho-RORγt (S489) in peripheral blood T cells treated with C1 (verteporfin) (5 μM) for 30 min. The T cells were freshly isolated from 4 SLE patients and 1 RA patients. C1 denotes verteporfin; C2 denotes alexidine dihydrochloride. (D) Quantification of the PLA signals of (C). (E) FRET assays of HEK293T cells co-transfected with CFP-AhR, YFP-RORγt, and IKKβ plasmids.

Figure 10:
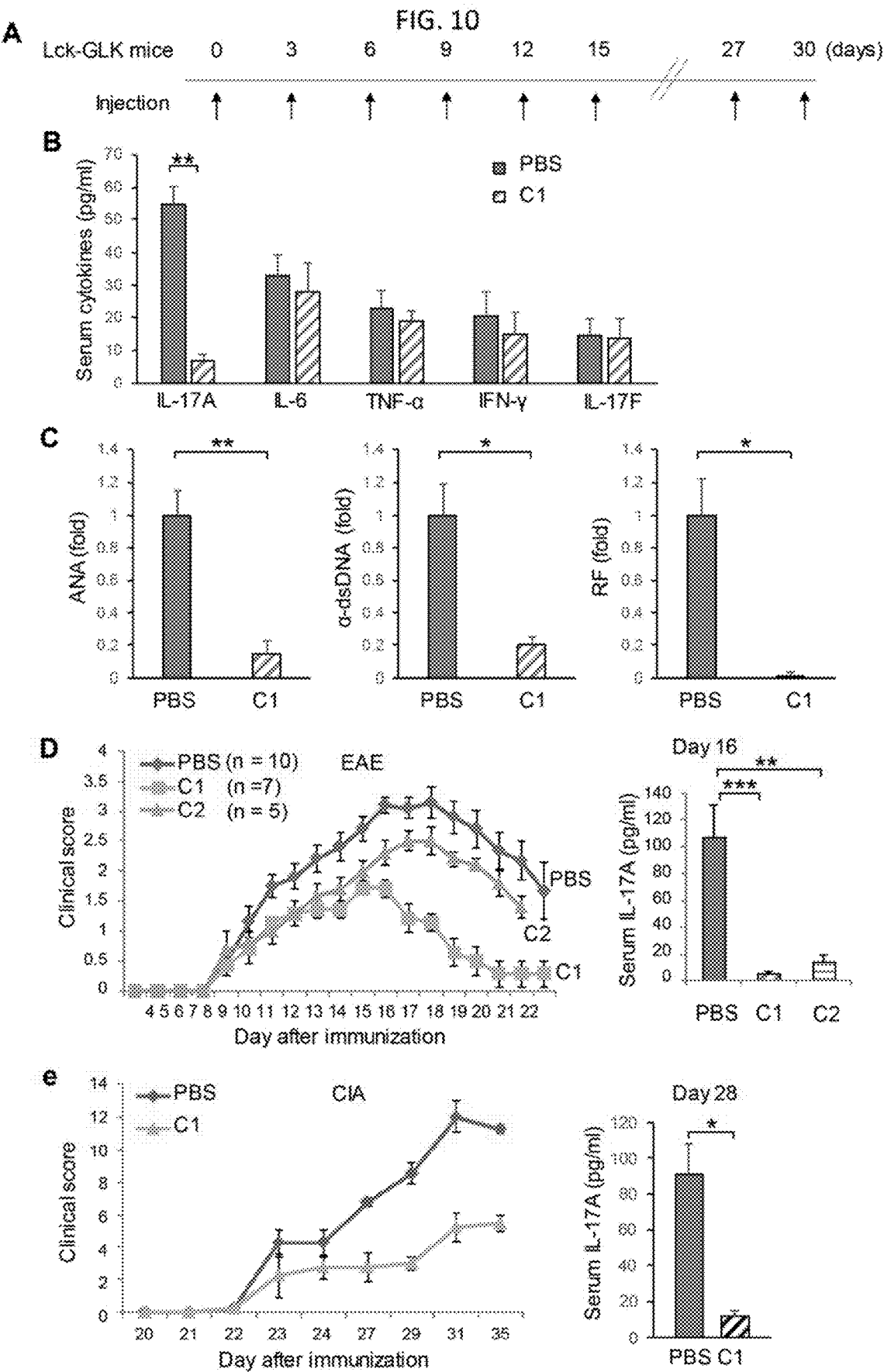

FIG. 10 shows that the inhibitors of GLK-induced AhR-RORγt complex suppress IL-17 production and autoimmune responses in mice. (A to C) Effect of the GLK inhibitor C1 (verteporfin) administration (0.556 nmole/g every 3 days for 30 days) on serum IL-17A and autoantibodies in Lck-GLK Tg mice. (B) ELISA of indicated serum cytokines in Lck-GLK Tg mice treated with C1 (verteporfin) or PBS. (C) ELISA of serum autoantibodies in Lck-GLK Tg mice treated with C1 (verteporfin) or PBS. Means±SEM are shown. (D) Experimental autoimmune encephalomyelitis (EAE) induction in wild-type mice treated with PBS, or the GLK inhibitor C1 (verteporfin) and C2. Clinical scores are presented on a scale of 1 to 5 (left panel). ELISA of IL-17A in the sera from MOG-immunized mice at day 16 (right panel). (E) Collagen-induced arthritis (CIA) induction in wild-type mice treated with the GLK inhibitor C1 (verteporfin) or PBS. Clinical scores are presented on a scale of 1 to 16 (left panel). ELISA of IL-17A in the sera from collagen-immunized mice at day 28. Means±SEM are shown. *, P value<0.05; , P value<0.01; *, P value<0.001 (two-tailed Student's west). C1 denotes verteporfin; C2 denotes alexidine dihydrochloride.

Figure 11:
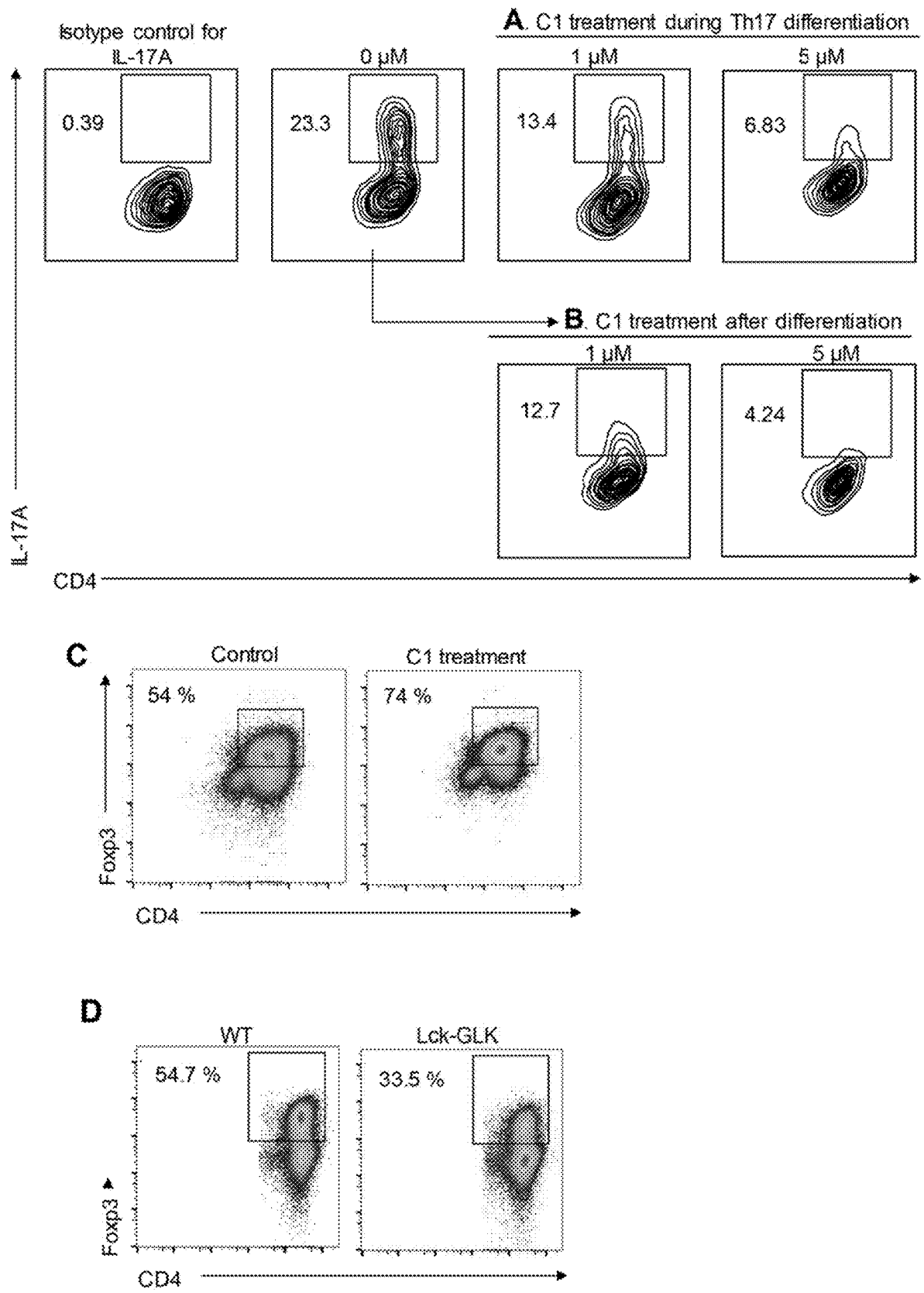

FIG. 11 shows that verteporfin inhibits Th17 differentiation but enhances Treg differentiation. (A) Flow cytometry of IL-17A-producing CD4$^+$ T cells. Splenic T cells were co-treated with verteporfin (C1) (1 or 5 μM) during Th17 differentiation in vitro. (B) Flow cytometry of IL-17A-producing CD4$^+$ T cells. Murine in vitro differentiated Th17 cells were stimulated with PMA plus ionomycin and co-treated with verteporfin (C1) (1 or 5 μM) for 30 min. (C) Flow cytometry of Foxp3-producing CD4$^+$ T cells. Splenic T cells were co-treated with verteporfin (C1) (5 μM) during Treg differentiation in vitro. (D) Flow cytometry of Foxp3-producing CD4$^+$ T cells, which were differentiated from CD4$^+$ T cells of wild-type or Lck-GLK transgenic mice.

Figure 12:
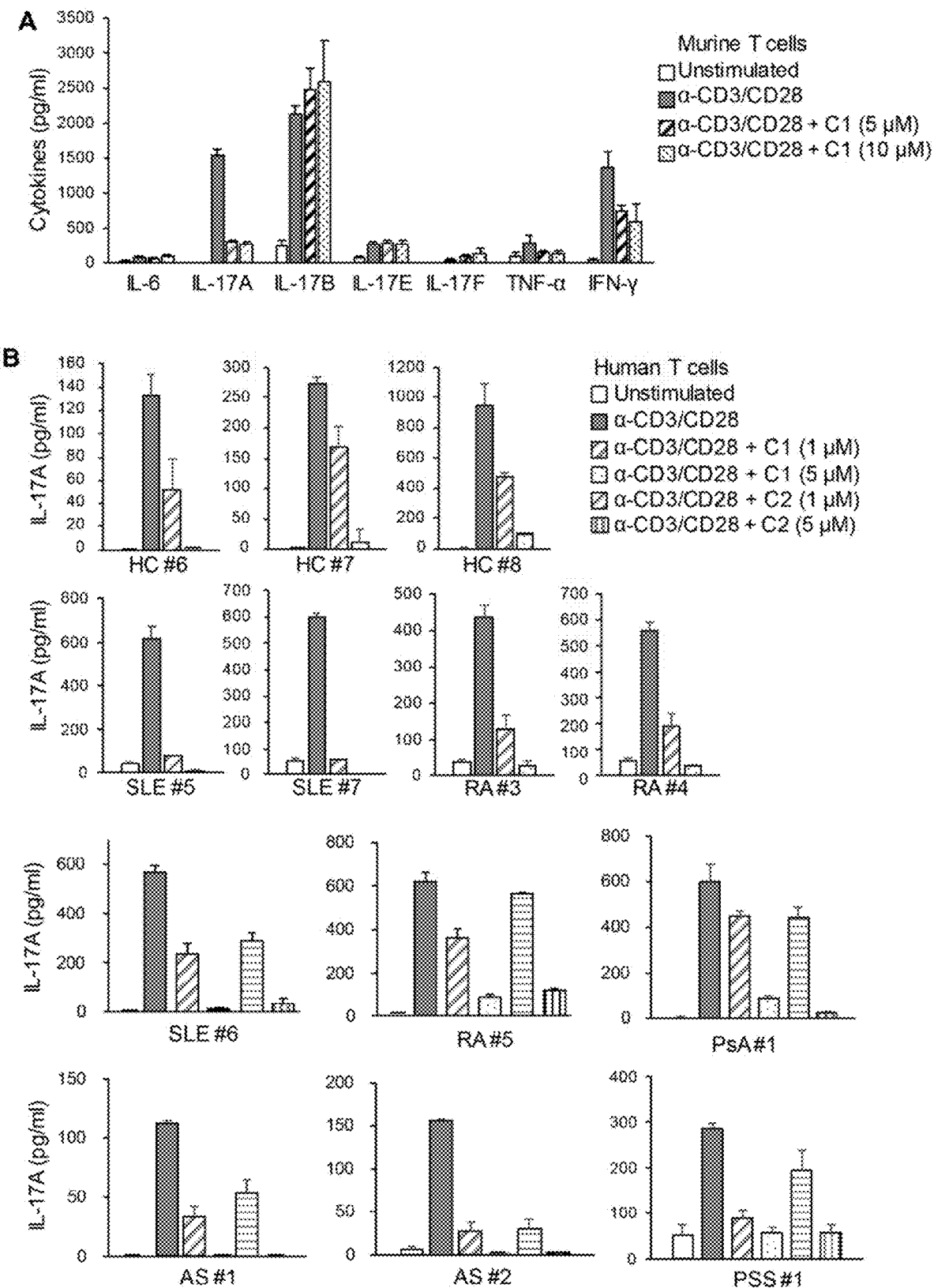

FIG. 12 shows that the inhibitors of GLK-induced AhR-RORγt complex block IL-17 production of human T cells, (a) ELISA of various cytokines in supernatants of murine primary T cells stimulated with anti-CD3/CD28 and treated with C1 (verteporfin) (5 μM or 10 μM) for 3 days. Means±SD are shown, (b) ELISA of IL-17A in supernatants of human T cells. T cells were stimulated with anti-CD3/CD28 and treated with C1 (verteporfin) (1 μM or 5 μM) or C2 (1 μM or 5 μM) for 3 days. HC, healthy control; SLE, systemic lupus erythematosus; RA, rheumatoid arthritis; AS, ankylosing spondylitis; PsA, psoriatic arthritis; PSS, primary Sjögren's syndrome. Means±SD are shown. C1 denotes verteporfin; C2 denotes alexidine dihydrochloride.

Figure 13:
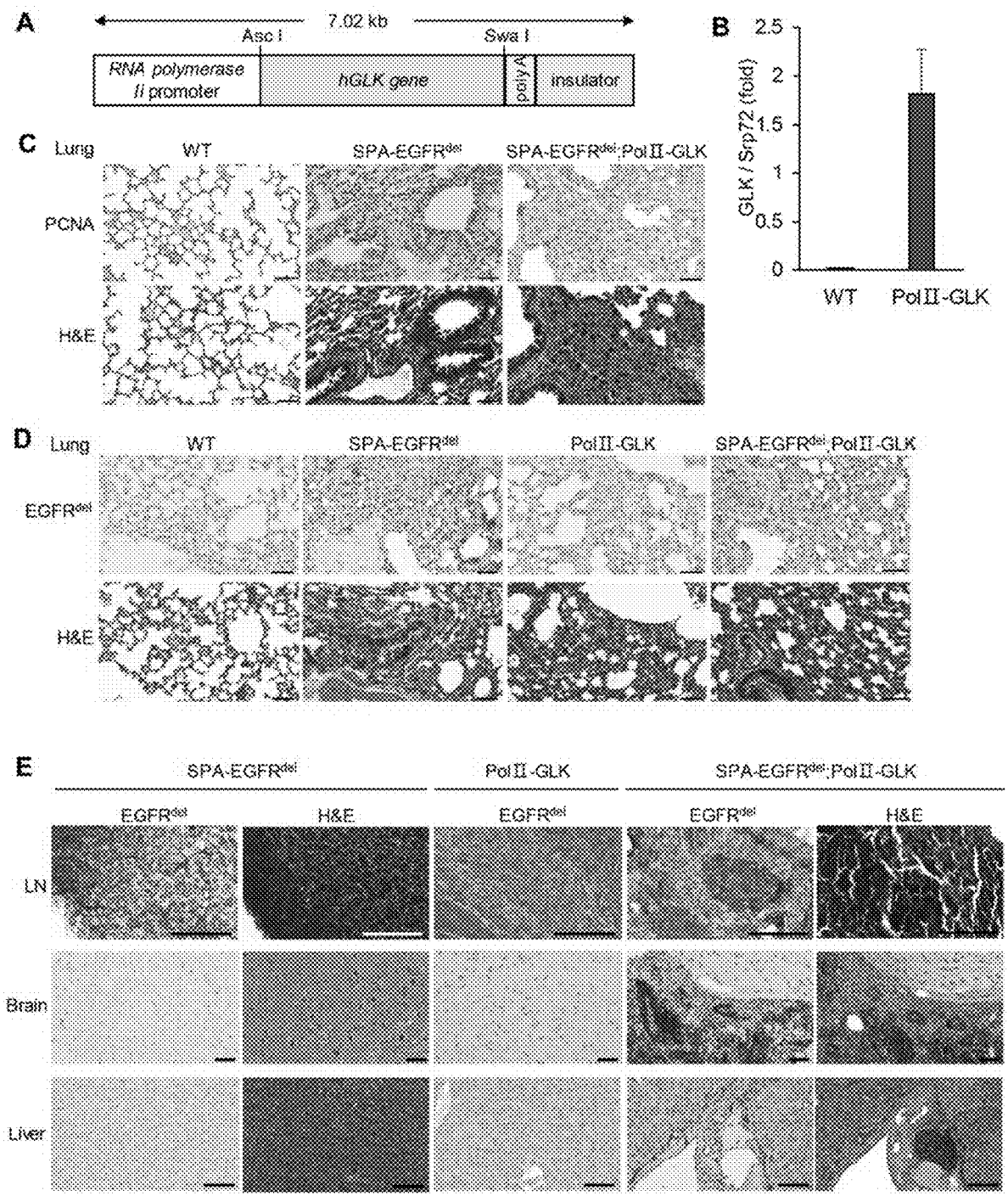

FIG. 13 shows that GLK induces distant metastasis of lung cancer. (A) Schematic diagram of the PolII-GLK transgenic construct. In GLK transgenic mice, human GLK cDNA was driven by the mouse RNA polymerase H (PolII) promoter. (B) Real-time PCR of transgenic human GLK (hGLK) mRNA levels in murine peripheral blood cells from mice. The human GLK mRNA levels were normalized to mouse Srp72 mRNA levels. Means±SEM are shown. WT, wild-type littermate controls; PolII-GLK, PolII-GLK transgenic mice. (C) Representative immunohistochemistry of a lung cancer maker proliferating cell nuclear antigen (PCNA) or H&E staining in lung tissues from 8-month-old wild-type (WT), SPA-EGFR$^{del}$ transgenic, or SPA-EGFR$^{del}$;PolII-GLK transgenic mice. Scale bar, 100 μm. (D and E) Representative immunohistochemistry of EGFR-deletion mutant expression or H&E staining in the lung (D), cervical lymph nodes (E), brain (E), or liver (E) from 1-year-old indicated mice. LN, cervical lymph nodes. Scale bar, 100 μm.

Figure 14:
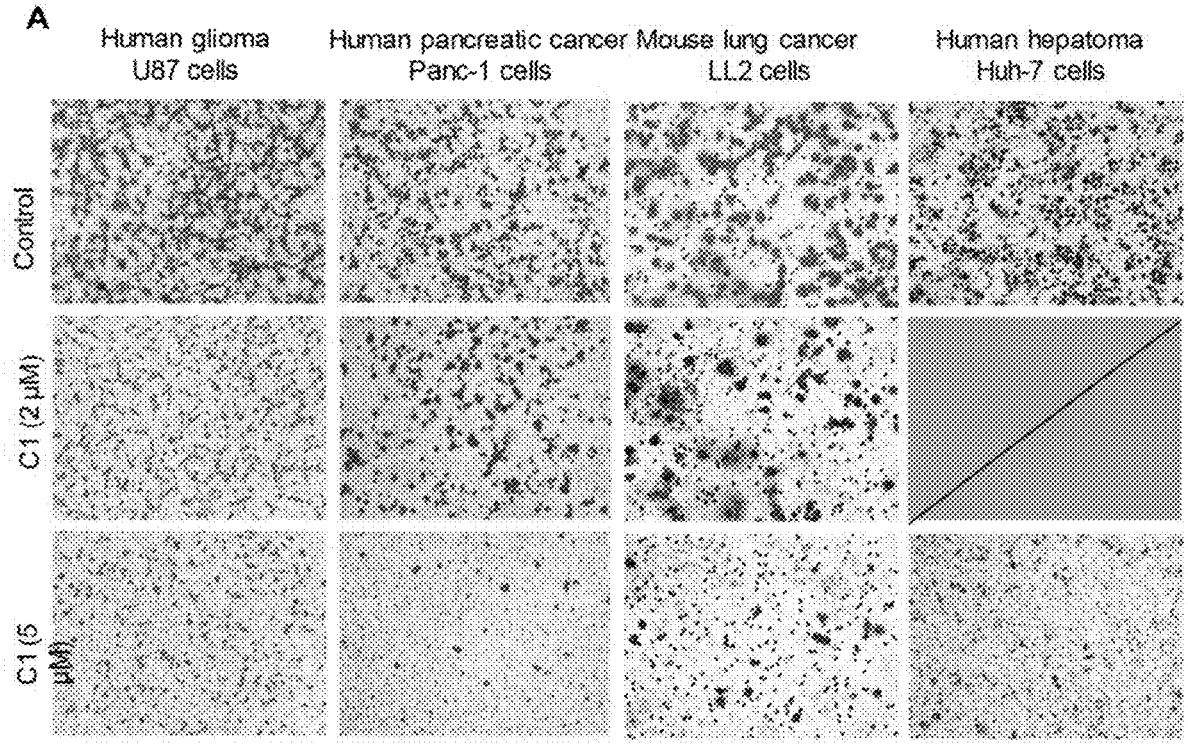
Figure 14:
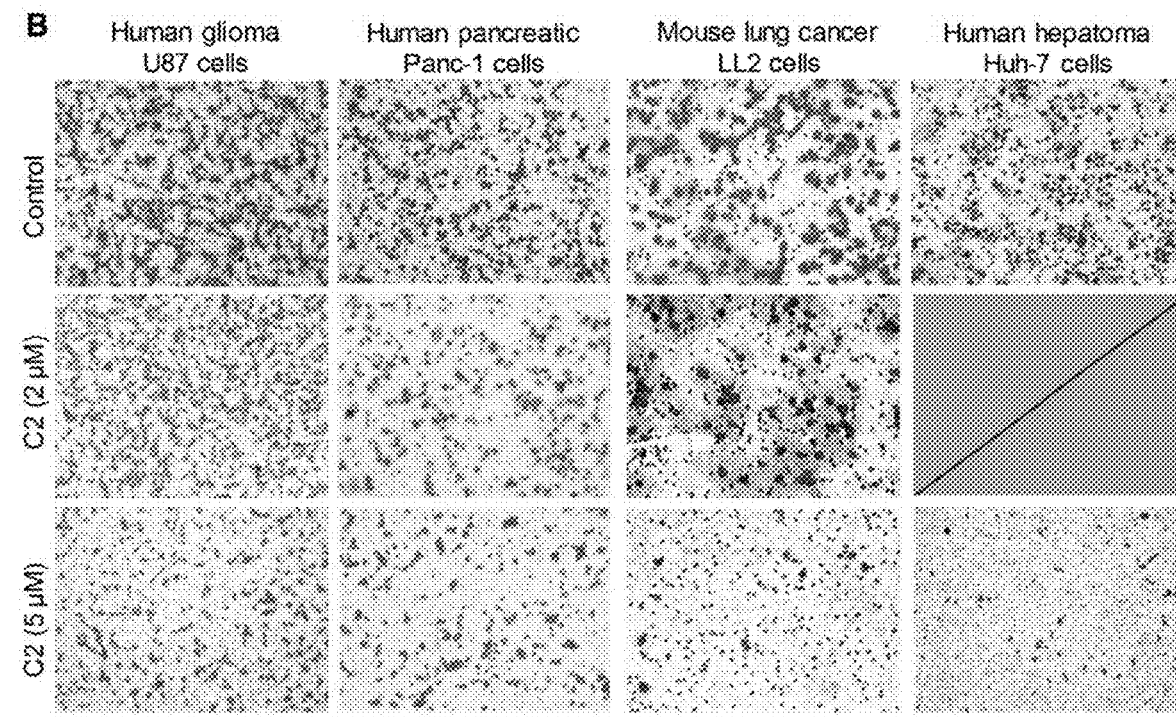

FIG. 14 shows that GLK inhibitors block the migration of cells from indicated cancers. Transwell migration assays of human glioma U87 cells, human pancreatic cancer Panc-1 cells, mouse lung cancer LL2 cells, or human hepatoma Huh-7 cells treated with the GLK inhibitor C1 (verteporfin) (a; 2 uM or 5 uM) or C2 (alexidine dihydrochloride) (b; 2 uM or uM). C1 denotes verteporfin; C2 denotes alexidine dihydrochloride.

Figure 15:
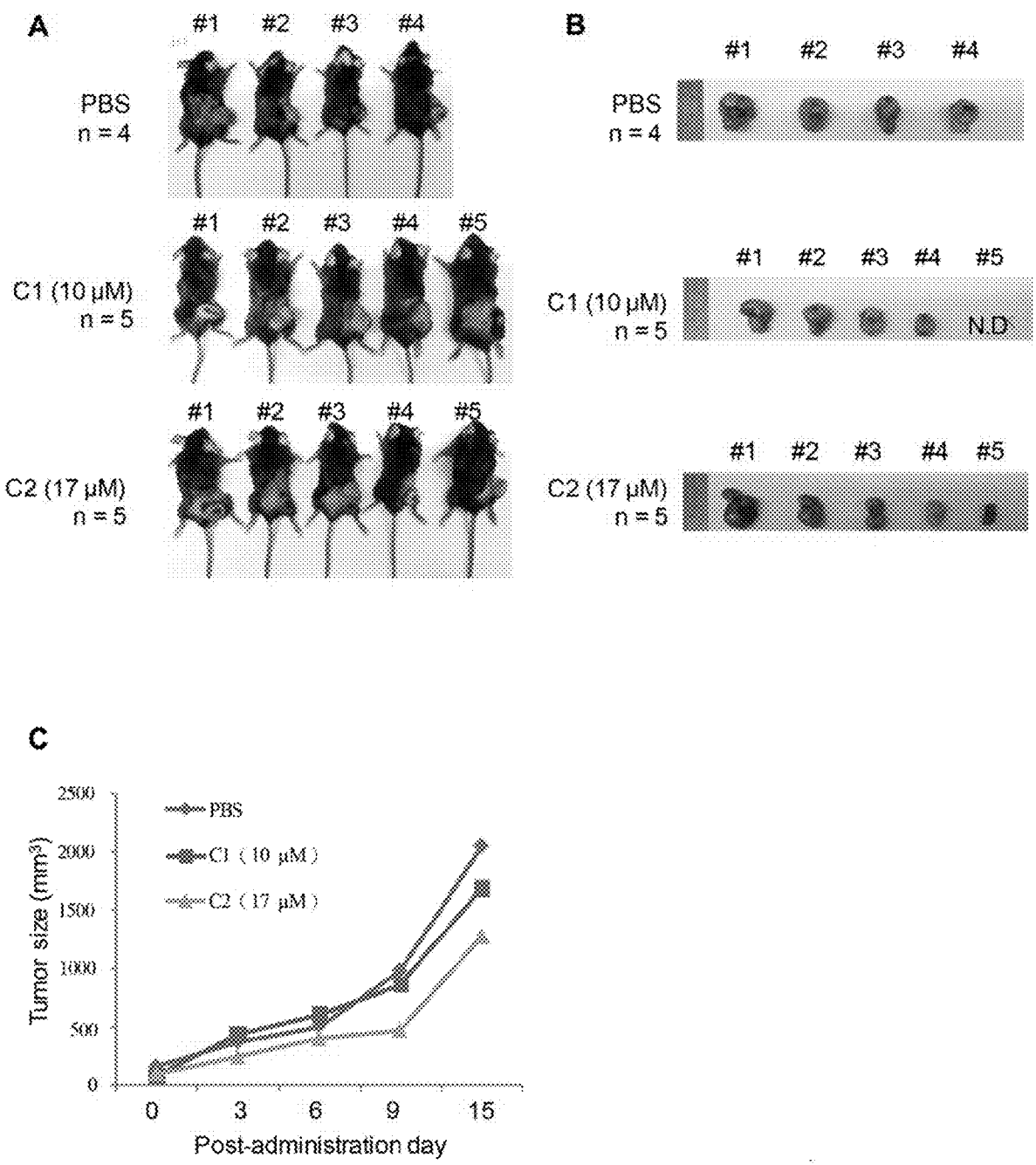

FIG. 15 shows that GLK inhibitors suppress the tumor growth in lung cancer xenograft model. (A) Murine TC-1 lung cancer cells were subcutaneously inoculated into the right flank of wild-type mice for establishing a TC-1 xenograft model. TC-1 cells inoculated mice were intravenously injected with PBS, C1 (verteporfin) (10 uM), or C2 (alexidine dihydrochloride) (17 uM) every 3 days for 15 days. (B) Photographs of excised TC-1 lung cancers after receiving PBS, C1 (verteporfin) (10 uM), or C2 (17 uM) treatment. (C) The growth (mean tumor volume) of tumor was measured for 15 days. The TC-1 tumor size progression as a function of time post-administration with C1 or C2. N.D., not detectable. C1 denotes verteporfin; C2 denotes alexidine dihydrochloride.

Figure 16:
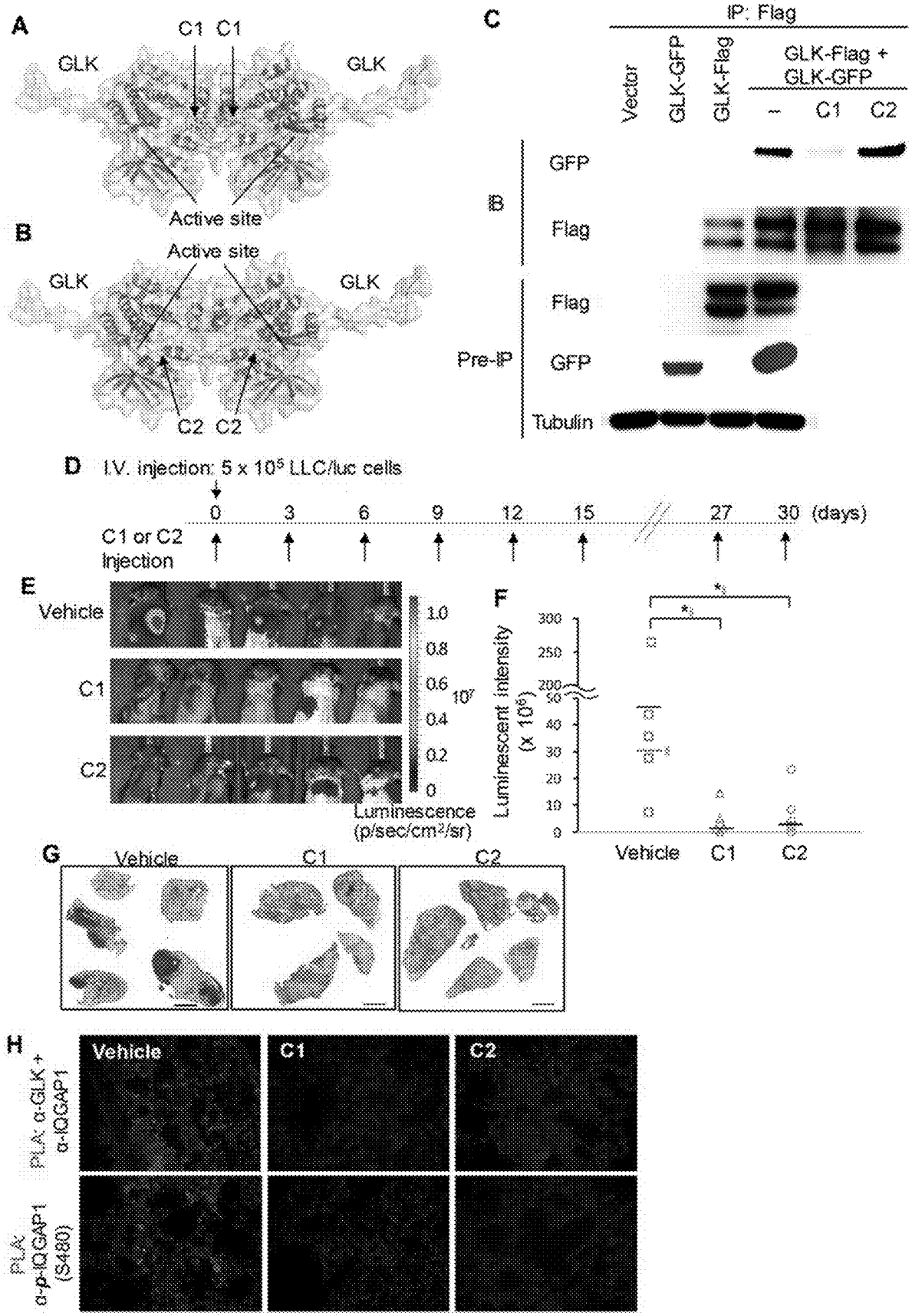

FIG. 16 shows that GLK inhibitors suppress lung cancer metastasis in mice. (A) The molecular docking of GLK kinase domain structure with C1 (verteporfin). A three-dimensional structure model depicts the binding of C1 to the predicted GLK kinase domain containing phosphorylated Ser-170. The putative binding affinity was −7.4 kcal/mol. (B) The molecular docking of GLK kinase domain structure with C2 (alexidine dihydrochloride). A three-dimensional structure model depicts the binding of C2 to the predicted GLK kinase domain containing phosphorylated Ser-170. The putative binding affinity was −7.0 kcal/mol. (C) Co-immunoprecipitation (co-IP) of Flag-tagged GLK and GFP-fusion GLK using lysates of HEK293T cells co-transfected with Flag-GLK and GFP-GLK plasmids. Cells were treated with C1 (verteporfin) or C2 (alexidine dihydrochloride). (D) Administration of the GLK inhibitor C1 (0.556 nmole/g) or C2 (0.085 nmole/g) every 3 days for 30 days in the LLC/luc metastatic lung cancer mouse model. (E) The luciferase activity in mice treated with C1 (verteporfin), C2 (alexidine dihydrochloride), or vehicle was detected by IVIS Spectrum. (F) Luminescent intensity of photons emitted from LLC/luc cells in the images in (e) was quantified. (G) Representative immunohistochemistry of H&E in lung tissues from mice treated with C1 (verteporfin), C2, or vehicle. Scale bar, 0.5 cm. (H) In situ PLA assays of the interaction between GLK and IQGAP1 (upper panel) or phosphorylated IQGAP1 Ser-480 (lower panel) in lung tissues from mice treated with C1 (verteporfin), C2 (alexidine dihydrochloride), or vehicle in the LLC/luc metastatic lung cancer mouse model. Original magnification, ×40.

Figure 17:
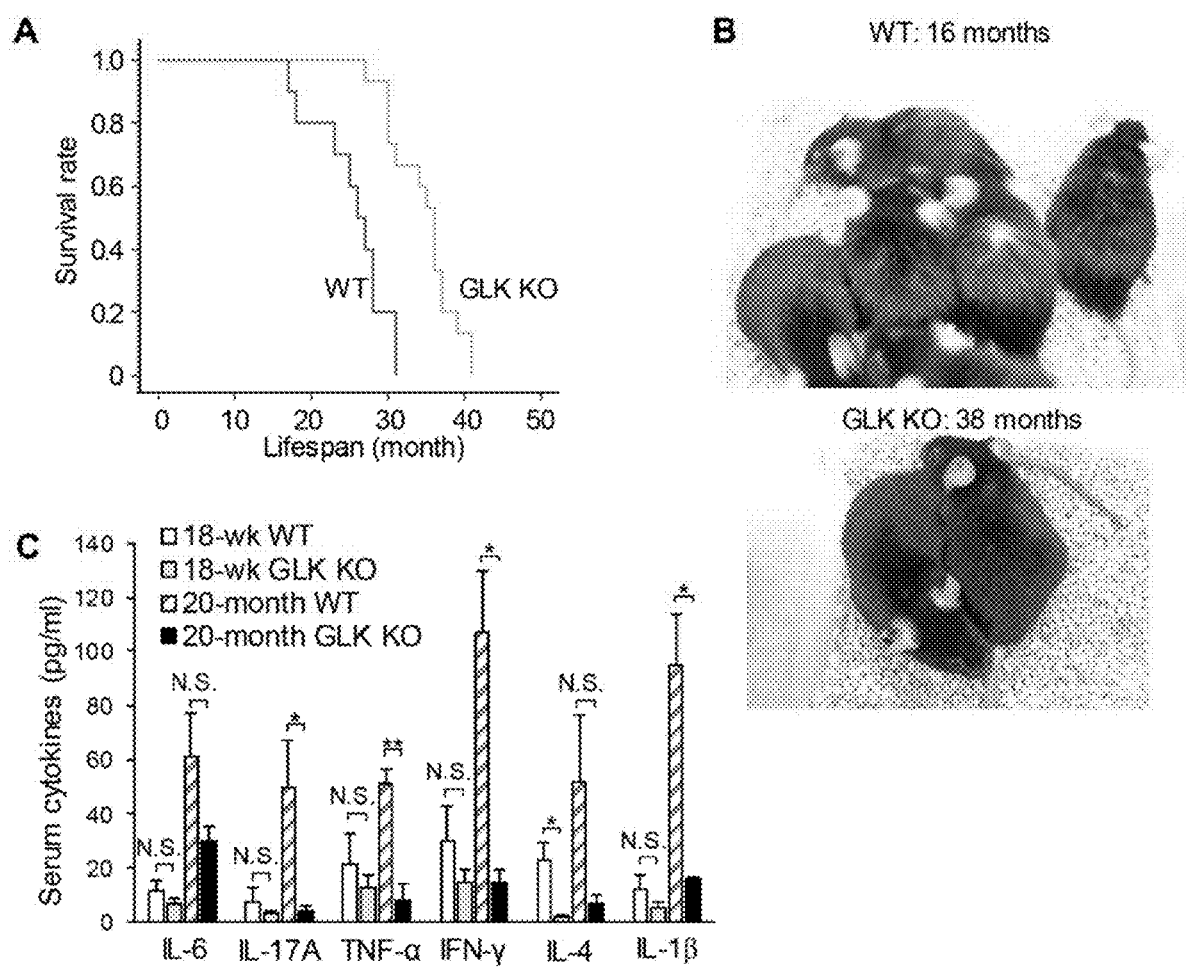

FIG. 17 shows that GLK-deficient mice display an increased lifespan. (A) Survival curves of 10 wild-type or 15 GLK-deficient mice were calculated by the life-table method. GLK-deficient mice exhibited a significant extension of lifespan relative to wild-type mice (Wilcoxon test, P=0.001). (B) 16-month-old wild-type mice displayed gray hair, whereas 38-month-old GLK-deficient mice still displayed healthy hair. (C) ELISA of various cytokines in the sera of 4.5-month-old wild-type, 20-month-old wild-type, or 20-month-old GLK-deficient mice. Means±SEM are shown. WT, wild-type mice; GLK KO, GLK-deficient mice. *, P value<0.05; **, P value<0.01 (two-tailed Student's t-test).

Figure 18:
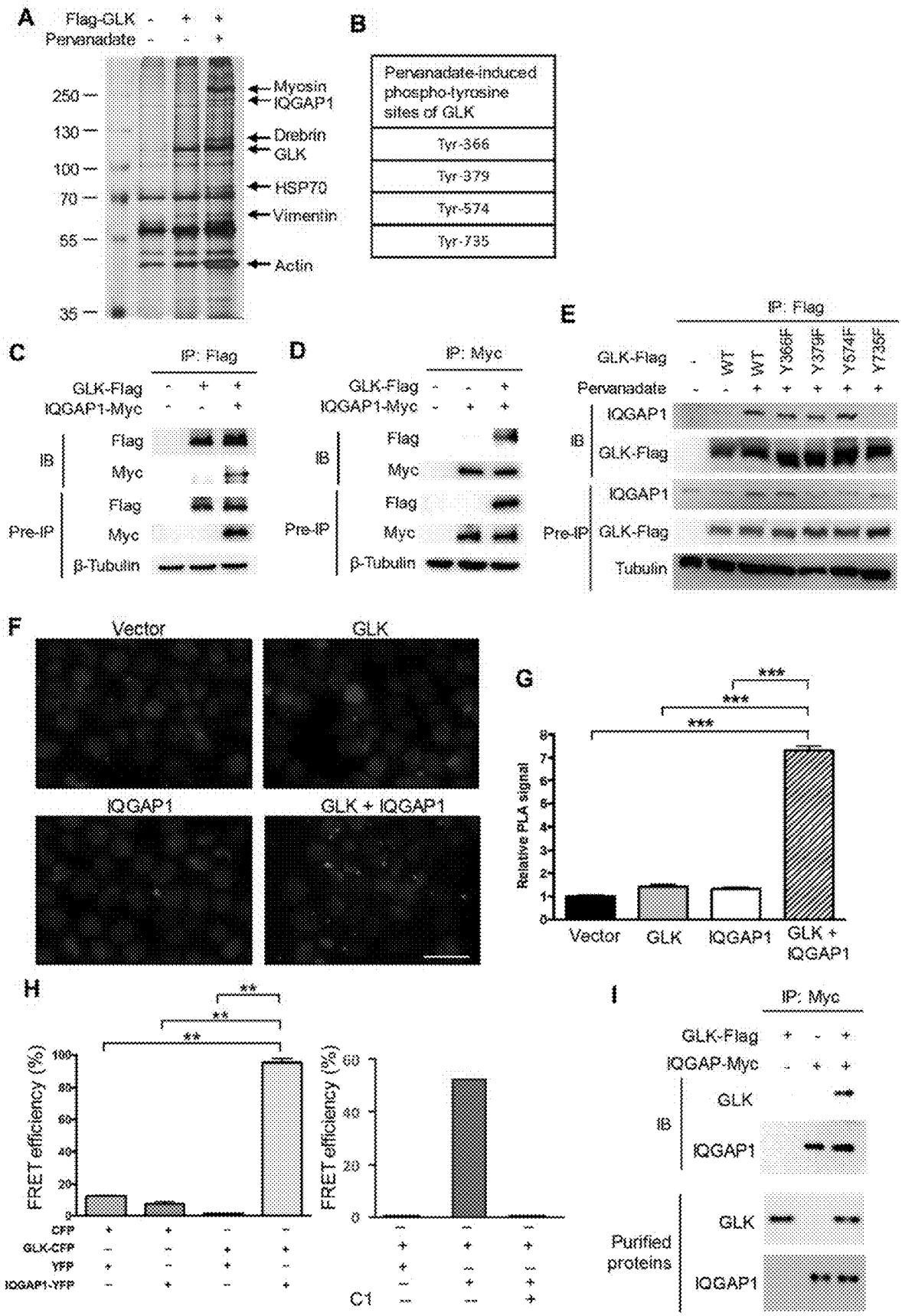

FIG. 18 shows that GLK interacts directly with IQGAP1. (A) Silver-stained gel of anti-Flag immunoprecipitates from HEK293T cells transfected with empty vector or Flag-tagged GLK in the presence or absence of the tyrosine phosphatase inhibitor pervanadate (25 μM). Arrows indicate the positions of GLK or GLK-interacting proteins. (B) Four pervanadate-induced tyrosine phosphorylation residues of GLK proteins were listed. (C and D) Co-immunoprecipitation of anti-Flag (C) or anti-Myc (D) immunocomplexes from lysates of HEK293T cells transfected with Flag-tagged GLK, Myc-tagged IQGAP1, or both plasmids. The whole-cell lysate immunoblots before immunoprecipitation (Pre-IP) are shown at the bottom of each panel. β-Tubulin was used as the loading control. (E) Co-immunoprecipitation of anti-Flag immunocomplexes from lysates of HEK293T cells transfected with either Flag-tagged GLK or Flag-tagged GLK mutant (Y366F, Y379F, Y574F, or Y735F). HEK293T cells were treated with 25 μM pervanadate for 2 h (F) In situ PLA of HEK293T cells transfected with empty vector, 3× Flag-tagged GLK, Myc-tagged IQGAP1, or GLK together with IQGAP1 plasmids. Arrows indicate the PLA signals (red spots). Original magnification, ×40. Scale bar, 10 μm. (G) The relative PLA signal of each group per field is shown on the plot. (H) FRET assays of HEK293T cells transfected with the indicated plasmids encoding CFP- and YFP-fused GLK and IQGAP1 proteins. The FRET signals were inhibited by the treatment of C1 (verteporfin) or C2 (alexidine dihydrochloride) (tight panel). (I) Co-immunoprecipitation (Co-IP) of purified Flag-tagged GLK and Myc-tagged IQGAP1 proteins. Flag-tagged GLK and Myc-tagged IQGAP1 proteins from HEK293T cell lysates were eluted with Flag and Myc peptides, respectively. , P value<0.01; *, P value<0.001.

Figure 19:
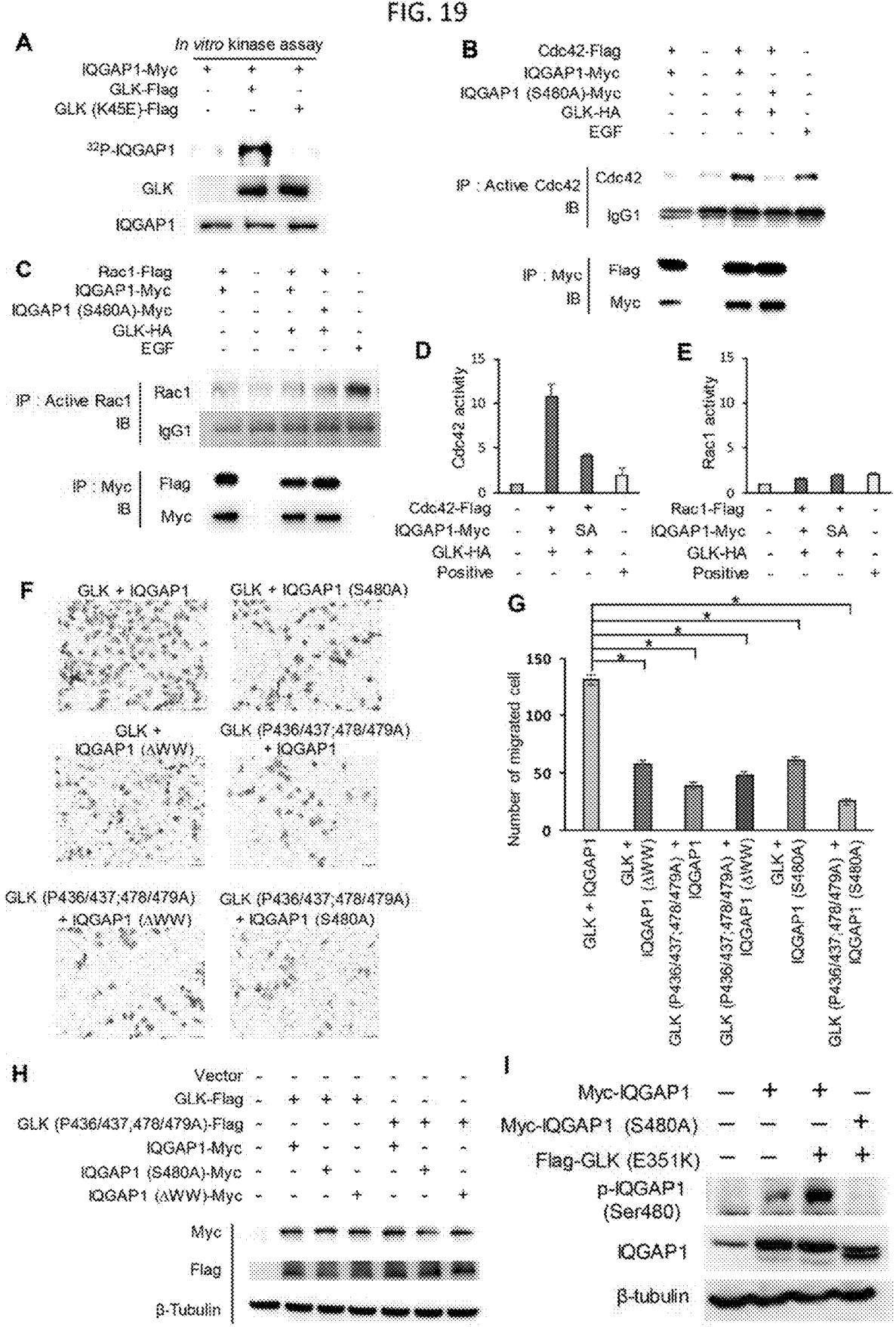

FIG. 19 shows that phosphorylation of IQGAP1 at Ser-480 by GLK controls lung cancer cell migration. (A) In vitro kinase assay and immunoblotting of purified wild-type GLK, kinase-dead GLK, and IQGAP1. Phosphorylation of IQGAP1 was then quantified by a Typhoon scanner (GE). (B) Active (GTP-binding) Cdc42 proteins were immunoprecipitated from lysates of HEK293T cells co-transfected with Cdc42 and GLK plus either IQGAP1 or IQGAP1 (S480A) mutant, followed by immunoblotting analyses. Lower panel showed the co-immunoprecipitation (interaction) between IQGAP1 and Cdc42. (C) Active (GTP-binding) Rac1 proteins were immunoprecipitated from lysates of HEK293T cells co-transfected with Rac1 and GLK plus either IQGAP1 or IQGAP1 (S480A) mutant, followed by immunoblotting analyses. Lower panel showed the co-immunoprecipitation (interaction) between IQGAP1 and Rac1. (D and E) Cdc42 or Rac1 enzymatic activity the cell lysates as in (B) or (C) was determined using G-LISA Activation Assay Biochem Kit. Positive, positive controls from the assay kit. SA, IQGAP1 (S480A) mutant. (F) Migration assays of HCC827 cells transfected with Flag-tagged GLK or GLK (P436/437A;P478/479A) plasmid plus the plasmid expressing Myc-tagged IQGAP1, IQGAP1 (S480A), or IQGAP1 (ΔWW). Original magnification, ×10. Scale bar, 20 μm. (G) The relative number of migrated cells per field is shown on the plot. (H) Immunoblotting of GLK and IQGAP1 proteins from HCC827 cells transfected with the indicated plasmids. (I) Immunoblotting of phospho-IQGAP1 (Ser-480) in HEK293T cells co-transfected with Flag-tagged active-form GLK (E351K) plus either Myc-tagged IQGAP1 WT or IQGAP1-S480A mutant. *, P value<0.05.

Figure 20:
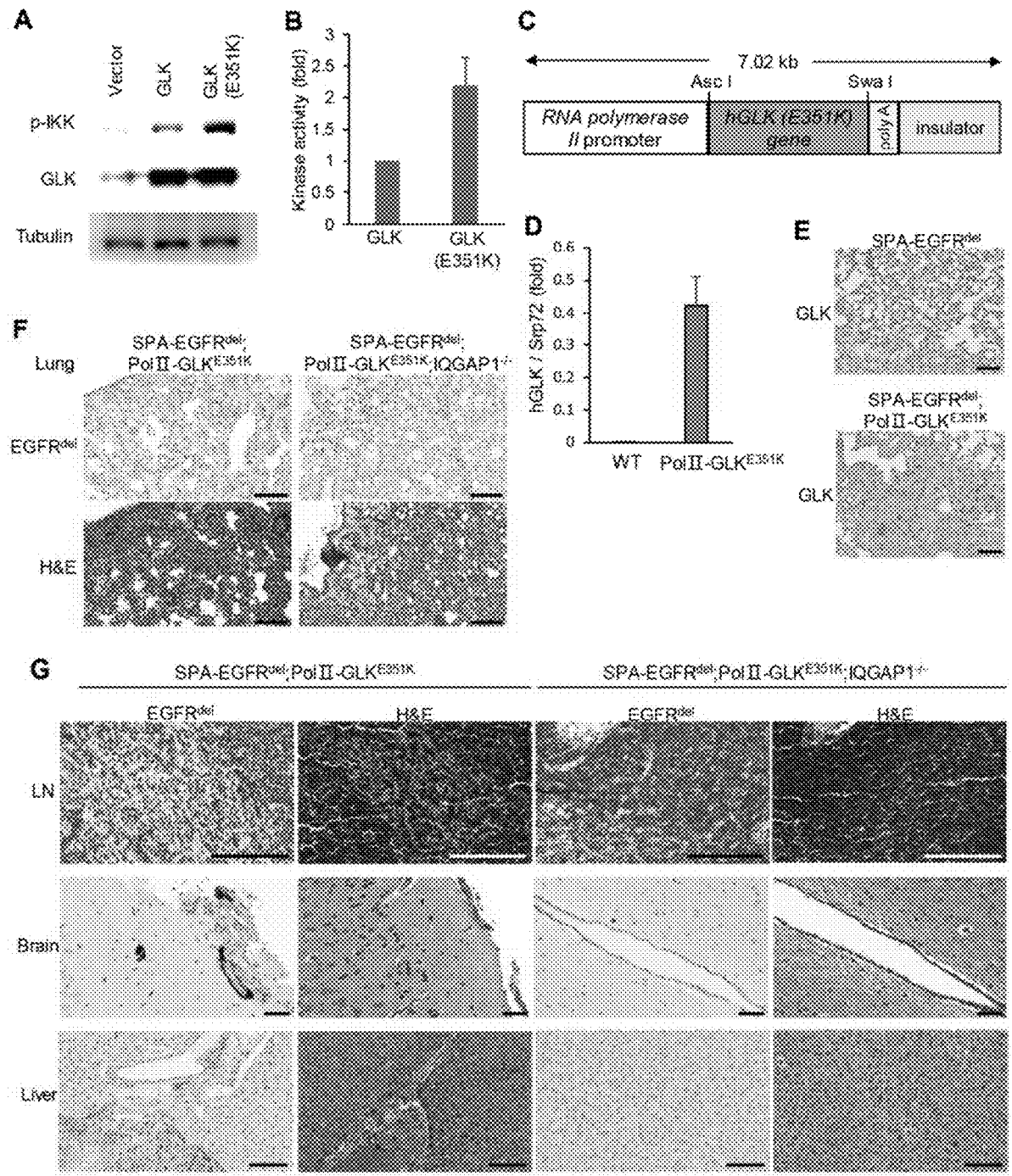

FIG. 20 shows that GLK induces distant metastasis of lung cancer. (A) Constitutively activated GLK (E351K) mutant induces higher phosphorylation levels of IKK than wild-type GLK. Immunoblotting of phospho-IKK and GLK proteins from Jurkat T cells transfected with the indicated plasmids. Tubulin was used as the loading control. (B) ADP-based kinase assays of GLK or GLK (E351K) mutant proteins. Flag-tagged GLK or GLK (E351K) proteins were immunoprecipitated from transfected HEK293T cell lysates. (C) Schematic diagram of the Pol II-GLK-E351K transgenic construct. Constitutively activated human GLK (E351K) mutant cDNA was driven by the mouse RNA polymerase II (Pol II) promoter. (D) Real-time PCR of transgenic human GLK-E351K (hGLK$^{E351K}$) mRNA levels in murine peripheral blood cells from mice. The human GLK mRNA levels were normalized to mouse Srp72 mRNA levels. WT, n=4; Pol II-GLK$^{E351K}$, n=4. Means±SEM are shown. WT, wild-type littermate controls; Pol II-GLK$^{E351k}$, GLK$^{E351K}$ transgenic mice. (E) Immunohistochemistry of GLK expression in the lung cancer from SPA-EGFR$^{del}$ transgenic mice and SPA-EGFR$^{del}$;Pol II-GLK$^{E351K}$ transgenic mice. Scale bar, 100 μm. (F) Representative immunohistochemistry of EGFR-deletion mutant expression and H&E staining in the lung cancer from 7-month-old SPA-EGFR$^{del}$;Pol II-GLK$^{E351K}$ transgenic mice and SPA-EGFR$^{del}$;Pol II-GLK$^{E351K}$;IQGAP1$^{-/-}$ mice. Scale bar, 100 μm. (G) Representative immunohistochemistry of EGFR-deletion mutant expression or H&E staining in the brain and liver from 7-month-old SPA-EGFR$^{del}$;Pol II-GLK$^{E351K}$ transgenic mice and SPA-EGFR$^{del}$;Pol II-GLK$^{E351K}$;IQGAP1$^{-/-}$ mice. Scale bar, 100 μm. Comparison of EGFR-deletion mutant expression in tissues from individual groups (lower panel).

Figure 21:
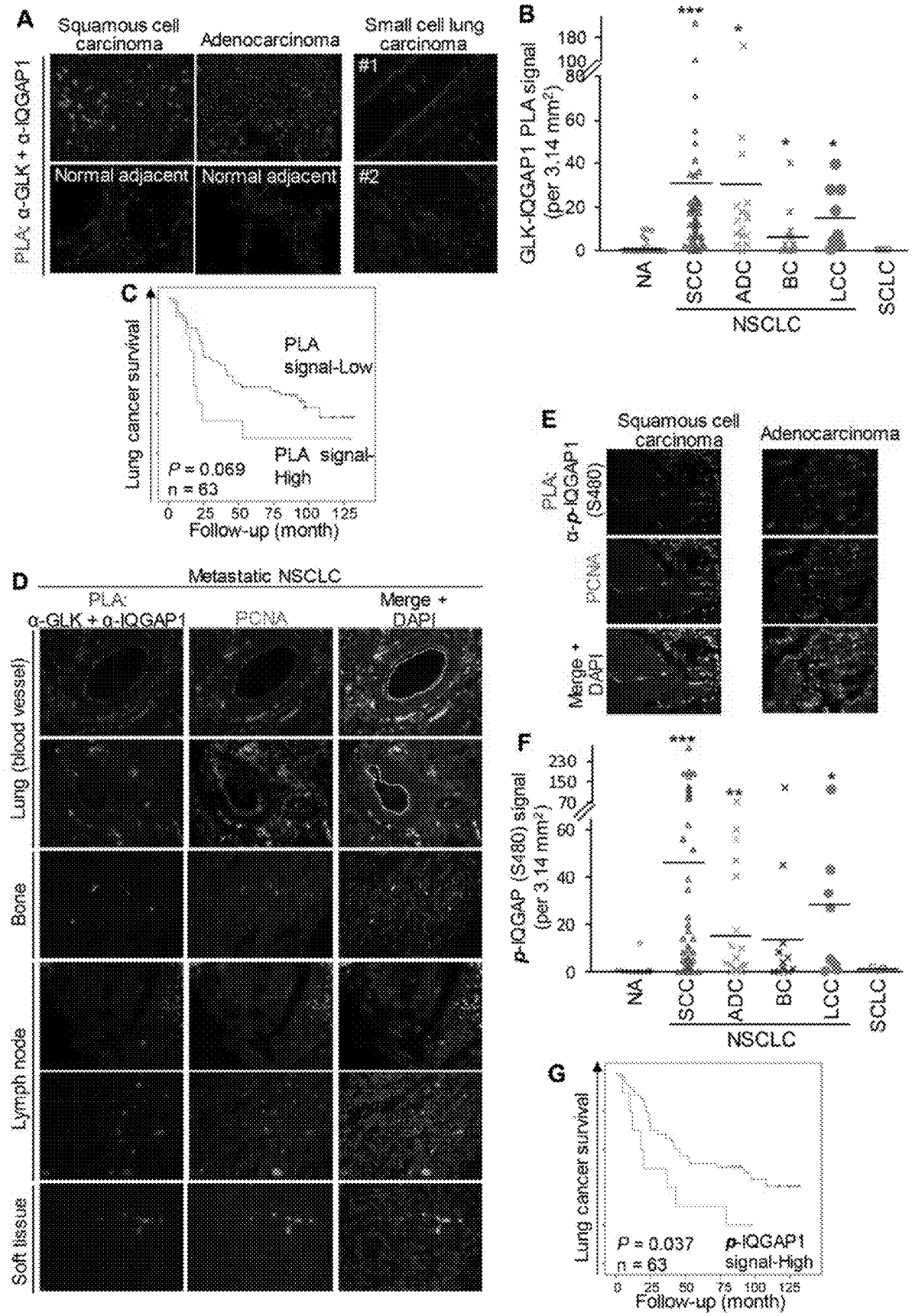

FIG. 21 shows that GLK–IQGAP1 complex is correlated with poor survival of human NSCLC. (A) In situ PLA assays of the interaction between GLK and IQGAP1 in normal adjacent tissues, squamous cell carcinoma (one type of NSCLC) tissues, adenocarcinoma (one type of NSCLC) tissues, and small cell lung carcinoma (SCLC) tissues from representative patients. Original magnification, ×40. (B) The PLA signals of the interaction between GLK and IQGAP1 each group per tissue are shown on the plot. NSCLCs included squamous cell carcinoma (SCC, n=56), adenocarcinoma (ADC, n=17), bronchioloalveolar carcinoma (BC, n=11), and large cell carcinoma (LCC, n=8). Normal adjacent (NA) tissues, n=68. Small cell lung carcinoma (SCLC), n=3. (C) Kaplan-Meier estimates of survival according to GLK–IQGAP1 PLA signals (PLA signal-High versus PLA signal-Low) of NSCLCs (n=66). P values were calculated using the log-rank test (D) In situ PLA of the interaction between GLK and IQGAP1 in metastatic NSCLC cells of the lung, the lymph node, and the bone tissues. PCNA staining (in green, FITC) was used to label lung cancer cells. Dotted lines indicate the vascular wall of blood vessels in the lung tissue. (E) In situ PLA of phosphorylated IQGAP1 Ser-480 in the tumor tissues from a representative squamous cell carcinoma patient and a representative adenocarcinoma patient using a combination of paired PLA probes corresponding to IQGAP1 and phospho-IQGAP1 (Ser-480). PCNA staining (in green, FITC) was used to label lung cancer cells. Original magnification, ×40. (F) The PLA signals of the interaction between GLK and IQGAP1 each group per tissue are shown on the plot. NSCLCs included squamous cell carcinoma (SCC, n=53), adenocarcinoma (ADC, n=17), bronchioloalveolar carcinoma (BC, n=11), and large cell carcinoma (LCC, n=8). Normal adjacent (NA) tissues, n=68. Small cell lung carcinoma (SCLC), n=3. (G) Kaplan-Meier estimates of survival according to p-IQGAP1 (Ser-480) PLA signals (PLA signal-High versus PLA signal-Low) of NSCLCs (n=63). Among the tissue arrays, three SCC tissues on the tissue array slide were damaged; therefore, only 63 of 66 tissues were analyzed. P values were calculated using the log-rank test.

DETAILED DESCRIPTION OF THE INVENTION

The term "anti-phospho-RORγt [Ser489] antibody" refers to "an antibody against phosphorylated RORγt serine-489, which may be generated by immunization of a rabbit with phospho-peptides (for example, murine RORγt epitope: $^{483}$FSTDVE[pS]PEGLSK$^{495}$; SEQ ID NO. 5)".

The term "AhR+RORγt+IKKβ overexpressing cells" refer to cells that are co-transfected with 3 different plasmids encoding AhR, RORγt, and IKKβ, respectively, and exhibit overexpression of the three proteins in the cells.

The term "secondary antibodies as PLA probes" refers to a pair of oligonucleotide-labeled secondary antibodies, which are DUOLINK® anti-rabbit PLUS and anti-mouse MINUS PLA probes. These probes are anti-mouse IgG and anti-Rabbit IgG.

Abbreviations: Cyan Fluorescent Protein (CFP); Yellow fluorescent protein (YFP); DYKDDDDK (SEQ ID NO: 1; FLAG™ peptide); Aryl Hydrocarbon Receptor (AhR; SEQ ID NO: 29); Retinoic-acid-receptor-related orphan nuclear receptor gamma t (RORγt) (or RAR-related orphan receptor gamma, transcript variant 2; SEQ ID NO.: 30); ras GTPase-activating-like protein IQGAP1 (SEQ ID NO: 28); Mus IL17A promoter sequence (SEQ ID NO: 31).

We have discovered that GLK signaling induces a novel interaction between AhR and phospho-RORγt through PKCθ and IKKβ, leading to IL-17A transcriptional activation and autoimmune responses. The invention has made the following contributions to the art: (1) RORγt serine-489 phosphorylation site; (2) AhR/phospho-RORγt complex; (3) IKKβ phosphorylates RORγt serine-489; (4) GLK-PKCθ-IKKβ-AhR/RORγt-IL-17A; (5) GLK signaling selectively induces IL-17A transcription; (6) TCR stimulation also induces RORγt serine-489 phosphorylation; (7) GLK overexpression-induced RORγt serine-489 phosphorylation and AhR/phospho-RORγt complex in human autoimmune patient T cells; and (8) Identification of 2 small-molecule GLK inhibitors that suppress AhR/phospho-RORγt complex, IL-17A production, or autoimmune responses. Our findings suggest that inhibitors (such as verteporfin or alexidine dihydrochloride) of GLK or AhR/RORγt complex formation could be used as IL-17A-blocking agents for IL-17A-mediated autoimmune diseases.

EXAMPLES

Methods

Mice.

All animal experiments were performed in the AAALAC-accredited animal housing facilities at National Health Research Institutes (NHRI). All mice were used according to the protocols and guidelines approved by the Institutional Animal Care and Use Committee of NHRI. Floxed AhR mice (JAX 0062003), IL-17A-deficient mice (JAX 016879), floxed RORγt mice (JAX 008771), and floxed IKKβ mice (EMMA 001921) were purchased from Jackson Laboratory or European Mouse Mutant Archive (EMMA). The three aforementioned mouse lines were backcrossed for 10 generations onto the C57BL/6 background. The data presented in this study were performed on sex-matched, 4- to 26-week-old littermates. For T-cell development analyses, 5-week-old, sex-matched mice were used. All mice used in this study were maintained in temperature-controlled and pathogen-free cages.

Generation of Lck-GLK Transgenic Mice and PKCθ Knockout Mice.

A full-length human GLK coding sequence was placed downstream of the proximal lck promoter. Lck-GLK Tg mice in C57BL/6 background were generated using pronuclear microinjection. Two independent Lck-GLK Tg mouse lines were used. PKCθ knockout mice were generated by TALEN-mediated gene targeting. The nucleotides 5'-GGTG- GAACACTAAAAATAATATGTCTTAGAGCCCCATA-CATACAGTGTTTGTCTTTTGTCAT TTTTCTAGG-GAACAACC<u>ATG</u>TCACCGTTTC-3' (SEQ ID NO: 2) of the PKCθ intron 1 and exon 2 were deleted in the mutated allele. For TALEN-mediated gene targeting in mice, embryo microinjection of TALEN mRNA was performed.

Generation of Pol II-GLK Transgenic Mice and IQGAP1 Knockout Mice.

Pol II-GLK Tg mice and Pol II-GLKE351K Tg mice in C57BL/6 background were generated using pronuclear microinjection by NHRI Transgenic Mouse Core. A full-length human GLK coding region (wild-type or E351K mutant) was placed downstream of the RNA polymerase II (Pol II) promoter. IQGAP1 knockout mice in C57BL/6 background were generated using embryo microinjection of TALEN mRNA by NHRI Transgenic Mouse Core. The nucleotide (nt) 161 guanine of the IQGAP1 exon 1 was deleted in the mutated allele.

Cells.

Human Jurkat T leukaemia cells (TIB-152) were cultured in RPMI-1640 medium (Invitrogen) containing 10% fetal calf serum plus penicillin (10 units per ml) and streptomycin (10 mg per ml). HEK293T cells were cultured in Dulbecco's modified Eagle's medium containing 10% FCS plus penicillin (10 units per ml) and streptomycin (10 mg per ml). All cell lines used were tested and confirmed to be negative for mycoplasma. Primary murine T cells were negatively selected from the spleen, lymph nodes, or peripheral bloods of mice using magnetically coupled antibodies against CD11b, B220, CD49b, CD235, and TER-1 19 (MACS). To induce IL-17A production of 3-day-cultured T cells (FIG. 1E), the primary T cells were stimulated with Biotin-conjugated anti-CD3 antibodies (3 μg per ml) plus streptavidin (3 μg per ml) for 3 h at 37° C.

Reagents and Antibodies.

GLK antibody (α-GLK-N) was generated by immunization of rabbits with peptides (murine GLK epitope: [4]GFDLSRRNPQEDFELI[19]: SEQ ID NO: 3; identical to human GLK protein sequences 4-19) and was used for FIGS. 2E, 3D-E and 4F. Anti-GLK monoclonal antibody (clone C3) was generated by immunization of mice with peptides (murine GLK epitope: [514]EQRGTNLSRKEKKDVPKPI[533]; SEQ ID NO: 4) and was used for FIGS. 3F, 3I. The antibody for phosphorylated RORγt Ser-489 was generated by immunization of a rabbit with phospho-peptides (murine RORγt epitope: [483]FSTDVE[pS]PEGLSK[495]; SEQ ID NO: 5; corresponding to the human RORγt protein sequences [485]FSTETE[pS]PVGLSK[497]; SEQ ID NO: 6). Anti-Myc (clone 9E10), anti-Flag (clone M2), and anti-HA (clone 12CA5) antibodies were purchased from Sigma. Anti-p-AhR (Ser-36; # A0765) antibody was purchased from Assay Biotechnology. Anti-AhR (clone RPT9), anti-p-IKKβ (Ser-180/181; # ab55341), and antiGAPDH (clone mAbcam 9484, catalog # ab9482) antibodies were purchased from Abeam. Anti-PKCθ (#3551-1) and anti-Actin (clone E184) antibodies were purchased from Epitomics. Anti-p-PKCθ (Thr-538; # ab63365), anti-p-STAT3 (Tyr-705; clone D3A7), anti-IKKα (#2682), anti-IKKβ (#2678), anti-p-SGK1 (Thr-256; #2939), anti-SGK1 (clone D27C11), anti-Histone 3 (#97158), anti-IRF4 (#49648), and anti-BATF (#86388) antibodies were purchased from Cell Signaling. Anti-STAT3 (#06-596) and anti-RORγt (clone 6F3.1) antibodies were purchased from Millipore. Anti-KLF4 (# AF3158) and anti-IL-23 receptor (# bs-1460) antibodies were purchased from R&D and Bioss, respectively.

Plasmids and Recombinant Proteins.

The expression plasmids for GLK and GLK kinase-dead mutant (GLK-K45E) were reported previously. CFP-tagged PKCθ, YFP-tagged AhR, CFP-tagged AhR, Myc-tagged PKCθ, HA-tagged AhR, and Flag-tagged PKCθ plasmids were constructed by subcloning individual cDNAs into pCMV6-AC-CFP, pCMV6-AC-YFP, pCMV6-AC-Myc, pCMV6-AC-HA, or pCMV6-AC-Flag vector. FLAG™-tagged RORγt and YFP-tagged RORγt plasmids were constructed by subcloning RORγt cDNA into pCMV6-AN-Flag or pCMV6-AN-YFP vector. HA-tagged IKKβ plasmid was constructed by subcloning IKKβ cDNA into pRC-HA vector. HA-tagged AhR-S36A mutant and Myc-tagged PKCθ-K409W (kinase-dead) mutant plasmids were generated by site-directed mutagenesis. GST-tagged PKCθ and GST-tagged PKCθ-K409W plasmids were also individually constructed by subcloning into pGFX4T vector. The human GLK shRNA (5'-GTGCCACTTAGAATGTTTGAAA-3 SEQ ID NO: 7) was subcloned into pSUPER-GFP vector (OligoEngine). The IL-17A reporter plasmid was a gift from Dr. Warren Strober (Addgene plasmid #20124). The IL-17A promoter constructs containing a mutated binding element for AhR, RORγt (−877), RORγt (−120), or STAT3 were generated by site-directed mutagenesis using PHUSION™ DNA polymerase (Thermo Fisher) according to the manufacturer's protocol. The following primers were used for mutagenesis (mutated nucleotides are shown in bold font): AhR-binding site, 5'-ATGTCCATACA<u>TACATGA</u>TACTGAATCACAGC-3' (SEQ ID NO: 8); RORγt-binding site (−887), 5'-CTCAAAGACAT-AAAGGCAA<u>CCGTGA</u> TCTCATGG AGAGGAGAG-3' (SEQ ID NO. 9), RORγt-binding site (−120), 5'-GGTTCTGTG<u>CTGCA</u>ATCATTTGAGG (SEQ ID NO. 10); STAT3-binding site, 5'-AGACAGATGTTGC<u>CTGTCA</u>TAAAGGGGTGGTT-3' (SEQ ID NO:11). The mutant constructs were verified by DNA sequencing. The plasmids pGL4.43-Luc2P-XRE (AhR responsive XRE-Luc), pGL4.47-Luc2P-SIE (STAT3 responsive SIE-Luc), pGL4.32-Luc2P-NF-κB-RE-Hygro, and pGL4 luciferase reporter vector were purchased from Promega. The plasmid for RORγt (−877) response element-driven reporter was constructed by cloning four copies of RORγt (−877) response element into pGL4.43 luciferase reporter vector. For in vitro binding assays, purified AhR proteins were isolated from HA-AhR-transfected HEK293T cells, followed by HA-peptide elution. Purified recombinant GST-PKCθ and GST-IKKβ proteins were purchased from SignalChem. Purified recombinant 6×His-RORγ proteins were purchased from MyBioSource. Recombinant proteins of GST-tagged PKCθ K409W proteins were isolated from $E.\ coli$ (BL21) and then purified by GST-pulldown assays. Purified Flag-tagged RORγt protein was immunoprecipitated and then eluted with Flag peptides from lysates of HEK293T cells that were co-transfected with Flag-RORγt plus either CFP-IKKβ or vector. Purified recombinant protein of GST-tagged AhR was purchased from Abnova.

Luciferase Reporter Assays.

The 2-kb IL-17A promoter-driven firefly-luciferase reporter plasmid and a renilla-luciferase control plasmid (pRL-TK) were co-transfected into Jurkat T cells. After 24 h, $10^6$ cells were harvested, washed with PBS, and resuspended in 60 μl RPMI medium plus 60 μl lysis buffers. Data represent the mean of the ratios of the firefly-luciferase activity to the renilla-luciferase activity.

Enzyme-Linked Immunosorbent Assays (ELISAs).

Serum levels of IL-1β, IL-4, IL-6, IL-12, IL-17F, IL-21, IL-22, IL-23, IFN-γ, TNF-α, and TGF-β were analyzed by individual ELISA kits purchased from eBioscience. The IL-17A levels were determined using an ELISA kit from Biolegend. The serum levels of anti-nuclear antibodies (ANA), anti-dsDNA antibody, and rheumatoid factor (RF) were analyzed by ELISA kits purchased from Alpha Diagnostic International.

Amplified Luminescent Proximity Homogeneous Assays (ALPHA).

ALPHA technology/protein-protein interaction assays were performed according to the manufacturer's protocol from Perkin Elmer Life Sciences. When the protein-donor pair was within 200 nm, a luminescent signal was detected by EnVision 2104 Multilabel Reader.

Fluorescence Resonance Energy Transfer (FRET) Assays.

FRET signal in live cells was detected by EnVision 2104 Multilabel Plate Reader (Perkin Elmer). The reaction was excited by light passing through a 430-nm filter (with 8 nm bandwidth), and the intensity of emitted fluorescence passing through a 530-nm filter (with 8 nm bandwidth) was recorded. If the protein-protein pair is in close proximity (1-10 nm), a 530-nm signal will be detected. The FRET efficiency was calculated using the following equation: FRET efficiency=((FRET−CFP×a−YFP×b)/YFP)×100%, where FRET, CFP, and YFP correspond to the fluorescent intensities acquired through FRET, CFP, and YFP filter sets, respectively; a and b are the donor emission and acceptor excitation crosstalk ratios, respectively.

In Situ Proximity Ligation Assay (PLA) for AhR-RORγt Complex.

PLA assays were performed using the DUOLINK® In Situ Red Starter kit (Sigma) according to the manufacturer's instructions. Briefly, cells were incubated with rabbit or mouse primary antibodies for each molecule pair (AhR plus PKCθ, AhR plus RORγt, or Flag plus Myc), followed by species-specific secondary antibodies-conjugated with oligonucleotides (PLA probes). After ligation and amplification reactions, the PLA signals from each pair of PLA probes in close proximity (<40 nm) were visualized as individual red dots by a fluorescence microscope (Leica DM2500) or a confocal microscope (Leica TCS SP5II). Each red dot represents for a direct interaction.

In Situ Proximity Ligation Assay (PLA) for GLK–IQGAP1 Complex and Phosphorylated IQGAP1.

Cells seeded on sterile cover slides were co-transfected with Flag-tagged GLK and Myc-tagged IQGAP1 expression plasmids, followed by fixation, permeabilization, and blocking. In situ PLA assays of GLK–IQGAP1 complex were performed using the DUOLINK® In Situ-Red kit (Sigma) according to the manufacturer's instructions.

For experiments using human pulmonary tissues, tissue sections were deparafinized, antigen retrieved, and nonspecific-binding blocked, followed by in situ PLA assays using primary antibodies for IQGAP1 (1:4,000, CUSABIO) plus either GLK (1:3,000, mAb clone C3) or phospho-IQGAP1 Ser-480 (1:2,000, Allbio Science). The monoclonal antibody for phosphorylated IQGAP1 Ser-480 was generated by immunization of a mouse with phospho-peptides (human IQGAP1 epitope: $^{473}$NTVWKQL[pS] SSVTGLT$^{487}$; SEQ ID NO: 32). The tissue sections were then incubated with species-specific secondary antibodies conjugated with oligonucleotides (PIA probes), followed by ligation and amplification reactions. The number of PLA signals for GLK–IQGAP1 complex or phosphorylated IQGAP1 per tissue (3.14 mm$^2$) was counted.

Chromatin Immunoprecipitation (ChIP) Assays.

Peripheral blood T cells of mice were cross-linked with 1% formaldehyde for 10 min at room temperature. The lysates were sonicated (3×9 sec) on ice to generate random DNA fragments (200-1,000 bp). The cell extracts were immunoprecipitated with 5 μg of anti-RORγt, anti-AhR, or anti-STAT3 antibodies plus protein G DYNABEADS™ (Invitrogen) for 4 h at 4° C. on a rotating wheel. After washing for 3 times, immunocomplexes between random DNA fragments (including IL-17A promoter fragments) and transcription factors (such as RORγt, AhR, or STAT3) were incubated at 94° C. for 15 min for reverse cross-linking, and then treated with protease K. The DNA fragments were purified using PCR purification kit and subjected to PCR for 35 cycles. The primers for the IL-17A promoter containing the RORγt-binding sites (−877~−872) and (−120~−115), AhR-binding site (−254~−249), STAT3-binding site (−150~−145), IRF4-binding site (−429~−421), KLF4-binding site (−1097~−1083), or BATF (−243 to −176) were. RORγt (−877 to −872), forward 5'-CT-GAAGAGCTGGGACCTAATG-3' (SEQ ID NO: 12), reverse 5'-GACTACTAACAGGAGGAGATG-3' (SEQ ID NO. 13), RORγt (−120 to −115), forward 5'-GGTTCTGTGCTGACCTCATTTGAG-3' (SEQ ID NO: 14), reverse 5'-CACAGATGAAGCTCTCCCTGG-3' (SEQ ID NO. 15); AhR, forward 5'-GAGACTCACAAACCAT-TACTATG-3 (SEQ ID NO: 16), reverse 5'-CACAGAT-GAAGCTCTCCCTGG-3' (SEQ ID NO: 17); STAT3, forward 5'-GAGACTCACAAACCATTACTATG-3' (SEQ ID NO: 18), reverse 5'-CACAGATGAAGCTCTCCCTGG-3' (SEQ ID NO; 19); IRF4, forward 5'-GGGCAAGG-GATGCTCTCTAG-3'(SEQ ID NO: 20), reverse 5'-CT-GAAGCTGCTGCAGAGCTG-3'(SEQ ID NO: 21); KLF4, forward: 5'-GGGTATTATCCCAAGGGTATCC-3'(SEQ ID NO: 22), reverse, 5'-ATGCAGCATGAGGTGGACCGAT-3' (SEQ ID NO: 23); BATF, forward: 5'-GAACTTCTGCCCTTCCCATCT-3' (SEQ ID NO: 24), reverse, 5'-CAGCACAGAACCACCCCTTT 3' (SEQ ID NO; 25).

Immunoprecipitation, GST/his Pulldown, and Immunoblotting Analyses.

Immunoprecipitation was performed by preincubation of 0.5-1 mg protein lysates with 1 μg antibody for 1 h at 4° C., followed by addition of 20 μl of protein A/G-SEPHAR-OSE® beads for 3 h. For GST- and His-pulldown assays, GST-tagged proteins and His-tagged proteins plus their interacting proteins were incubated for 3 h with glutathione-SEPHAROSE® beads and Ni-SEPHAROSE® beads, respectively. The immunocomplexes or GST/His-pulldown complexes were washed with lysis buffer (1.5 mM MgCl$_3$, 0.2% NP40, 125 mM NaCl, 5% glycerol, 25 mM NaF, 50 mM Tris-HCl, and 1 mM Na$_3$VO$_4$) three times at 4° C., followed by boiling in 5× loading buffer at 95° C. for 3 min. The immunoblotting analyses were performed.

In Vitro GLK Kinase Assays.

GLK kinase activity was determined by measuring the rate of ADP production in the in vitro kinase reaction using ADP-GLO™ Kinase Assay kit. For the kinase reaction, recombinant proteins of the GLK kinase-domain (1 μg) were incubated with recombinant proteins of kinase-dead PKCθ (K409W; 0.15 μg) plus ATP (0.1 mM) or myelin basic protein (MBP) plus ATP (0.1 mM) in kinase buffer (40 mM Tris-HCl, pH7.5.20 mM MgCl$_2$, 0.1 mg/ml BSA, 10 mM DTT and 0.1 mM Na$_3$VO$_4$) for 30 min at room temperature.

Cell-Based High-Throughput Screening and In Vitro Kinase Screening for GLK Inhibitors.

Cell-based high-throughput screening was conducted against a representative library of 100,000 molecules at ~10 μM. CHO-GLK-Luc cells expressing GLK and NF-κB-luciferase reporter were used. The reaction volume was 5 μl (500 cells) per well in 1,536-well plates. There was no positive control. This high-throughput screening campaign was successful with a determined Z' factor of 0.57~0.60. However, the cells are very sensitive, and the screening resulted in a total of 17,884 potential hits, which were picked, re-screened, and confirmed. At the end, 1,392 compounds were identified for high inhibition (>80%) of the GLK-induced NF-κB-luciferase activity of CHO-GLK-Luc cells. These 1,392 compounds were further screened for the inhibition of GLK kinase activity by in vitro kinase assays using the kinase-dead PKCθ protein as the substrate. From the screening, two potential small-molecule GLK inhibitors ($IC_{50}$<μM) were identified.

Besides the above 100,000 molecules, 1,200 compounds of an FDA-approved drug library were also tested using the same cell-based (>90% inhibition) and in vitro screening approaches. From both libraries (101,200 compounds), the most effective inhibitor is verteporfin (hereinafter also called C1), which is an FDA-approved drug for macular degeneration of eyes (Newman, 2016). The formula of verteporfin is $C_{41}H_{42}N_4O_8$. Verteporfin is a light-activated drug for the retinal treatments, whereas verteporfin (C1) was used without any photochemical process in this study.

Cell Transfections, T-Cell Stimulation, In Vitro Kinase Assays for PKCθ or IKKβ, and Flow Cytometry Analyses.

These experiments were performed as described previously.

Immunofluorescence and Confocal Imaging.

Cells were fixed in cold methanol for 2 min. After permeation with 0.25% Triton X-100 for 1 h, the cells were blocked with 5% bovine serum albumin (BSA) for 2 h. The cells were incubated with primary antibodies (1:200 dilution) for 24 h and then with secondary antibodies (1:500 dilution) for 2 h. The secondary antibodies donkey anti-rabbit IgG-Alexa Fluor 568 and goat anti-mouse IgG-Alexa Fluor 488 were purchased from Abcam and life technologies, respectively. The cover slides were mounted in FLUO-ROSHIELD™ with DAPI (GeneTex) and analysed using a Leica TCS SP5 confocal microscope.

In Vitro T-Cell Differentiation Assays.

$CD4^+$ splenic T cells were purified from mice. Cells ($5 \times 10^5$) were cultured in 1 ml RPMI medium in 48-well plates coated with anti-CD3 (2 μg/ml) and anti-CD28 (3 μg/ml) antibodies. For Th17 differentiation, splenic $CD4^+$ cells were cultured in the medium containing IL-23 recombinant proteins (50 ng/ml, R&D), IL-6 recombinant proteins (20 ng/ml, R&D), TGF-β recombinant proteins (5 ng/ml, R&D), anti-IL-4 (5 μg/ml, Biolegend), and anti-IFN-γ (5 μg/ml, Biolegend) antibodies. For Th1 differentiation, $CD4^+$ splenic cells were cultured in the medium containing IL-12 recombinant proteins (5 ng/ml, R&D) and anti-IL-4 antibodies (1 μg/ml, Biolegend).

Cell Migration Assays.

For primary cell migration assays, $2 \times 10^5$ cells in 200 ml of IMDM with 10% FBS were seeded into the upper chamber of transwells (8 μm pore size, Corning), and the lower chamber was loaded with 500 μm of IMDM with 20% FBS. For cancer cell migration assays, $5 \times 10^4$ cells in 200 μl of RPMI 1640 with 10% FBS were seeded into the upper chamber of transwells (8 μm pore size, Corning), and the lower chamber was loaded with 500 mm of RPMI 1640 with 10% FBS. After incubation at 37° C. for 24 h, cells migrating to the lower chamber were imaged and counted by bright-field microscopy following fixation with absolute methanol and staining with 1% crystal violet solution.

Liquid Chromatography-Mass Spectrometry.

After in vitro kinase assays, protein bands of Flag-tagged RORγt were collected from INSTANTBLUE™-stained SDS-PAGE gels. Proteins were digested with trypsin and subjected to LC-MS/MS analyses by LTQ-Orbitrap Elite hybrid mass spectrometer as described previously.

Statistical Analyses.

All experiments were repeated at least three times. Data are presented as mean±SEM. The statistical significance between two unpaired groups was analyzed using two-tailed Student's t-test. P values of less than 0.05 were considered statistically significant.

Cell cultures and various assays may be used in making and practice of the invention such as follows:

Cell-Based Assays:

drug screening using T cells of Lck-GLK transgenic mice, GLK-overexpressing T cells, or activated T cells determined by IL-17A ELISA, IL-17A transcription reporter assays, or immunoblotting.

Establish GLK-Overexpressing Stable Cells.

Jurkat cells were transfected with GLK plasmid and the 2-kb IL-17A promoter-driven firefly-luciferase reporter plasmid using Neon Transfection System (Invitrogen Corporation). To select GLK-overexpressing stable cells, cells were cultured in RPMI-1640 containing neomycin at least for 2 weeks.

IL-17A Enzyme-Linked Immunosorbent Assay.

T cells of Lck-GLK transgenic mice, GLK-overexpressing T cells, or TCR-activated T cells were incubated in RPMI medium (200 ml) for 72 h. The levels of IL-17A in the supernatants were determined by enzyme-linked immunosorbent assay (ELISA) for IL-17A.

Luciferase Reporter Assay for IL-17A Promoter Activity.

$10^6$ GLK-overexpressing stable Jurkat cells were resuspended in 60 μl RPMI medium plus 60 μl lysis/Luciferase buffers. Data represent the mean of firefly-luciferase activity with standard error of the mean (SEM) error bar.

RORγt Serine-489 Phosphorylation.

T cells of Lck-GLK transgenic mice, GLK-overexpressing T cells, or TCR-activated T cells were subjected to immunoblotting using the anti-phospho-RORγt [S489] antibody.

Protein-Protein Interaction Assays:

fluorescence resonance energy transfer (FRET) assays, amplified luminescent proximity homogeneous assays (AL-PHA; PerkinElmer), proximity ligation assay (PLA), and chromatin immunoprecipitation (ChIP) assays.

Fluorescence Resonance Energy Transfer (FRET) Assays.

HEK293T cells were co-transfected with CFP-AhR, YFP-RORγt, and IKKβ plasmids and the fluorescence intensities were detected using ENSPIRE™ 2300 Multilabel Reader 24 h later. The CFP was excited at 432 nm; the resulting fluorescence intensity emitted at 485 nm was measured. The YFP was excited at 485 nm; the resulting fluorescence intensity emitted at 540 nm was measured. The FRET signal was excited at 432 nm; the resulting fluorescence intensity emitted at 540 nm was measured.

Amplified Luminescent Proximity Homogeneous Assays (ALPHA).

The AlphaScreen binding assay was carried out in 384-well, white Proxiplates in a total volume of 20 μl. The AlphaScreen Flag detection kit was from PerkinElmer Life Science. The AlphaScreen donor beads were supplied as Flag-coated, and the acceptor beads were conjugated to an anti-Myc antibody. Flag-tagged AhR proteins and phosphorylated Myc-tagged RORγt proteins were mixed together in 384-well plates (5 μl/well). When using HEK293T transfectants (cells co-transfected with Flag-AhR, Myc-RORγt, and IKKβ plasmids), 0.2 μg lysates were added per well. For detecting GLK–IQGAP1 interaction, cells were co-transfected with Flag-GLK and Myc-IQGAP1. Acceptor beads (5 µl/well) were added and incubated for 30 min. Donor beads (5 µl/well) were subsequently added and incubated for 3 h before measuring with an EnVision multilabel reader (PerkinElmer life Science). The final concentration of donor and acceptor beads was 20 µg/ml. All dilutions were made in HEPES buffer (10 mM HEPES, 150 mM NaCl, 0.05% Tween-20, 0.5 mM DTT).

In Situ Proximity Ligation Assay (PLA).

T cells of Lck-GLK transgenic mice, GLK-overexpressing T cells, activated T cells or AhR+RORγt+IKKβ-overexpressing cells were used. PLA assays were performed using the DUOLINK® In Situ Red Starter kit according to the manufacturer's instructions. Briefly, cells were incubated with rabbit or mouse primary antibodies for each molecule pair (anti-AhR antibody+anti-RORγt antibody or anti-AhR antibody+anti-phospho-RORγt [Ser489] antibody), followed by species-specific secondary antibodies-conjugated with oligonucleotides (PLA probes). After ligation and amplification reactions, the PLA signals from each pair of PLA probes in close proximity (<nm) were visualized as individual red dots by a fluorescence or a confocal microscope. Each red dot represents for a direct interaction.

Co-Immunoprecipitation Assays.

HEK293T cells were co-transfected with Myc-AhR, Flag-RORγt, and IKKβ plasmids. For immunoprecipitation, cell extracts were incubated with anti-Flag agarose beads, or anti-Myc agarose beads in lysis buffer with continuous rotation at 4° C. for 2 h. The resultant immunoprecipitates were washed three times with lysis buffer and immunoblotted with the anti-Myc or anti-Flag.

Chromatin Immunoprecipitation (ChIP) Assays (For detecting RORγt binding to the AhR-binding site on the IL-17A promoter). T cells of Lck-GLK transgenic mice, GLK-overexpressing T cells, activated T cells, or AhR+RORγt+IKKβ-overexpressing cells were cross-linked with 1% formaldehyde for 10 min at room temperature. The lysates were sonicated (3×9 sec) on ice to generate 200-1,000 bp DNA fragments. The cell extracts were immunoprecipitated with 5 µg of anti-RORγt antibody plus protein G DYNABEADS™ for 4 h at 4° C. on a rotating wheel. After washing for 3 times, immunocomplexes were incubated at 94° C. for 15 min for reverse cross-linking, and then treated with protease K. The DNA fragments were purified using PCR purification kit and subjected to PCR for 35 cycles. The primers for the IL-17A promoter containing the AhR-binding site (−254−−249) were forward 5'-GAGACT-CACAAACCATTACTATG-3 (SEQ ID NO: 26), reverse 5'-CACAGATGAAGCTCTCCCTGG-3' (SEQ ID NO: 27).

Results

Lck-GLK Transgenic Mice Develop Autoimmune Diseases Through IL-17A

To study the consequence of GLK overexpression in vivo, we generated T-cell-specific GLK transgenic (Lck-GLK Tg) mice. Lck-GLK Tg mice displayed normal development of T cells and B cells; however, the mice displayed paralyses of the hind-limb and tail, clouding of the eye, or symptoms of proctitis and dermatitis between 8 and 16 weeks of age. Lck-GLK Tg mice also showed hepatosplenomegaly and enlargements of lymph nodes and kidneys. Histology staining showed the induction of pneumonia, nephritis, and spleen abnormality in these mice (FIG. 1A). Induction of serum autoantibodies in Lck-GLK Tg mice (FIG. 1B) also suggests the development of autoimmune responses in these mice. To study which proinflammatory cytokines contribute to autoimmune diseases in Lck-GLK Tg mice, the serum cytokines were determined by ELISA. Surprisingly, only IL-17A was selectively induced in the sera of 4-week-old Lck-GLK Tg mice (FIG. 1C), whereas the proinflammatory cytokines IFN-γ and TNF-α were not induced. Consistently, in vitro Th17 differentiation of Lck-GLK Tg T cell was increased compared to that of wild-type T cell, whereas in vitro Th1 differentiation of Lck-GLK Tg T cell was unaffected. Moreover, IL-17A production was induced in unstimulated T cells of Lck-GLK Tg mice compared to that of wild-type mice. To rule out the potential position effect of the transgene, the second Lck-GLK Tg mouse line (Lck-GLK #2) was also characterized. The second line of Lck-GLK Tg mice also displayed GLK overexpression in T cells and induction of serum IL-17A levels. These data suggest that GLK overexpression in T cells induces IL-17A production in mice.

To demonstrate that pathogenic role of IL-17A in Lck-GLK Tg mice, Lck-GLK Tg mice were bred with IL-17A-deficient mice. GLK-induced serum IL-17A levels were significantly decreased by IL-17A deficiency, while other inflammatory cytokine levels were unaffected. Moreover, the autoantibodies levels were also significantly reduced in Lck-GLK Tg/IL-17A-deficient mice compared to those in Lck-GLK Tg mice (FIG. 1D). Lck-GLK Tg/IL-17A-deficient mice displayed reduction of infiltrating inflammatory cells in the kidneys, the liver, and the lung, while showing normal distribution of white pulp and red pulp in the spleen, compared to those in Lck-GLK Tg mice. The data suggest that IL-17A contributes to autoimmune responses in Lck-GLK Tg mice. To further demonstrate that the induction of IL-17A is due to GLK overexpression, we treated Lck-GLK T cells with GLK shRNA. The IL-17A overproduction was abolished by GLK shRNA knockdown in T cells purified from Lck-GLK Tg mice (FIG. 1E). These results demonstrate that GLK overexpression induces IL-17A overproduction and subsequent autoimmune phenotypes in mice.

GLK Induces IL-17A Transcription Through Activating AhR and RORγt

Figure 2:
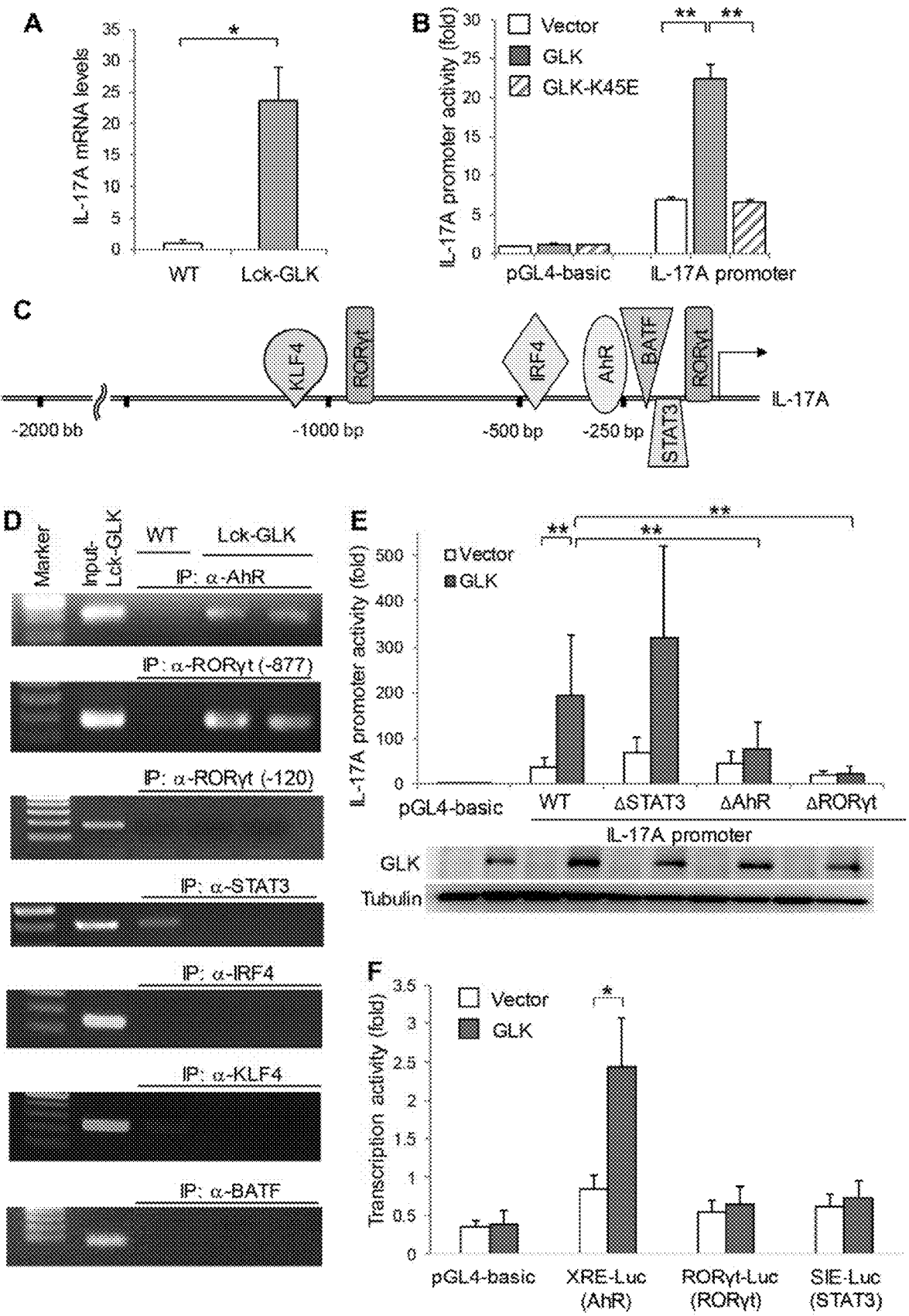
FIG. 2 shows that GLK enhances IL-17A expression through inducing AhR and RORγt. (A) Murine IL-17A mRNA levels in peripheral blood T cells from mice were analyzed by real-time PCR. The expression levels of IL-17A were normalized to Mrpl32 levels. The fold changes are presented relative to the value of wild-type mice. Means±SEM are shown. (B) Luciferase reporter activity of the IL-17A promoter. Jurkat T cells were co-transfected with the plasmid encoding GLK or GLK kinase-dead (GLK-K45E) mutant plus the IL-17A promoter (2 kb) construct. Means±SEM are shown. (C) Schematic diagram of transcription factors on the IL-17A promoter. (D) The binding of AhR, RORγt, STAT3, IRF4, KLF4, or BATF to the IL-17A promoter in T cells from mice was analyzed by ChIP-PCR using immunocomplexes from individual immunoprecipitation experiments. (E) Luciferase reporter activity of the IL-17A mutant promoters. Jurkat T cells were co-transfected with empty vector or GLK plasmid plus the IL-17A promoter construct containing a mutated binding element for AhR, RORγt (−877), or STAT3. (F) Luciferase reporter activity of AhR, RORγt (−877), and STAT3 response element (XRE-Luc, RORγt-Luc, and SIE-Luc) in Jurkat T cells co-transfected with empty vector or plasmid encoding GLK. XRE, xenobiotic responsive element; SE, sis-inducible element. WT, wild-type littermate controls; Lck-GLK, T-cell-specific GLK transgenic mice. Means±SEM of three independent experiments are shown (b), (e), and (f). *, P value<0.05; **, P value<0.01 (two-tailed Student's t-test).

The levels of IL-23 receptor and phosphorylated STAT3 were not increased in T cells of Lck-GLK Tg mice, suggesting that IL-17A overexpression is not due to enhancement of IL-23 signaling or IL-6/STAT3 signaling. Consistent with the IL-17A protein levels, mRNA levels of IL-17A were significantly increased in the purified T cells of Lck-GLK Tg mice compared to those of wild-type mice (FIG. 2A). We studied whether IL-17A overexpression is due to transcriptional activation of the IL-17A promoter. IL-17A promoter activities in Jurkat T cells were enhanced by GLK overexpression but not by GLK kinase-dead (K45E) mutant (FIG. 2B). Next, the bindings of individual IL-17A transcription factors to the IL-17A promoter were studied (FIGS. 2C-D). Chromatin immunoprecipitation (ChIP) analyses showed that bindings of AhR and RORγt (−877) to the IL-17A promoter were induced in T cells of Lck-GLK Tg mice (FIG. 2D), whereas bindings of STAT3, IRF4, KLF4, and BATF to the IL-17A promoter were not enhanced (FIG. 2D). Interestingly, the binding of RORγt to the −120 region of the IL-17A promoter was not significantly induced (FIG. 2D); similar findings were reported by others (Jain et al., 2016; Zhang et al., 2008). Consistent with ChIP data, the GLK-enhanced IL-17A reporter activity was abolished by mutation of the AhR-binding element or the RORγt-binding site (−877), whereas the GLK-induced IL-17A reporter activity was unaffected by mutation of the STAT3-binding site (FIG. 2E) or the RORγt (−120)-binding site. Notably, AhR response element-driven reporter (XRE-Luc) activity was induced by GLK overexpression (FIG. 2F), whereas RORγt (−877) or STAT3 response element-driven reporter (RORγt-Luc or SIE-Luc) activity was unaffected (FIG. 2F). These results suggest that GLK signaling induces IL-17A transcription through activating AhR and maybe RORγt.

GLK Controls IL-17A Production and Autoimmune Responses Through AhR

Figure 3:
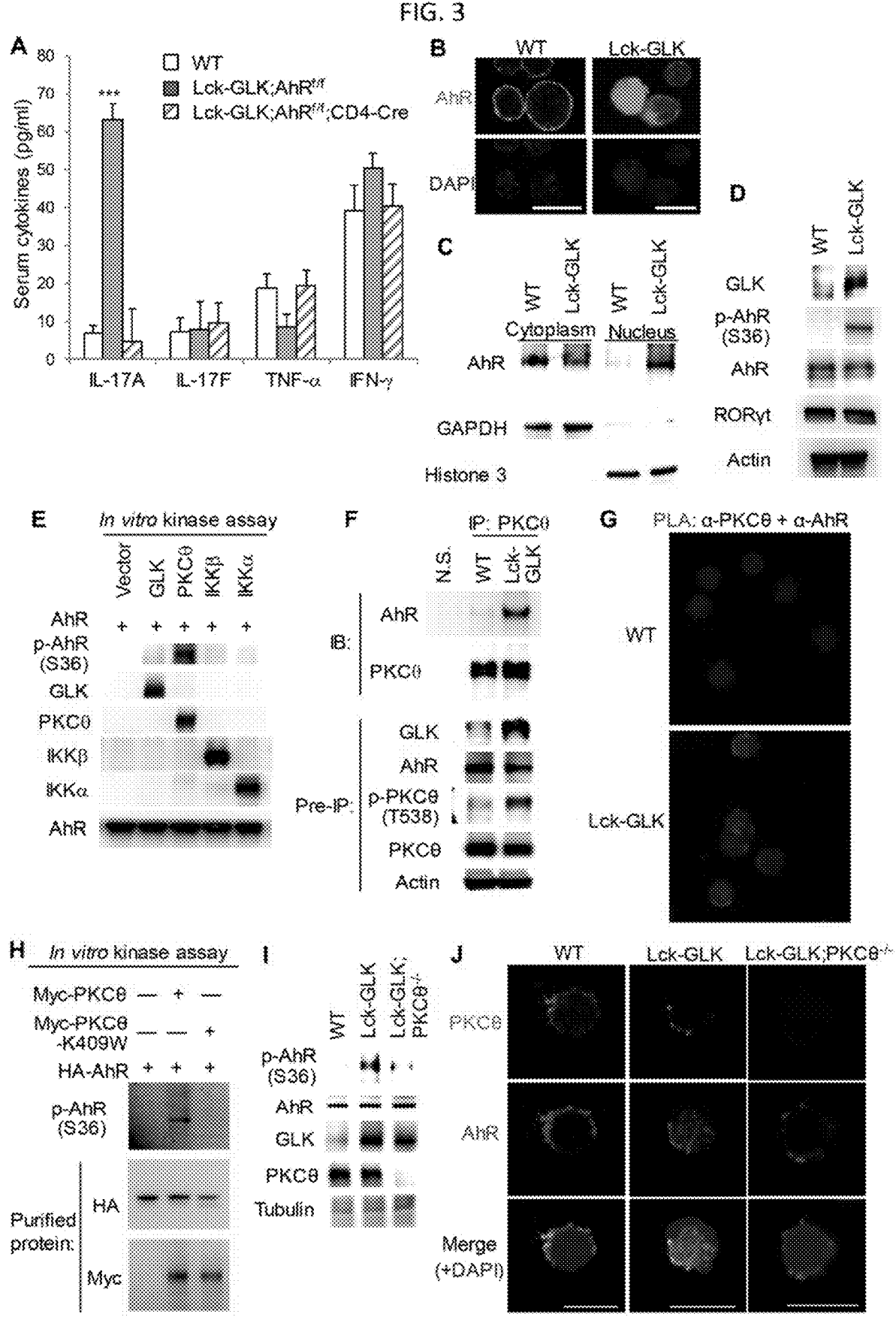
FIG. 3 shows that PKCθ phosphorylates AhR and induces its nuclear translocation. (A) The serum levels of cytokines from indicated mice were determined by ELISA assays. Means±SEM are shown. WT, wild-type littermate controls; Lck-GLK, T-cell-specific GLK transgenic mice. Lck-GLK; AhR$^{f/f}$;CD4-Cre, T-cell-specific GLK transgenic mice bred with AhR conditional knockout (cKO) mice. *, P value<0.05; **, P value<0.01 (two-tailed Student's t-test). (B) Confocal microscopy of subcellular localization of AhR in murine splenic T cells without stimulation. Original magnification, ×630; bar, 10 μm. (C) Immunoblotting of AhR, GAPDH, and histone 3 in cytoplasmic and nuclear fractions of primary splenic T cells from WT and Lck-GLK Tg mice. (D) Immunoblotting of p-AhR (Ser-36), AhR, and GLK in primary splenic T cells of WT and Lck-GLK Tg mice. (E) Immunoblotting of AhR phosphorylation and indicated kinases in in vitro kinase assays using Flag-GLK, Flag-PKCθ, Flag-IKKβ, Flag-IKKα, and HA-AhR (as the substrate) isolated from individually transfected HEK293T cells. (F) Co-immunoprecipitations (co-IP) of endogenous AhR with PKCθ from lysates of primary splenic T cells from WT and Lck-GLK mice without stimulation. (G) PLA of interaction between endogenous PKCθ and AhR in peripheral blood T cells from wild-type or Lck-GLK Tg mice. Each red dot represents for a direct interaction. T-cell nucleus was stained with DAPI (blue color). (H) In vitro kinase assays of purified HA-tagged AhR plus either Myc-tagged PKCθ WT or PKCθ kinase-dead (K409W) mutant proteins. (I) Immunoblotting analyses of phosphorylated AhR (Ser-36), AhR, GLK, and PKCθ in primary splenic T cells of WT, Lck-GLK Tg and Lck-GLK Tg mice bred with PKCθ KO mice. (J) Confocal microscopy of subcellular localization of AhR and PKCθ in primary splenic T cells of indicated mice. Original magnification, ×630; bar, 10 μm. WT, wild-type littermate controls; Lck-GLK, T-cell-specific GLK transgenic mice; Lck-GLK; PKCθ$^{-/-}$, Lck-GLK transgenic mice bred with PKCθ knockout mice.

To further demonstrate the role of AhR in promoting IL-17A production in Lck-GLK Tg mice, we bred Lck-GLK Tg mice with T-cell-specific AhR knockout (AhR cKO: AhR$^{f/f}$;CD4-Cre) mice. Serum IL-17A levels were drastically reduced in Lck-GLK/T-AhR cKO (Lck-GLK;AhR$^{f/f}$; CD4-Cre) mice, whereas serum TNF-α and IFN-γ levels were unaffected by AhR deficiency (FIG. 3A). Levels of anti-nuclear antibody (ANA), anti-dsDNA antibody, and rheumatoid factor (RF) were also decreased in Lck-GLK/ AhR cKO mice compared to those in Lck-GLK Tg mice (Chuang Huai-Chia et al. "MAP4K3/GLK promotes lung cancer metastasis by phosphorylating and activating IQGAP1" *Cancer Research*, 2019). Histology staining showed that induction of nephritis and spleen abnormality in Lck-GLK Tg mice was abolished by AhR knockout. Infiltration of inflammatory immune cells in the liver of Lck-GLK Tg mice was also suppressed by AhR knockout. The data indicate that AhR plays a critical role in the IL-17A overproduction and autoimmune responses in Lck-GLK Tg mice.

PKCθ Phosphorylates AhR at Ser-36 and Induces AhR Nuclear Translocation

The confocal images (using two different anti-AhR antibodies; FIG. 3B) and subcellular fractionation experiments (FIG. 3C) showed that AhR nuclear translocation was enhanced in T cells of Lck-GLK Tg mice. In addition, we examined whether GLK signaling induces AhR nuclear translocation through enhancing phosphorylation of AhR. There is only one commercial anti-phospho-AhR antibody, which detects phospho-Ser-36 AhR; however, the role of Ser-36 phosphorylation in AhR nuclear translocation has not been demonstrated. Interestingly, immunoblotting analyses using the anti-phospho-AhR antibody for AhR phosphorylation showed that AhR Ser-36 phosphorylation was enhanced in T cells of Lck-GLK Tg mice, as well as in anti-CD3-stimulated T cells (FIG. 3D). These data suggest that GLK overexpression (and TCR signaling) may induce AhR activity through enhancing AhR Ser-36 phosphorylation and nuclear translocation in T cells.

We studied which kinase is responsible for phosphorylation and nuclear translocation of AhR in T cells of GLK Tg mice. SGK1 can stabilize Th17 population (Wu et al., 2013). The basal or TCR-induced SGK1 activation was unchanged in Lck-GLK T cells, suggesting that SGK1 is not involved in GLK-induced AhR phosphorylation. GLK signaling in T cells induces kinase activities of PKCθ, IKKα, and IKKβ. To determine which kinase phosphorylates AhR, GLK, PKCθ, IKKα, IKKβ, and AhR were each immunoprecipitated from individually transfected HEK293T cells and subjected to in vitro kinase assays. The data showed that AhR Ser-36 phosphorylation was drastically induced by PKCθ in vitro (FIG. 3E). The specificity of the antibody for AhR Ser-36 phosphorylation was confirmed using a wild-type AhR or a S36A mutant transfectant by immunoblotting. Immunofluorescence and confocal imaging analyses showed that PKCθ overexpression enhanced AhR nuclear translocation in Jurkat T cells and HEK293T cells, whereas AhR-S36A mutation stayed in the cytoplasm even in PKCθ-overexpressing cells. The data indicate that PKCθ-mediated Ser-36 phosphorylation of AhR stimulates AhR nuclear translocation. The interaction between PKCθ and AhR was induced in purified T cells of Lck-GLK Tg mice (FIG. 3F). Moreover, the protein-protein interaction/ALPHA technology assays showed an interaction (<200 nm) between PKCθ and AhR, but not between GLK and AhR. Furthermore, the fluorescence resonance energy transfer (FRET) analysis showed a direct interaction (1-10 nm) between PKCθ and AhR in PKCθ/AhR co-transfected Jurkat T cells. To study the subcellular localization and protein interaction (<40 nm) in vivo, we performed in situ proximity ligation assay (PLA) using probes corresponding to PKCθ and AhR. The PLA data showed strong signals in the cytoplasm of T cells from Lck-GLK Tg mice (FIG. 3G). In situ PLA using probes corresponding to Myc and Flag tags showed similar results in Myc-PKCθ and Flag-AhR-overexpressing HEK293T cells. In vitro binding assays with purified PKCθ and AhR proteins further confirmed this direct interaction. Furthermore, purified PKCθ indeed phosphorylated AhR at Ser-36, whereas purified kinase-dead (K409W) mutant of PKCθ did not (FIG. 3H). These data demonstrate that PKCθ directly interacts with and phosphorylates AhR at Ser-36, leading to AhR nuclear translocation.

To verify the role of PKCθ in AhR nuclear translocation and its in vivo function, we generated PKCθ knockout (KO) mice using TALEN technology. Lck-GLK Tg mice were then bred with PKCθ KO mice to generate Lck-GLK; PKCθ$^{-/-}$ mice. As expected, GLK-induced AhR Ser-36 phosphorylation in T cells was abolished by PKCθ knockout (FIG. 3I). Immunofluorescence and confocal imaging analyses showed that AhR was detected abundantly in the nucleus of T cells from Lck-GLK Tg mice (FIG. 3J). In contrast, AhR expression was detected in the cytoplasm, but not in the nucleus, of T cells from wild-type and Lck-GLK transgenic/ PKCθknockout (Lck-GLK;PKCθ$^{-/-}$) mice (FIG. 3J). The serum levels of IL-17A and autoantibodies were significantly decreased in Lck-GLK;PKCθ$^{-/-}$ mice compared to those in Lck-GLK Tg mice. Moreover, the inflammatory phenotypes were abolished in Lck-GLK transgenic/PKCθ knockout mice. Taken together, these results indicate that GLK induces IL-17A production through activating PKCθ-AhR signaling in T cells.

AhR Interacts with RORγt and Transports RORγt into the Nucleus

Figure 4:
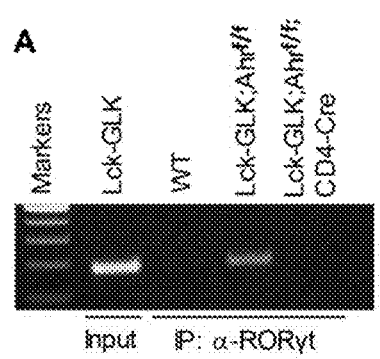
FIG. 4 shows that GLK induces RORγt binding to the IL-17A promoter through AhR and RORγt interaction. (A) The bindings of RORγt to the IL-17A promoter in T cells from indicated mice were analyzed by ChIP-PCR. (B) Co-immunoprecipitations (co-IP) of endogenous AhR with RORγt using lysates of primary splenic T cells from WT and Lck-GLK mice without any stimulation. (C) Confocal microscopy of subcellular localization of AhR and RORγt in primary T cells of indicated mice. Original magnification, ×630; bar, 10 μm. (D) The bindings of AhR and RORγt to the IL-17A promoter in T cells from mice were analyzed by ChIP-PCR using anti-RORγt immunocomplexes. (E) Confocal microscopy of proximity ligation assays (PLA) for the interaction between endogenous AhR and RORγt in peripheral blood T cells from indicated mice. (F) Co-immunoprecipitation (IP) of HA-tagged AhR and Flag-tagged RORγt using lysates of HEK293T cells co-transfected with GLK-CFP, PKCθ-Myc, IKKβ-CFP, or IKKα-Myc plasmid. (G) GST-pulldown assays of purified Flag-tagged RORγt and GST-tagged AhR proteins. Flag-tagged RORγt proteins were eluted with Flag peptides using lysates of HEK293T cells co-transfected with Flag-RORγt plus either CFP-IKKβ or vector. Original magnification, ×630; bar, 10 μm.
Figure 4:
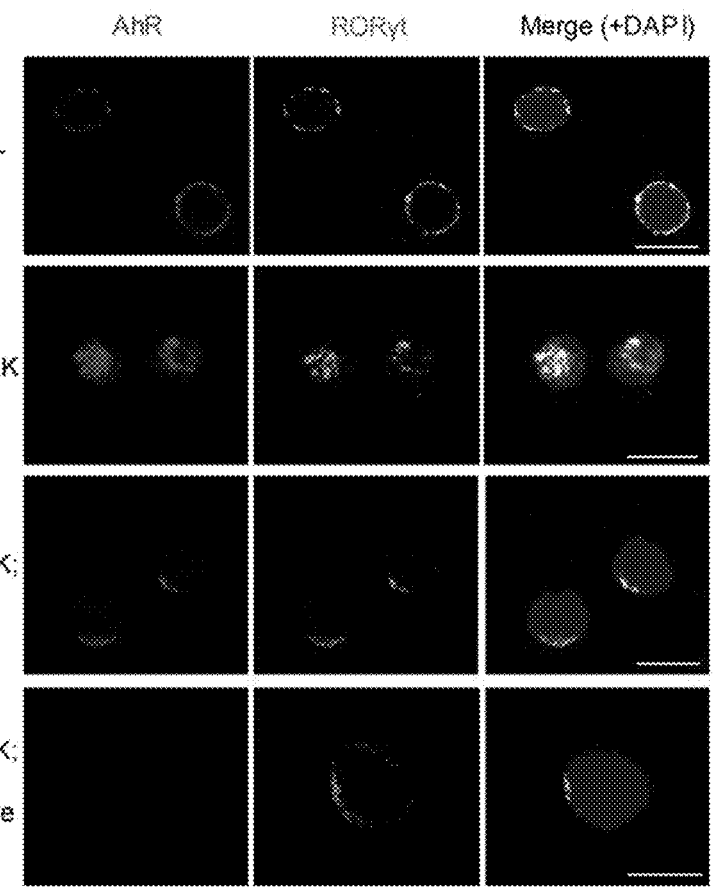
Figure 4:
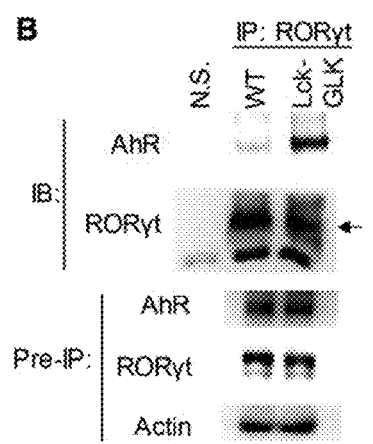
Figure 4:
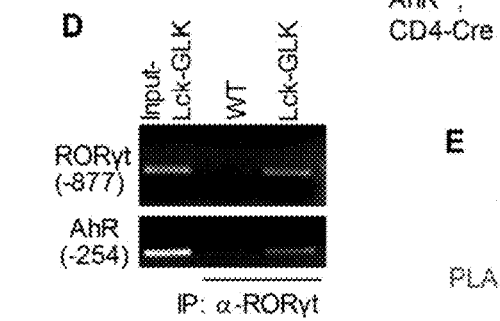
Figure 4:
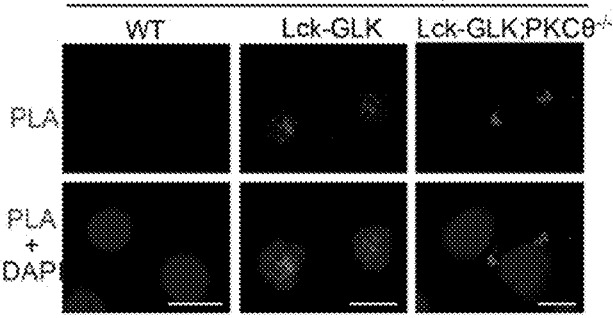
Figure 4:
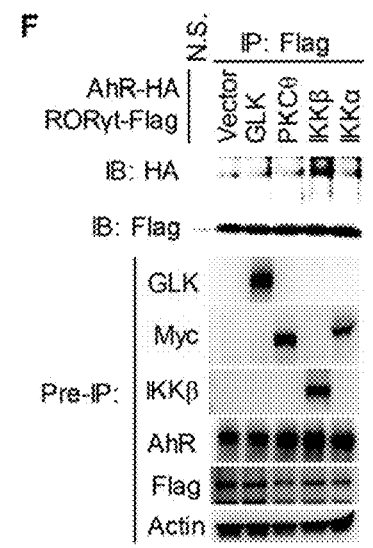
Figure 4:
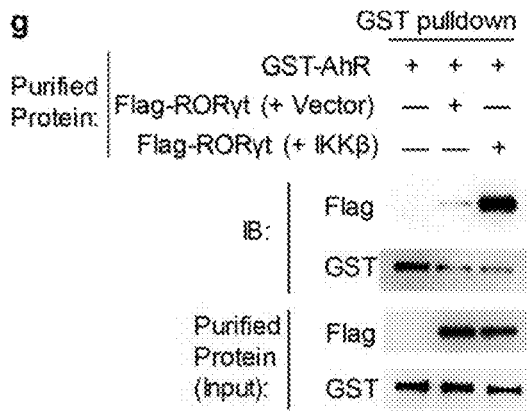

Paradoxically, both AhR-binding and RORγt-binding elements are required for the GLK-induced IL-17A reporter activity (FIG. 2E); however, GLK induced the activity of AhR, but not RORγt, response element (FIG. 2F). We suspected that AhR may facilitate induction of RORγt activity. We first studied whether GLK induces RORγt binding to the IL-17A promoter through AhR. Chromatin immunoprecipitation (ChIP) data indeed showed that the GLK-induced RORγt binding to the IL-17A promoter was abolished in AhR knockout T cells (FIG. 4A). The data suggest that AhR facilitates the binding of RORγt to the IL-17A promoter. Next, we studied whether AhR interacts with RORγt. The interaction between endogenous AhR and RORγt was drastically enhanced in T cells of Lck-GLK Tg mice (FIG. 4B). Confocal imaging analyses showed a co-localization of AhR and RORγt in the nucleus of T cells from Lck-GLK Tg mice (FIG. 4C). ChIP analyses using an anti-RORγt antibody also showed the binding of RORγt to the AhR-binding element of the IL-17A promoter in T cells of Lck-GLK mice (FIG. 4D), suggesting that RORγt binds to the AhR-binding element through the AhR-RORγt complex formation. Moreover, in situ proximity ligation assay (PLA) with probes corresponding to AhR and RORγt showed strong interaction signals in the nucleus of T cells from Lck-GLK Tg mice than those from wild-type mice (FIG. 4E). These data indicate a direct interaction between AhR and RORγt in the nucleus of T cells from Lck-GLK Tg mice. In addition, similar to AhR nuclear translocation, GLK-induced RORγt nuclear translocation was abolished by PKCθ knockout (FIG. 4C). The data support that PKCθ-phosphorylated AhR recruits RORγt into the nucleus. AhR-mediated RORγt nuclear translocation is further confirmed by AhR knockout; RORγt localized exclusively in the cytoplasm in T cells of Lck-GLK;AhR$^{f/f}$;CD4-Cre mice even in the presence of functional PKCθ (FIG. 4C, bottom panel). Thus, this result rules out the possibility that PKCθ directly regulates RORγt nuclear translocation. Collectively, these results indicate that AhR directly interacts with and transports RORγt into the nucleus in GLK-overexpressing T cells.

AhR-RORγt Interaction is Induced by IKKβ-Mediated RORγt Ser-489 Phosphorylation

Figure 5:
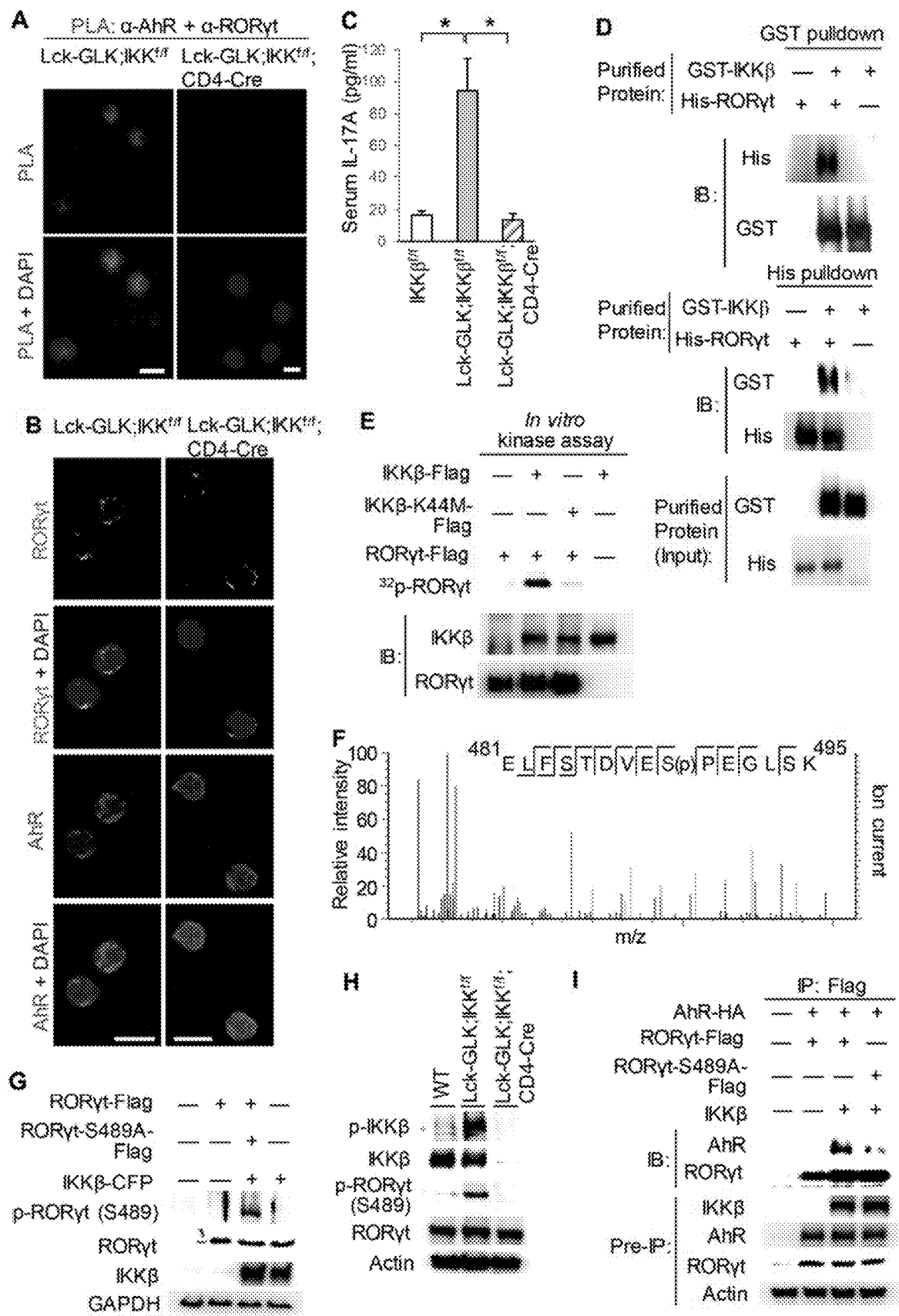
FIG. 5 shows that IKKβ phosphorylates RORγt Ser-489 leading to RORγt binding to AhR. (A) Confocal microscopy analyses of PLA for the interaction between endogenous AhR and RORγt in peripheral blood T cells from wild-type, Lck-GLK Tg, and Lck-GLK; tKKβ$^{f/f}$;CD4-Cre mice. (B) Confocal microscopy of subcellular localization of AhR and RORγt in primary splenic T cells of wild-type, Lck-GLK Tg, and Lck-GLK;IKKβ$^{f/f}$;CD4-Cre mice. Original magnification, ×630; bar, 10 μm. (C) The serum levels of cytokines in mice were determined by ELISA assays. Means±SEM are shown. *, P value<0.05 (two-tailed Student's t-test). (D) Direct interaction between recombinant proteins of RORγt and IKKβ. GST- or His-pulldown assays of purified His-tagged RORγt and GST-tagged IKKβ proteins. (E) In vitro kinase assays of immunoprecipitated Flag-tagged RORγt and either IKKβ or IKKβ kinase-dead (K44M) mutant proteins from individual HEK293T transfectants. (F) Mass spectrometry (MS)/MS fragmentation spectra of the tryptic peptides of RORγt contain the phosphorylation of Ser-489. (G) Antibody specificity of anti-phospho-RORγt (Ser-489) was demonstrated by immunoblotting using HEK293T cells co-transfected with CFP-tagged IKKβ plus either Flag-tagged RORγt WT or RORγt-S489A mutant. (H) Immunoblotting of p-RORγt (Ser-489), RORγt, p-IKKβ (Ser-180/181), and IKKβ in primary splenic T cells of indicated mice. (I) Co-immunoprecipitation (co-IP) of HA-tagged AhR and either Flag-tagged RORγt WT or RORγt-S489A mutant using lysates of HEK293T cells co-transfected with vector or IKKβ-CFP plasmid. WT, wild-type littermate controls; Lck-GLK, T-cell-specific GLK transgenic mice. Lck-GLK; IKKβ$^{f/f}$;CD4-Cre, T-cell-specific GLK transgenic mice bred with IKKβ conditional knockout mice. Original magnification, ×630; bar, 10 μm.

Surprisingly, in situ proximity ligation assay (PLA) showed an interaction between AhR and RORγt even in the cytoplasm of Lck-GLK;PKCθ$^{-/-}$ T cells (FIG. 4E). This result suggests that the interaction between AhR and RORγt is not regulated by AhR phosphorylation. The interaction between AhR and RORγt is still detectable in Lck-GLK; PKCθ$^{-/-}$ T cells (FIG. 4E); this result may be due to a compensatory signaling event in PKCθ knockout mice. To identify the kinase that stimulates the interaction between AhR and RORγt, we initially tested the potential role of GLK, IKKα, or IKKβ in the induction of AhR-RORγt interaction. The kinase GLK, PKCθ, IKKα, or IKKβ was co-transfected with AhR plus RORγt into HEK293T cells, followed by co-immunoprecipitation assays. The data showed that IKKβ overexpression enhanced the interaction between AhR and RORγt, whereas overexpression of GLK, PKCθ, and IKKα did not (FIG. 4F). Next, we tested whether IKKβ stimulates RORγt phosphorylation, which then induces the interaction of RORγt with AhR. Flag-tagged RORγt was purified from HEK293T cells co-transfected with RORγt plus either IKKβ or vector. GST-pulldown assays showed that purified GST-tagged AhR recombinant proteins strongly interacted with the purified RORγt proteins from RORγt plus IKKβ-co-transfected cells (FIG. 4G). The data suggest that IKKβ stimulates a direct interaction between AhR and RORγt through inducing RORγt phosphorylation. Conversely, PLA data showed that the GLK-induced interaction between AhR and RORγt in T cells of Lck-GLK Tg mice was abolished by IKKβ knockout (FIG. 5A). In addition, confocal imaging analyses showed that IKKβ knockout specifically abolished nuclear translocation of RORγt, but not AhR, in GLK transgenic T cells (FIG. 5B). Consistently, serum IL-17A levels were also decreased in Lck-GLK;IKKβ$^{f/f}$;CD4-Cre mice compared to those in Lck-GLK Tg mice (FIG. 5C). Next, we studied whether IKKβ directly interacts with RORγt. GST-pulldown and His-pulldown assays using purified recombinant GST-tagged IKKβ and His-tagged RORγt proteins showed a direct interaction between IKKβ and RORγt (FIG. 5D).

To study whether IKKβ phosphorylates RORγt, Flag-tagged RORγt, IKKβ, and IKKβ kinase-dead (K44M) mutant were individually immunoprecipitated from HEK293T transfectants and then subjected to in vitro kinase assays. The data showed that RORγt phosphorylation was induced in vitro by IKKβ, but not by IKKβ-K44M mutant (FIG. 5E). To identify the IKKβ-targeted RORγt phosphorylation site, in vitro phosphorylated Flag-tagged RORγt was isolated, followed by mass spectrometry analyses. Ser-489 was identified as the RORγt phosphorylation site by IKKβ (FIG. 5F). To demonstrate the phosphorylation of RORγt Ser-489 site, we generated an anti-phospho-RORγt (Ser-489) antibody, which specifically recognized RORγt WT but not S489A mutant when co-transfected with IKKβ (FIG. 5G). Immunoblotting using this phospho-antibody showed that RORγt Ser-489 phosphorylation was induced in T cells of Lck-GLK Tg mice, and the phosphorylation was abolished by IKKβ knockout (FIG. 5H). Consistently, RORγt-S489A mutant failed to interact with AhR under IKKβ overexpression (FIG. 5I). Taken together, in GLK-overexpressing T cells, IKKβ phosphorylates RORγt at Ser-489 and induces its interaction with AhR, which then transports RORγt into the nucleus and cooperates with RORγt to stimulate IL-17A transcription.

Figure 6:
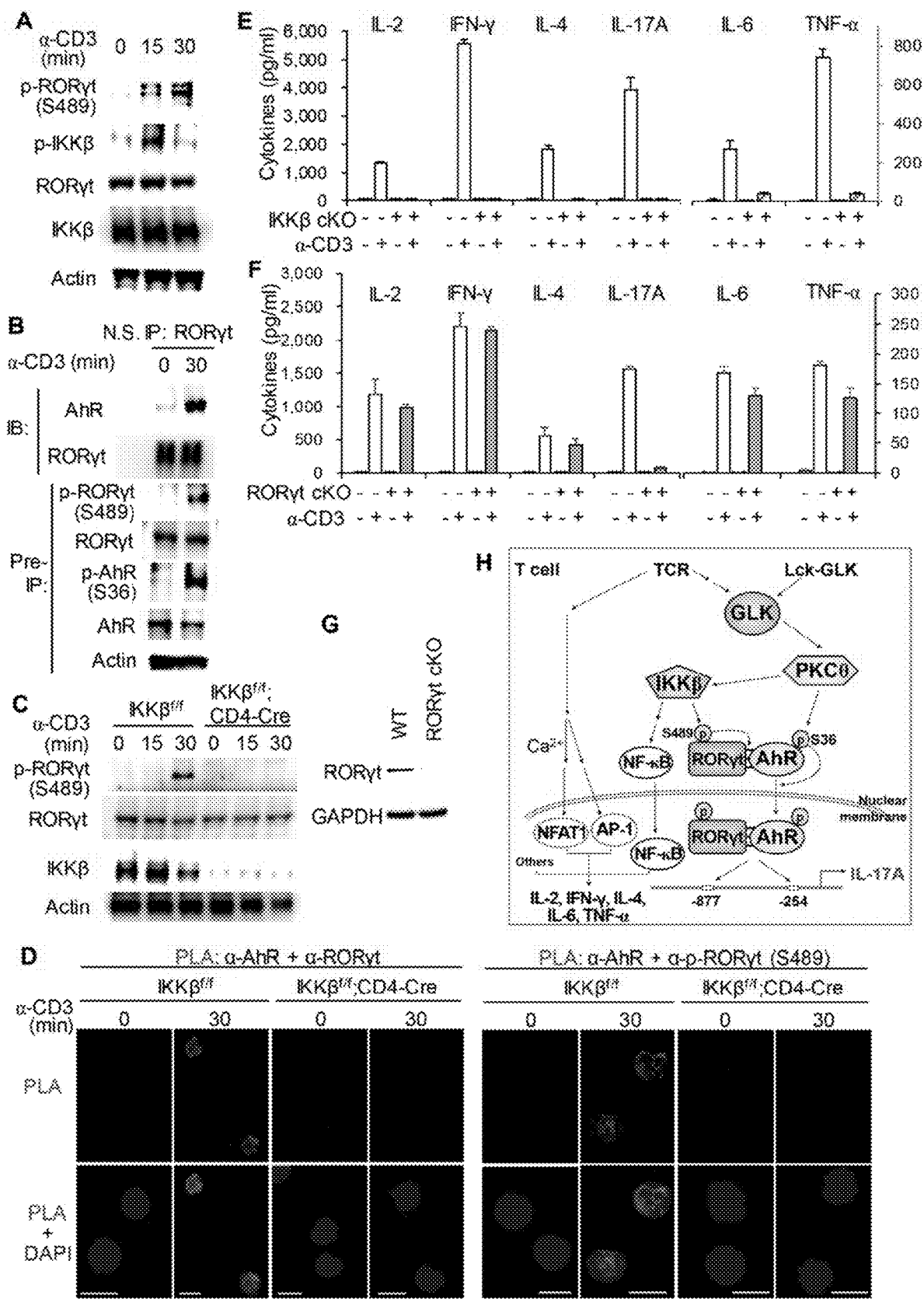
FIG. 6 shows that TCR signaling induces RORγt phosphorylation and subsequent AhR-RORγt interaction. (A) Immunoblotting of p-RORγt (Ser-489), RORγt, p-IKKβ (Ser-180/181), and IKKβ in primary splenic T cells. T cells were stimulated with anti-CD3 antibodies plus streptavidin. (B) Co-immunoprecipitations (co-IP) of endogenous AhR with RORγt from lysates of murine primary splenic T cells stimulated with anti-CD3 antibodies plus streptavidin. (C) Immunoblotting of p-RORγt (Ser-489), RORγt, and IKKβ in primary splenic T cells of IKKβ $^{OT}$ or CD4-Cre;IKKβ$^{f/f}$ mice. T cells were stimulated with anti-CD3 antibodies plus streptavidin. (D) Confocal microscopy of proximity ligation assays (PLA) for the interaction between endogenous AhR and RORγt (left panel) or between AhR and Ser-489-phosphorylated RORγt (right panel) in primary T cells of indicated mice. T cells were stimulated as (C). Original magnification, ×630; bar, 10 μm. (E and F) ELISA of various cytokines in supernatants of primary splenic T cells from indicated mice. T cells were stimulated with plate-bound anti-CD3 antibodies for 3 days. Means±SD are shown. (G) Immunoblotting of RORγt and GAPDH proteins from primary splenic T cells of indicated mice. (H) Schematic model of IL-17A transcription induced by the AhR-RORγt complex in GLK-overexpressing or TCR-stimulated T cells. GLK overexpression in T cells of T-cell-specific GLK transgenic (Lck-GLK Tg) mice induces AhR Ser-36 phosphorylation through PKCθ and also induces RORγt Ser-489 phosphorylation through IKKβ. Once RORγt is phosphorylated, RORγt directly interacts with AhR. Phosphorylated AhR is responsible for transporting RORγt into cell nucleus. The AhR-RORγt complex binds to both the RORγt-binding element (−877 to −872) and the AhR-binding element (−254 to −249) of the IL-17A promoter, leading to induction of IL-17A transcription. In normal T cells, T-cell receptor (TCR) stimulation also induces GLK kinase activity and downstream signaling, including IKKβ activation, RORγt Ser-489 phosphorylation, and the AhR-RORγt interaction. Besides NF-κB, other critical transcription factors (such as NFAT1 or AP-1) are also required for the transcriptional activation of IL-2, IFN-γ, IL-4, IL-6, and TNF-α in T cells. "Others" denotes other critical transcription factors. NF-κB is required for TCR-induced production of multiple cytokines; however, the GLK–IKKβ-NF-κB cascade alone is not sufficient for induction of multiple cytokines. Collectively, GLK overexpression or TCR signaling induces TL-17A transcription through AhR and RORγt in T cells.

Phosphorylated RORγt Interacts with AhR in TCR-Induced or Human Autoimmune T Cells We asked whether phosphorylated RORγt-mediated AhR-RORγt interaction is also induced by TCR signaling. We found that following IKKβ activation, RORγt Ser-489 phosphorylation in murine T cells was indeed induced by anti-CD3 stimulation (FIG. 6A). Moreover, co-immunoprecipitation assay and PLA showed that the interaction between endogenous RORγt and AhR was induced by TCR signaling (FIG. 6B). The interaction between AhR and Ser-489-phosphorylated RORγt was also stimulated by TCR signaling. Conversely, the TCR-induced RORγt Ser-489 phosphorylation (FIG. 6C) and the AhR-RORγt interaction (FIG. 6D) in T cells were abolished by IKKβ conditional knockout. These data suggest that IKKβ-mediated RORγt phosphorylation and subsequent AhR-RORγt interaction are induced during T-cell activation. To study whether IKKβ-mediated RORγt phosphorylation indeed regulates IL-17A production after TCR stimulation, secreted cytokines from anti-CD3-stimulated T cells were determined by ELISA. Consistent with previous reports (Gomez-Rodriguez et al., 2009; Liu et al., 2005), TCR signaling induced IL-17A production in T cells (FIGS. 6E-F). The TCR-induced IL-17A production in T cells was abolished by IKKβ conditional knockout (FIG. 6E), supporting that TCR-activated IKKβ induces IL-17A production in normal T cells. As expected, TCR-induced levels of several IKKβ/NF-κB-mediated cytokines (IL-2, IFN-γ, IL-4, IL-6, and TNF-α) were also reduced in T cells of IKKβ conditional knockout mice (FIG. 6E). To further verify the IKKβ-RORγt-IL-17A pathway, primary splenic T cells from T-cell-specific RORγt conditional knockout mice were used. Unlike IKKβ conditional knockout, RORγt conditional knockout only abolished IL-17A production upon TCR stimulation (FIG. 6F). The abolishment of RORγt expression in T cells of RORγt cKO mice was verified by immunoblotting analysis (FIG. 6G). The data suggest that IKKβ-RORγt activation mainly induces IL-17A production during TCR signaling, while IKKβ-NF-κB activation regulates the production of multiple cytokines, including IL-2, IFN-γ, IL-4, IL-6, and TNF-α (FIG. 6H).

GLK$^+$$^{IL}$-17A$^+$ T Cells are Diagnostic Biomarkers for Active SLE

Figure 7:
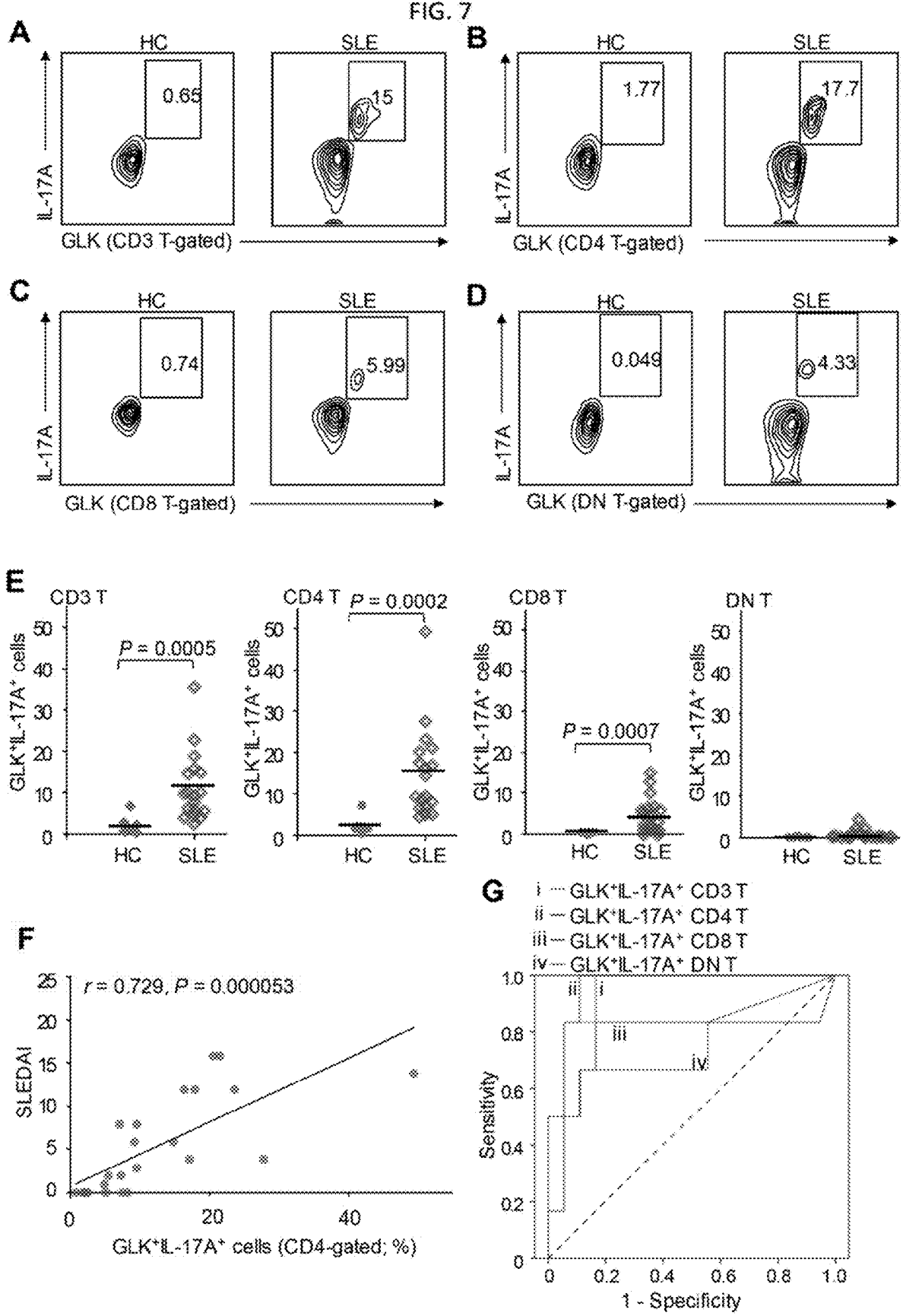
FIG. 7 shows that the frequencies of GLK$^+$ Th17 cells are increased in SLE patients, (a-d) Flow cytometry of GLK$^+$ and IL-17$^+$ T cells (CD3-gated, CD3 plus CD4-gated, CD3 plus CD8-gated, or CD3 plus CD4$^-$CD8$^+$ (double-negative (DN)-gated) from the peripheral blood leukocytes of 6 healthy controls and 18 SLE patients; the results from a representative healthy control (HC) and a representative SLE patient (SLEDAI=12) are shown in the left panel. SLEDAI denotes systemic lupus erythematosus disease activity index, (e) Statistical analyses of GLK$^+$IL-17$^+$ T cells in the healthy control group and the SLE patient group are shown, (f) Positive correlation and significant regression between SLEDAI and the frequencies of GLK$^+$IL-17$^+$ T cells in the CD4$^+$ T subset from all SLE patients (in red) and healthy controls (in blue). (Pearson correlation coefficient: r=0.729, P=0.000053). (g) Receiver operating characteristic (ROC) curves of the frequencies of GLK$^+$IL-17$^+$ cells in T-cell subsets (CD3$^+$, CD4$^+$, CD8$^+$, or DN subset) for detection of active SLE (SLEDAI≥12). The area under the curve (AUC) values of the GLK$^+$IL-17$^+$ subpopulation in CD3$^+$ T cells (0.935, P=0.002), CD4$^+$ T subset (0.944, P=0.001), CD8$^+$ T subset (0.792, P=0.036), and DN T subset (0.759, P=0.062).

To confirm that GLK overexpression induces IL-17A production in T cells of SLE patients, we characterized T cells from 18 SLE patients and 6 healthy controls (Table 1) using flow cytometry. The flow cytometry data showed that GLK overexpression co-existed exclusively with IL-17A production in T cells of all SLE patients (FIG. 7A). Moreover, the frequencies of GLK$^+$IL-17A$^+$ cells in CD4$^+$ T cells were drastically increased in all 18 SLE patients compared to those in healthy controls (FIGS. 7B, E), while those in CD8$^+$ T cells were modestly increased (FIGS. 7C, E). In contrast, the frequencies of GLK$^+$IL-17A$^+$ cells in CD4$^-$CD8$^-$ (double-negative, DN) T cells were not significantly increased in the SLE group compared to the healthy control group; only three SLE patients showed very slight increase (FIGS. 7D-E). These results showed that GLK IL-17A T cells in SLE patients were mainly CD4' T cells, thus, these CD4+ T cells were GLK+IL-17 cells. Moreover, to study whether GLK+IL-17A+ T cell population is a useful diagnostic biomarker for active SLE (SLEDAI≥12), the diagnostic utility of the frequencies of GLK+IL-17A+ T-cell subsets were analyzed by liner regression and receiver operating characteristic (ROC) curve analyses (FIGS. 7F-G). The frequencies of GLK+IL-17A+ cells in CD4+ T cells were correlated (r=0.729, P=0.00053) with SLEDAI (FIG. 7F). According to the coordinates of the ROC curve, the best cutoff value for the frequencies of GLK+IL-17A+ cells in CD4+ T cell population was 15.5%. Moreover, the frequencies of GLK+IL-17A+ cells in CD4+ T cells had a sensitivity of 100% and a specificity of 88.9% for identifying active SLE patients (FIG. 7G). Thus, GLK+ Th17 cell is a diagnostic biomarker for active SLE. Notably, the area under the curve (AUC) value (0.939, P<0.001) of GLK+IL-17A+ frequencies in CD4+ T cells was significantly higher than that in CD8+ or DNT cells. Collectively, these results suggest that GLK overexpression in T cells induces IL-17A production and pathogenic Th17 cells, contributing to the pathogenesis of an SLE patient subpopulation.

Figure 1:
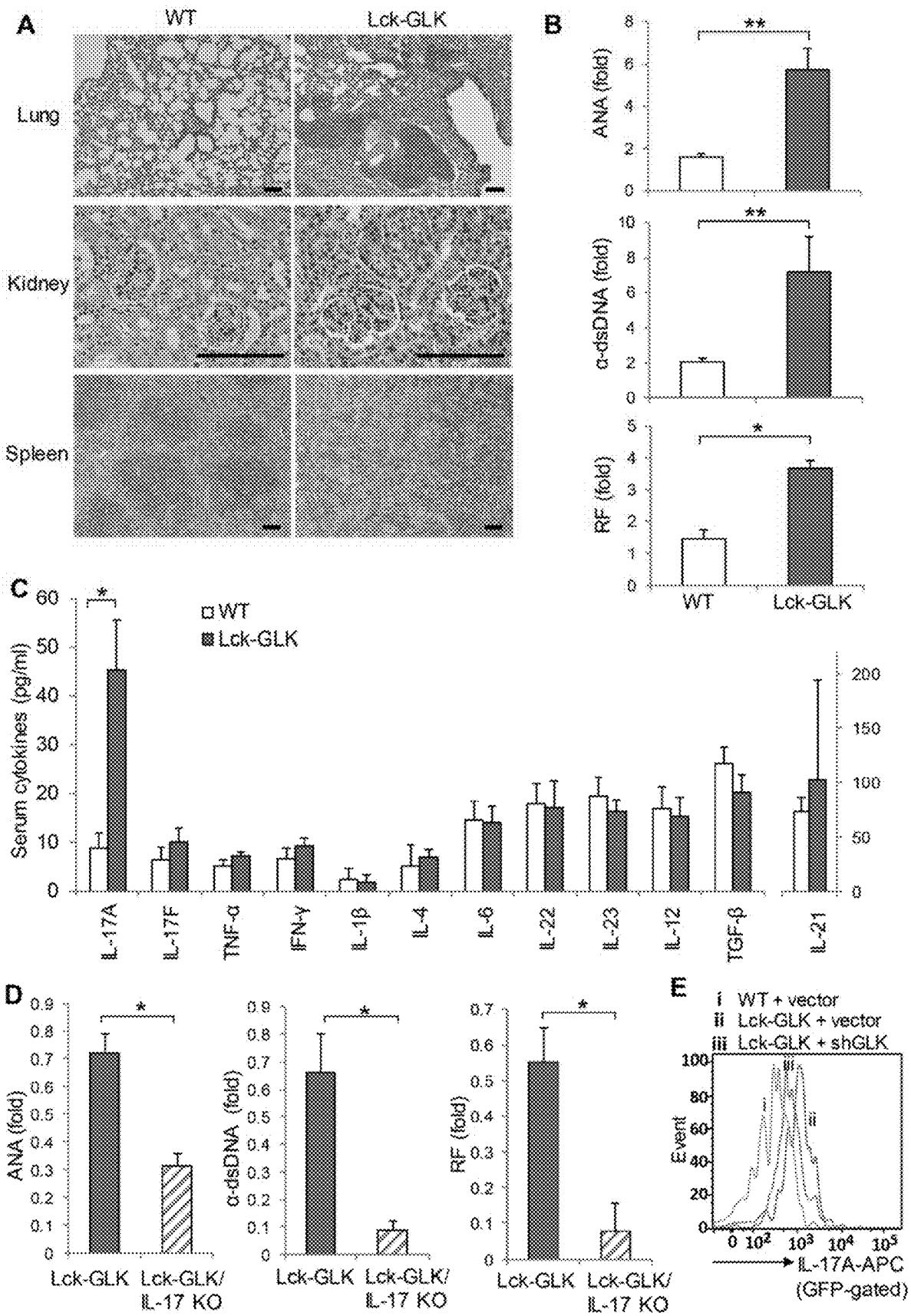
FIG. 1 shows that Lck-GLK transgenic mice display autoimmune phenotypes and selectively increased serum IL-17A levels. (A) Hematoxylin and eosin-stained sections of indicated organs from mice. Arrows, infiltrating immune cells. Bar, 100 μm. (B) Levels of serum autoantibodies from mice were determined by ELISA assays. The levels are presented relative to the value from one of wild-type mice. (C) The serum levels of cytokines in mice were determined by ELISA assays. (D) The serum levels of autoantibodies in Lck-GLK and Lck-GLK/IL-17A KO mice were determined by ELISA assays. The levels are presented relative to the value from one of Lck-GLK mice. (E) IL-17A expression was attenuated by GLK shRNA. Murine primary splenic T cells were transfected with GFP-human GLK shRNA and a control GFP vector. The transfected T cells were stimulated with anti-mouse CD3 antibodies for 3 h and then determined by flow cytometry at day 3 post-transfection. Data show the events of IL-17A-producing T cells (green fluorescent protein (GFP)-gated). WT, wild-type littermate controls; Lck-GLK, T-cell-specific GLK transgenic mice. Lck-GLK/IL-17A KO, Lck-GLK; IL-17A-deficient mice. ANA, anti-nuclear antibody; α-dsDNA, anti-dsDNA antibody; RF, rheumatoid factor. *, P value<0.05; **, P value<0.01 (two-tailed Student's t-test).

Table 1 shows demographic and disease characteristics of SLE patients and healthy controls used in FIG. 1. Demographic characteristics were determined only at the beginning of SLE diagnosis. Durations refer to the length of the disease time after SLE diagnosis. Plus-minus values are means±SD. Abbreviations: SLE, systemic lupus erythematosus; HC, healthy controls; SLEDAI, SLE disease activity index; WBC, white blood cell; HgB, hemoglobin; dsDNA, double-stranded DNA; WHO, World Health Organization; C3 and C4, complement component 3 and component 4; NA, not applicable.

TABLE 1

| Characteristic | SLE (n = 18) | HC (n = 6) |
| --- | --- | --- |
| Age at study entry (years) | 38.2 ± 16.0 | 31.0 ± 6.0 |
| Gender (female, %) | 17 (94.4) | 6 (100) |
| Disease duration (years) | 8.0 ± 5.8 | NA |
| SLEDAI | 7.1 ± 5.4 | NA |
| Fever (%) | 1 (5.6) | NA |
| Arthritis (%) | 7 (38.9) | NA |
| Nephritis (%) | 10 (55.6) | NA |
| Malar rash (%) | 7 (38.9) | NA |
| Serositis (%) | 2 (11.1) | NA |
| Neurologic disorders (%) | 5 (27.8) | NA |
| WBC (/mm$^3$) | 6322 ± 2364 | NA |
| HgB (g/dl) | 12.3 ± 1.9 | NA |
| Platelet (100/mm$^3$) | 271.5 ± 90.6 | NA |
| Creatinine (mg/dl) | 0.86 ± 0.2 | NA |
| Anti-dsDNA antibody (WHO Units/ml) | 213.7 ± 185.7 | NA |
| C3 (mg/dl) | 84.8 ± 31.1 | NA |
| C4 (mg/dl) | 20.9 ± 14.1 | NA |

GLK Induces RORγt Ser-489 Phosphorylation and the AhR-RORγt Complex in Human Autoimmune Patient T Cells Our previous report demonstrates that GLK overexpression induces RORγt Ser-489 phosphorylation and the AhR-RORγt complex. We also found that the interaction between AhR and RORγt could be blocked by a S489-phosphorylated RORγt peptide (FIG. 8A). The data further support that RORγt S489 phosphorylation controls the formation of AhR-RORγt complex. Next, we further studied whether RORγt Ser-489 phosphorylation and the AhR-RORγt complex occur in T cells of human autoimmune patients using immunoblotting and PLA. Immunoblotting data showed that RORγt Ser-489 phosphorylation was drastically enhanced in unstimulated peripheral blood T cells freshly isolated from SLE and RA patients (FIG. 8B). Furthermore, unstimulated peripheral blood T cells from human SLE and RA patients displayed numerous PLA interaction signals between AhR and RORγt (FIG. 8C) or between AhR and phosphorylated RORγt (FIG. 8D). Thus, the GLK-PKCθ/IKKβ-AhR/RORγt signaling cascade is a general mechanism of IL-17A induction in TCR-stimulated or autoimmune T cells.)

Identification of Small Molecule Inhibitors for GLK–Induced AhR-RORγt Complex in Human Autoimmune Patient T Cells Since the AhR-RORγt complex is induced by GLK signaling, we tested whether inhibitors of GLK-PKCθ-IKKβ signaling block AhR-RORγt complex. We used the GLK inhibitor treatment as an example. Because there is no commercial GLK inhibitor, we screened 101,200 compounds to identify GLK inhibitors using both luciferase reporter assays and in vitro kinase assays. Among these compounds that efficiently inhibited GLK signaling in cell lines, two compounds (verteporfin and alexidine dihydrochloride, named C1 and C2, respectively) efficiently inhibited both GLK signaling in cell lines and GLK kinase activity in vitro (FIGS. 9A-B). We found that the GLK inhibitor C1 indeed blocked the AhR-RORγt complex in T cells from SLE and RA patients (FIG. 9C). The PLA signals (FIG. 9D) and FRET signals (FIG. 9E) were inhibited by C1 (verteporfin) treatment.

The Inhibitors of GLK–Induced AhR-RORγt Complex Suppress IL-17 Production and Autoimmune Responses in Mice Because GLK-induced AhR-RORγt complex controls IL-17 production and autoimmune responses in mice, we studied whether the GLK inhibitor C1 (verteporfin) that blocks AhR-RORγt complex also inhibits IL-17 production and autoimmune responses in T-cell-specific GLK transgenic (Lck-GLK Tg) mice. After the GLK inhibitor C1 (verteporfin) treatment (0.556 nmole/g) by intravenous injection every 3 days for 30 days (FIG. 10A), the serum IL-17A levels in Lck-GLK Tg mice were significantly decreased by C1 (verteporfin) treatment compared to those of PBS treatment (FIG. 10B). Moreover, overproduction of autoantibodies in Lck-GLK Tg mice were also abolished by C1 (verteporfin) treatment (FIG. 10C). These results demonstrate that GLK overexpression induces IL-17A overproduction and autoantibody production. To further verify that the GLK inhibitors also works in IL-17A-mediated animal models, we challenged wild-type mice with C1 (verteporfin) or C2 (alexidine dihydrochloride) during EAE and CIA induction. Both C1 (verteporfin) treatment (0.556 nmole/g) and C2 (alexidine dihydrochloride) treatment (0.085 nmole/g) significantly suppressed the diseases severity and serum IL-17A levels of mice in the EAE induction (FIG. 10D). C1 (verteporfin) treatment also inhibited the diseases severity and serum IL-17A levels of mice in the CIA induction (FIG. 10E). The data showed that the verteporfin (C1) treatment preferentially inhibited IL-17A overproduction in all three autoimmune disease models. In addition, the verteporfin (C1) treatment inhibited both Th17 differentiation and IL-17A production from in vitro differentiated Th17 cells (FIGS. 11A-B). In contrast, the verteporfin (C1) treatment enhanced in vitro Treg (Foxp3-expressing CD4+ T cell) differentiation (FIG. 11C); consistently, Treg differentiation of Lgk-GLK transgenic mice was decreased compared to that of wild-type mice (FIG. 11D). These results indicate that GLK inhibitors decreases Th17 cell population but increases Treg cell population.

The Inhibitors of GLK-Induced AhR-RORγt Complex Block IL-17 Production of Human T Cells We further studied whether IL-17A production is abolished by the inhibitors of GLK-induced AhR-RORγt complex in human and murine T cells. We first tested the inhibitor experiment using murine T cells stimulated with TCR signaling (anti-CD3 plus anti-CD28 antibodies). We found that TCR-induced IL-17A production of murine T cells was drastically abolished by the C1 (verteporfin) treatment, whereas TCR-induced IL-17B, IL-17E, and IL-17F levels were not decreased (FIG. 12A). TCR-induced TNF-α and IFN-γ levels were partially reduced by the C1 (verteporfin) treatment (FIG. 12A); this reduction is likely due to the inhibition of NF-κB activation by the C1 (verteporfin) treatment. Next, we studied the blocking effect of IL-17 production by the treatment of C1 (verteporfin) or C2 (alexidine dihydrochloride) using human peripheral blood T cells. TCR-induced IL-17A production was significantly reduced by the C1 (verteporfin) treatment in peripheral blood T cells from healthy controls (FIG. 12B). The IL-17A production in anti-CD3/CD28-stimulated T cells of human autoimmune disease patients was drastically inhibited by C1 (verteporfin) treatment or C2 (alexidine dihydrochloride) treatment (FIG. 12B). Taken together, GLK inhibitors (verteporfin and alexidine dihydrochloride) inhibit GLK-induced AhR-RORγt complex and IL-17A production in human autoimmune patient T cells, as well as the disease severity of autoimmune animal models. Thus, GLK, GLK signaling, or GLK-induced AhR-RORγt complex can be a promising therapeutic target for autoimmune diseases.

GLK Inhibitors Block Cancer Cell Migration and Cancer Metastasis/Recurrence

To study the role of GLK in cancer metastasis/recurrence, we generated the whole-body GLK transgenic (Pol II-GLK Tg) mice using RNA polymerase II (Pol II) promoter-driven human GLK cDNA (FIG. 13A). GLK overexpression was confirmed by real-time PCR (FIG. 13B). To study the effect of GLK on cancer progression, Pol II-GLK Tg mice were bred with a genetically modified lung cancer mouse line, the lung-specific pulmonary surfactant protein A (SPA) promoter-driven EGFR-deletion mutant transgenic (SPA-EGFRdel Tg) mouse line. All 1-year-old SPA-EGFR$^{del}$ Tg mice (9/9) indeed developed lung cancer (PCNA positive) (FIG. 13C), and so did SPA-EGFR$^{del}$; Pol II -GLK Tg mice (15/15) (FIG. 13C). Immunohistochemistry analysis using anti-EGFR-deletion mutant antibodies showed that EGFR$^{del}$-expressing cells are detected in the lung cancer of both SPA-EGFR$^{del}$ Tg mice and SPA-EGFR$^{del}$;Pol II -GLK Tg mice (FIG. 13D). We next studied whether GLK transgene induces lung cancer (EGFR$^{del}$-positive) metastasis to other organs in SPA-EGFR$^{del}$;Pol II -GLK Tg mice. We performed immunohistochemistry using anti-EGFR-deletion mutant antibodies on the tissues of the cervical lymph nodes, the liver, and the brain from wild-type and three different transgenic mice. For regional metastasis to cervical lymph nodes, all but one (14/15) SPA-EGFR$^{del}$; Pol II -GLK Tg mice displayed numerous metastatic EGFR$^{del}$-expressing lung cancer cells in cervical lymph nodes. In contrast, only three of nine SPA-EGFR$^{del}$ Tg mice showed a few metastatic EGFR$^{del}$-expressing lung cancer cells in cervical lymph nodes (FIG. 13E). For distant metastasis, all SPA-EGFR$^{del}$; Pol II-GLK Tg mice displayed metastasis of EGFR$^{del}$-expressing lung cancer cells to the brain (14/15) or liver (15/15) (FIG. 13E and Table 2). In the 9 control SPA-EGFR$^{del}$ Tg mice, only one SPA-EGFR$^{del}$ Tg mouse (1/9) developed both brain metastasis and liver metastasis, only one (1/9) developed liver metastasis, and remaining 7 mice did not develop any detectable distant metastasis (FIG. 13E and Table 2). These results suggest that GLK induces distant metastasis of lung cancer to the brain and liver. Table 2 shows Comparison of EGFR-deletion mutant expression in indicated tissues from individual groups.

TABLE 2

| EGFR$^{del}$ Positive | LN | Brain | Liver |
|---|---|---|---|
| EGFR$^{del}$ (n = 9) | 3§ | 1 | 2 |
| PolII-GLK (n = 11) | 0 | 0 | 0 |
| EGFR$^{del}$; PolII-GLK (n = 15) | 14 | 14 | 15 |
| Fisher's exact test: EGFR$^{del}$ vs. EGFR$^{del}$; PolII-GLK | P = 0.0037** | P = 0.0001*** | P = 0.0001*** |

The symbol § denotes that only three of nine SPA-EGFR$^{del}$ Tg mice showed a few metastatic EGFR$^{del}$-expressing lung cancer cells in cervical lymph nodes.

We studied whether GLK inhibitors also suppress cancer cell migration. The transwell migration assays showed that migration of the cells from glioma, pancreatic cancer, lung cancer, or hepatoma was inhibited by the treatment of C1 (verteporfin) or C2 (alexidine dihydrochloride) (FIG. 14). Moreover, both C1 (verteporfin) and C2 (alexidine dihydrochloride) treatments suppressed tumor growth in the xenograft mouse model using TC-1 lung cancer cells (FIG. 15). To study whether GLK deficiency results in a reduction of lung cancer metastasis, we used a metastatic Lewis lung carcinoma (LLC) mouse model by tail vein injection of luciferase-expressing LLC (LLC/luc) cells. We identified two GLK inhibitors (verteporfin and alexidine dihydrochloride)) using cell-based assays and in vitro kinase assays. The IC50 of C1 (verteporfin) and C2 for GLK kinase activity was 1.15 and 10.05 nM, respectively (Table 3). The molecular docking analyses showed that the GLK inhibitors C1 (verteporfin) and C2 (alexidine dihydrochloride) stably bound to active GLK kinase domain (phospho-GLK [Ser-170]) at the interlace of GLK dimers and the active site of GLK kinase domain, respectively (FIG. 16A-B). The dimerization of Flag-tagged GLK protein and GFP-GLK fusion protein was indeed blocked by the C1 (verteporfin) treatment (FIG. 16C). We treated the LLC/luc cells-containing mice with the GLK inhibitor C1 (verteporfin) or C2 (alexidine dihydrochloride) by intravenous injection every 3 days for 30 days (FIG. 16D). The luciferase activity of LLC/luc cells in the mice was detected by In Vivo Imaging System. The excised lungs were weighed and subjected to H&E staining. The luciferase activity of LLC/luc cells in the lung of injected mice was reduced by the treatment of C1 (verteporfin) or C2 (alexidine dihydrochloride) (FIGS. 16E-F). Consistently, immunohistochemistry analyses also showed a reduction of cancer colony in the C1 (verteporfin) or C2 (alexidine dihydrochloride)-treated mice (FIG. 16G). Moreover, the interaction between GLK and IQGAP1 in the lung tissues were inhibited by the treatment of C1 (verteporfin) or C2 (alexidine dihydrochloride) (FIG. 16H, upper panel), and IQGAP1 phosphorylation was in the lung tissues were inhibited (FIG. 16H, lower panel). Collectively, the data suggest that GLK plays a crucial role in lung cancer metastasis. These results indicate that GLK inhibitors block cancer metastasis and cancer progression. Table 3 shows the half maximal inhibitory concentration (IC50) of verteporfin or alexidine dihydrochloride for MAP4Ks. Inhibition of kinase activity of GLK (MAP4K3) or other MAP4Ks was determined by in vitro kinase assays using myelin basic protein (MBP) as a substrate. Recombinant proteins of kinase domains of various MAP4Ks were used. C1, verteporfin: C2, alexidine dihydrochloride.

TABLE 3

| IC50 | GLK (MAP4K3) | HPK1 (MAP4K1) | HGK (MAP4K4) | KHS (MAP4K5) |
|---|---|---|---|---|
| C1 | 1.15 nM | 7.91 nM | 4.92 nM | 43.88 nM |
| C2 | 10.05 nM | 6.14 nM | 21.82 nM | 18.27 nM |

GLK-Deficient Mice Display Prolonged Lifespan

To study whether inhibition of GLK may result in any spontaneous diseases, we monitored both wild-type and GLK-deficient mice during their lifetime. Surprisingly, GLK-deficient mice displayed a significant extension of lifespan compared to wild-type mice (FIG. 17A). The oldest GLK-deficient mouse was 40.8 months of age. The aged GLK-deficient mice (26.0-40.8 months) did not develop any tumor or discernible diseases. Interestingly, the aged GLK-deficient mice still displayed healthy hair, whereas the aged wild-type mice displayed gray hair (FIG. 17B). A previous publication indicates that T-cell-mediated immune responses, including antigen-induced IFN-γ, IL-2, IL-17A production, are decreased in GLK-deficient T cells. Moreover, Th1/Th2/Th17 differentiation is reduced by GLK deficiency. GLK-deficient mice are also resistant to the induction of MOG-induced experimental autoimmune encephalomyelitis. The longevity of GLK-deficient mice may be due to the inhibition of inflammatory responses by GLK deficiency. This notion is supported by the data that serum levels of the proinflammatory cytokine IL-6, IL-17A, TNFα, IFN-γ, and IL-1β in 20-month-old GLK-deficient mice were drastically decreased compared to those of age-matched wild-type mice (FIG. 17C). Besides Th1 cytokine (IFN-γ) and Th17 cytokine (IL-17A), Th2 cytokine (IL-4) levels were also decreased in the sera of aged GLK-deficient mice (FIG. 17C). The data suggest that inhibition of GLK would not lead to any adverse effects, instead may prevent inflammation.

Our findings indicate that GLK-induced AhR-RORγt complex is a biomarker and therapeutic target for IL-17A-mediated autoimmune disease. In addition, GLK inhibitors (verteporfin and alexidine dihydrochloride) are potential therapeutics.

GLK Interacts Directly with IQGAP1

Following immunoprecipitation of GLK, the GLK-interacting proteins were resolved by SDS-PAGE and visualized by silver staining (FIG. 18A). The seven most prominent protein bands enhanced in GLK-transfected cells were sliced and then digested by trypsin, and the resulting protein peptides were subjected to mass spectrometry analysis. Moreover, four pervanadate-induced tyrosine phosphorylation sites (Tyr-366, Tyr-379, Tyr-574, and Tyr-735) on GLK proteins were identified by mass spectrometry analysis (FIG. 18B). We identified several putative GLK-interacting proteins, including myosin, IQGAP1, vimentin, drebrin, and heat shock protein 70 (HSP70) (ordered by database search scores from highest to lowest). Among these proteins, IQGAP1, a positive regulator of cell migration, was selected for further study, whereas myosins, heat-shock proteins, and cytoskeletal proteins are common contaminant proteins detectable by mass spectrometry. Next, we confirmed the interaction between GLK and IQGAP1 using reciprocal co-immunoprecipitation assays (FIGS. 18C-D). GLK was co-immunoprecipitated with Flag-tagged IQGAP1 proteins with an anti-Flag antibody (FIGS. 18C-D). This co-immunoprecipitation between GLK and IQGAP1 was abolished by GLK (Y735F) mutation (FIG. 18E), suggesting that Tyr-735 phosphorylation of GLK protein is important for the interaction between GLK with IQGAP1. In situ proximity ligation assay (PLA) with a combination of PLA probes corresponding to Flag (Flag-tagged GLK) and Myc (Myc-tagged IQGAP1) showed strong PLA signals in cells over-expressing both proteins than those overexpressing each alone (FIGS. 18F-G). The PLA signals suggest a direct interaction (<40 nm) between GLK and IQGAP1. Moreover, the fluorescence resonance energy transfer (FRET) assay using CFP-tagged GLK and YFP-tagged IQGAP1 fusion proteins showed a direct interaction (1-10 nm) between these two molecules (FIG. 18H). The FRET signals of GLK–IQGAP interaction were inhibited by the treatment of either C1 (verteporfin) (FIG. 18H, right panel). To further confirm the direct interaction, co-immunoprecipitation experiments were performed using purified proteins. Flag-tagged GLK and Myc-tagged IQGAP1 proteins from HEK293T cell lysates were purified by eluting immuno-complexes with Flag and Myc peptides, respectively. The co-immunoprecipitation assays showed an interaction between purified GLK and IQGAP1 proteins (FIG. 18I). The data from different approaches (PLA, FRET, and purified proteins) suggest that GLK interacts directly with IQGAP1.

GLK Promotes Cell Migration by Phosphorylating IQGAP1 at Ser-480

Because GLK directly binds to IQGAP1, we speculated that GLK may be a kinase that regulates IQGAP1-mediated cell migration. To determine whether GLK phosphorylates IQGAP1, in vitro kinase assay was conducted using purified proteins of GLK, GLK kinase-dead (K45E) mutant, and IQGAP1. IQGAP1 phosphorylation was induced by GLK but not GLK kinase-dead (K45E) mutant (FIG. 19A). Following SDS-PAGE fractionation and mass spectrometry analysis, Ser-480 was identified as the GLK-phosphorylated residue on IQGAP1. Next, we tested whether the GLK-induced IQGAP1 Ser-480 phosphorylation regulates the activation of Cdc42 or Rac1, as well as the interaction of IQGAP1 with Cdc42 or Rac1. Immunoprecipitation data showed that active (GTP-binding) Cdc42 proteins were increased in GLK plus IQGAP1-overexpressing cells; conversely, active Cdc42 protein levels were attenuated by overexpression of GLK plus IQGAP1 (S480A) mutant (FIG. 19B, lower panel). In contrast, active (GTP-binding) Rac1 protein levels were not increased by GLK plus IQGAP1 overexpression (FIG. 19C, lower panel). These results were further supported by ELISA results of Cdc42 and Rac1 activation (FIG. 19D-E). In addition, co-immunoprecipitation data showed that the interaction of IQGAP1 with either Cdc42 or Rac1 was not affected by the IQGAP1 (S480A) mutation (upper panel of FIGS. 19B-C). To evaluate the role of IQGAP1 Ser-480 phosphorylation in IQGAP1-mediated cell migration, HCC827 cells were co-transfected with IQGAP1 (S480A) phosphorylation-defective mutant and GLK plasmids. The transwell migration assays showed that the migrated cell number of GLK-overexpressing cell was decreased by overexpression of IQGAP1 (S480A) mutant (FIG. 19F, top-right panel; FIGS. 19G-H). Conversely, overexpression of two IQGAP1 Ser-480 phosphomimetic (S480D and S480E) mutants induced a higher cell migration ability than that of overexpression of IQGAP1 or IQGAP1 (S480A) mutant in HCC827 lung cancer cells. These results suggest that IQGAP1 Ser-480 phosphorylation is responsible for IQGAP1 activation and IQGAP1/Cdc42-mediated cell migration.

Our results suggest that GLK interacts with and phosphorylates IQGAP1. We next studied the interaction between GLK proline regions and IQGAP1 WW domain indeed controls the GLK–IQGAP1-induced cell migration.

HCC827 lung cancer cells co-transfected with GLK and IQGAP1 displayed enhancement of migration than that of vector control cells, whereas co-transfection of GLK plus IQGAP1 (ΔWW) mutant abrogated the enhanced cell migration (FIGS. 19F-G). Overexpression of GLK (P436/437A), (P478/479A), or (P436/437A;P478/479A) mutant attenuated GLK-induced cell migration (FIGS. 19F-G). Overexpression of GLK and IQGAP1 was confirmed by immunoblotting analysis (FIG. 19H). To demonstrate the phosphorylation of IQGAP1 Ser-480 residue, we generated an anti-phospho-IQGAP1 (Ser-480) monoclonal antibody, which specifically recognized IQGAP1 WT but not S480A mutant (FIG. 19I).

IQGAP1 Mediates GLK–Induced Cancer Metastasis

We next studied whether GLK promotes metastasis of lung cancer through IQGAP1-mediated cancer cell migration. To shorten the time (12 months) required for the development of lung cancer metastasis in SPA-EGFR$^{del}$;Pol II -GLK Tg mice, we generated a GLK mutant transgenic mouse line (Pol II -GLK$^{E351K}$Tg), which expressed a constitutively activated GLK (E351K) mutant (FIGS. 20A-C). Notably, the GLK (E351K) mutation was reported in the supplementary information of a previous publication; however, the functional consequence of GLK (E351K) mutation has not been demonstrated until this study (FIGS. 20A-B). Overexpression of GLK (E351K) mutant was confirmed by real-time PCR (FIG. 20D). Next, we bred Pol II -GLK$^{E351K}$ Tg mice with SPA-EGFR$^{del}$ Tg mice to generate SPA-EGFR$^{del}$;Pol II -GLK$^{K351K}$ Tg mice, which displayed enhanced GLK protein levels in the lung compared to those of SPA-EGFR$^{del}$ Tg mice (FIG. 20E). SPA-EGFR$^{del}$; Pol II -GLK$^{E351K}$ Tg mice (8/8) indeed developed lung cancer (FIG. 20F) and regional/distant metastasis at a younger age (7-month-old) than that of SPA-EGFR$^{del}$; Pol II -GLK Tg mice. All 7-month-old SPA-EGFR$^{del}$; Pol II -GLK$^{E351K}$ Tg mice displayed distant metastasis of EGFR$^{del}$-expressing lung cancer cells to the brain and/or liver (both brain and liver [6/8], brain only [1/8], and liver only [1/8] (FIG. 19G and Table 4). In contrast, all SPA-EGFR$^{del}$Pol II -GLK$^{E351K}$;IQGAP1$^{-/-}$ mice did not develop any distant metastasis (3/3) at 7-month-old age (FIG. 20G and Table 4). These data suggest that GLK induces distant metastasis through IQGAP1 in SPA-EGFR$^{del}$ lung cancer model. To verify this notion, we studied the interaction between GLK and IQGAP1, as well as IQGAP1 Ser-480 phosphorylation in tissues of human non-small cell lung cancer (NSCLC).

TABLE 4

| EGFR$^{del}$ Positive | LN | Brain | Liver |
|---|---|---|---|
| EGFR$^{del}$; PolII-GLK$^{E351K}$ (n = 8) | 8 | 7 | 7 |
| EGFR$^{del}$; PolII-GLK$^{E251K}$; IQGAP1$^{-/-}$ (n = 6) | 0 | 0 | 0 |
| Fisher's exact test: EGFR$^{del}$; PolII-GLK$^{E251K}$ vs. EGFR$^{del}$; PolII-GLK$^{E251K}$; IQGAP1$^{-/-}$ | P = 0.0003*** | P = 0.0047** | P = 0.0047** |

GLK–IQGAP1 Complex is Correlated with Poor Survival of Human NSCLC

To study the interaction of GLK with IQGAP1 in NSCLC tissues, we collected clinical lung tissues from 7 human NSCLC patients who underwent pulmonary resection. We also employed a commercially available pulmonary tissue array containing 85 NSCLC tissues (including 49 squamous cell carcinoma, 17 adenocarcinoma, 11 bronchioloalveolar carcinoma, and 8 large cell carcinoma) and 68 normal adjacent tissues, as well as 3 small cell lung carcinoma tissues. These tissues were subjected to in situ proximity ligation assay (PLA) with a combination of paired PLA probes corresponding to GLK and IQGAP1. The data showed multiple strong PLA signals in most (81/92) of NSCLC tissues but not in any small cell carcinoma tissues (FIGS. 21A-B). Most (61/68) of normal adjacent tissues from NSCLC patients did not display any PLA signals, while 7 of 68 normal adjacent tissues showed much less PLA signals. The few PLA signals in the normal adjacent tissues of NSCLC patients may be metastatic cancer cells migrating from original lesion. These results suggest that the GLK–IQGAP1 complex in pulmonary tissue may be a diagnostic biomarker for NSCLC. Next, we studied whether the GLK–IQGAP1 complex could act as a potential prognostic biomarker for NSCLCs. NSCLC (squamous cell carcinoma and adenocarcinoma) patients, whose survival data were available, were divided into four PLA-signal subgroups after cluster analyses. The two subgroups with highest PLA signals contained only one and two patients, respectively, thus, these two subgroups were excluded from further analysis. The remaining two subgroups (n=63) were subjected to Kaplan-Meier survival analysis using the survival data (available from the provider). NSCLC patients with high PLA signals showed poor survival during follow-up periods (n=63, PLA signal-High versus PLA signal-Low, P=0.069) (FIG. 21C). The higher P value (P=0.069) may be due to the exclusion of three data with highest PLA signals. Nevertheless, NSCLC patients with more GLK–IQGAP1 complexes have a lower survival rate than that of the patients with less GLK–IQGAP1 complexes. Because 40% to 60% of NSCLC patients the of cancer recurrence after cancer resection, we studied whether the GLK–IQGAP1 complex is associated with NSCLC metastasis. The cancer cells with the GLK–IQGAP1 complex particularly accumulated on/near the vascular wall in the lung (FIG. 21D); GLK–IQGAP1 complex-positive cells also existed in lumen of the blood vessel (FIG. 21D). Moreover, the bone, lymph node, or soft tissue section with metastatic carcinoma displayed GLK–IQGAP1 complex-positive cells (FIG. 21D), the cancer cells was verified using (proliferating cell nuclear antigen) PCNA staining (FIG. 21D). Merged images show that the GLK–IQGAP1 complex-positive cells in these tissues were indeed cancer cells (FIG. 21D). The data suggest that lung cancer cells with the GLK–IQGAP1 complex tend to be metastatic. Next, we examined the GLK-induced IQGAP1 Ser-480 phosphorylation in human NSCLC tissues. After several failed attempts, we finally obtained a monoclonal antibody (mAb) against IQGAP1 Ser-480 phosphorylation. However, the immunostaining signal using phospho-IQGAP1 mAb was not strong enough to provide a discernible signal. To enhance the specificity and staining signal of anti-phospho-IQGAP1 mAb, we performed PLA that amplifies phosphorylation signals like a polymerase chain reaction with a combination of paired PLA probes corresponding to IQGAP1 and phospho-IQGAP1 Ser-480. The antibody specificity was demonstrated using IQGAP1 S480A mutant-expressing cells and IQGAP1-knockout lung cancer tissues (SPA-EGFR$^{del}$;Pol II-GLK$^{E351K}$; IQGAP1$^{-/-}$). Using human NSCLC tissues, we found multiple PEA signals of IQGAP1 Ser-480 phosphorylation in 82.7% (72/87) of tumor tissues tested (FIGS. 21E-F). The phospho-IQGAP1 PLA signals coexisted with PCNA staining in the same cells (FIG. 21E). Moreover, NSCLC (squamous cell carcinoma and adenocarcinoma) patients were divided into PLA signal-High and PLA signal-Low subgroups after cluster analyses. Kaplan-Meier survival analysis showed that NSCLC patients with high phospho-IQGAP1 PLA signals had poor survival during follow-up periods (n=63, PLA signal-High versus PLA signal-Low, P=0.037) (FIG. 21G). Collectively, our findings suggest that GLK promotes cell migration and cancer metastasis by direct binding to and phosphorylating IQGAP1.

All references cited and discussed in this specification are incorporated herein by reference in their entireties and to the same extent as if each reference was individually incorporated by reference.

What is claimed is:

1. A method for identifying an inhibitor of AhR-phospho-RORγt protein complex, comprising:
   (a) providing a cell culture, in which cells in the culture express both Aryl hydrocarbon Receptor (AhR) protein and phospho-Retinoic-acid-receptor-related orphan nuclear receptor gamma t (RORγt) protein;
   (b) incubating the cell culture in the presence of a test agent;
   (c) assaying the level of an AhR-phospho-RORγt protein complex in the presence of the test agent;
   (d) comparing the level of the AhR-phospho-RORγt protein complex in the presence of the test agent with a control; and
   (e) identifying the test agent as the inhibitor of the AhR-phospho-RORγt protein complex when the comparing step indicates that there is a reduction in the level of the AhR-phospho-RORγt protein complex in the presence of the test agent as compared with the control.

2. The method of claim 1, wherein the assaying step performs immunoblotting using an anti-phospho-RORγt [Ser489] antibody.

3. The method of claim 1, wherein the cells are selected from the group consisting of T cells of Lck-GLK transgenic mice, GLK-overexpressing T cells TCR-activated T cells, and AhR+RORγt+IKKβ overexpressing cells.

4. The method of claim 1, wherein:
(i) the providing step provides cells that are co-transfected with CFP-AhR, YFP-RORγt, and IKKβ plasmids;
(ii) the assaying step performs a fluorescence resonance energy transfer (FRET) assay; and
(iii) the identifying step identifies the test agent as the inhibitor of the AhR-phospho-RORγt protein complex when the comparing step indicates that there is a reduction of fluorescence intensity emitted by the YFP-RORγt in the presence of the test agent as compared with the control.

5. The method of claim 1, wherein:
(i) the providing step provides cells that are co-transfected with an epitope tagged AhR, Myc-RORγt, and IKKβ plasmids;
(ii) the assaying step is performed using ALPHA assay with anti-Myc antibody-conjugated acceptor beads and anti-epitope antibody-coated donor beads; and
(iii) the identifying step identifies the test agent as the inhibitor of the AhR-phospho-RORγt protein complex when the comparing step indicates there is a reduction of signal emitted by the anti-Myc antibody-conjugated acceptor beads in the presence of the test agent as compared with the control;
wherein the epitope consists of the sequence of SEQ ID NO: 1.

6. The method of claim 1, wherein:
(i) the providing step provides cells selected from the group consisting of T cells of Lck-GLK transgenic mice, GLK-overexpressing T cells, TCR-activated T cells and AhR+RORγt+IKKβ overexpressing cells;
(ii) the assaying step performs an in situ proximity ligation assay (PLA) using anti-AhR antibody and anti-RORγt or anti-phospho-RORγt [Ser489] antibody as primary antibodies, secondary antibodies as PLA probes, and fluorescent-labeled complementary oligonucleotide probes for signal detection; and
(iii) the identifying step identifies the test agent as the inhibitor of the AhR-phospho-RORγt protein complex when the comparing step indicates there is a fluorescence signal reduction in the presence of the test agent as compared with the control.

7. The method of claim 1, wherein:
(i) the providing step provides cells that are co-transfected with Myc-AhR, epitope tagged RORγt, and IKKβ plasmids;
(ii) the assaying step performs a co-immunoprecipitation assay by incubating cell extracts with anti-epitope agarose beads or anti-Myc agarose beads to precipitate the AhR-phospho-RORγt protein complex and immunoblotting the AhR-phospho-RORγt complex immunoprecipitated with an anti-Myc or an anti-epitope antibody; and
(iii) the identifying step identifies the test agent as the inhibitor of the AhR-phospho-RORγt protein complex when the comparing result indicates there is a reduction of signal in the presence of the test agent as compared with the control;
wherein the epitope consists of the sequence of SEQ ID NO: 1.

8. The method of claim 1, wherein:
(i) the providing step provides cells selected from the group consisting of T cells of Lck-GLK transgenic mice, GLK-overexpressing cells, TCR-activated T cells and AhR+RORγt+IKKβ overexpressing cells;
(ii) the assaying step performs a chromatin immunoprecipitation (ChIP)-DNA sequencing assay using an anti-RORγt antibody to immunoprecipitate the AhR-phospho-RORγt protein complex and performing a PCR using a pair of primers comprising an AhR-binding site nucleotide sequence in IL-17A promoter DNA sequence to obtain a PCR product; and
(iii) the identifying step identifies the test agent as the inhibitor of the AhR-phospho-RORγt complex when the comparing step indicates there is a reduction in the quantity of the PCR product in the presence of the test agent as compared with the control.

9. A method for identifying an inhibitor of GLK-IQGAP1 protein complex, comprising:
(a) providing a cell culture, in which cells in the culture express both Germinal Center Kinase (GCK)-Like Kinase (GLK) protein and Ras GTPase-activating-like protein IQGAP1 (IQGAP1) protein;
(b) incubating the cell culture in the presence of a test agent;
(c) assaying the level of the GLK-IQGAP1 protein complex in the presence of the test agent;
(d) comparing the level of the GLK-IQGAP1 protein complex in the presence of the test agent with a control; and
(e) identifying the test agent as the inhibitor of the GLK-IQGAP1 protein complex when the comparing step indicates that there is a reduction in the level of the GLK-IQGAP1 protein complex in the presence of the test agent as compared with the control.

10. The method of claim 9, wherein:
(i) the providing step provides cells selected from the group consisting of GLK transgenic mice, GLK-overexpressing cells, and GLK+IQGAP1-overexpressing cells;
(ii) the assaying step performs an in situ proximity ligation assay (PLA) using anti-IQGAP1 antibody and anti-GLK or anti-phospho-IQGAP1 [Ser480] antibody as primary antibodies, secondary antibodies as PLA probes, and fluorescent-labeled complementary oligonucleotide probes for signal detection; and
(iii) the identifying step identities the test agent as the inhibitor of the GLK-IQGAP1 protein complex when the comparing step indicates that there is a fluorescence signal reduction in the presence of the test agent as compared with the control.

11. The method of claim 9, wherein the assaying step performs immunoblotting using an anti-phospho-IQGAP1 [Ser480] antibody.

12. A method for treating an IL-17A associated disease, comprising:
administering an effective amount of an AhR-phospho-RORγt protein complex inhibitor identified by the method of claim 1 to a subject in need thereof to treat the IL-17A associated disease in the subject in need thereof.

13. The method of claim 12, wherein the AhR-phospho-RORγt protein complex inhibitor is selected from the group consisting of verteporfin and alexidine dihydrochloride.

14. The method of claim 12, wherein the IL-17A associated disease is selected from the group consisting of an autoimmune disease, GLK-overexpressing cancer cell metastasis, and GLK-overexpressing cancer cell recurrence.

15. The method of claim 14, in which the method treats the autoimmune disease in the subject in need thereof and the administering step administers the AhR-phospho-RORγt protein complex inhibitor verteporfin or alexidine dihydrochloride.

16. The method of claim 14, in which the method treats GLK-overexpressing cancer cell metastasis in the subject in need thereof and the administering step administers the AhR-phospho-RORγt protein complex inhibitor verteporfin or alexidine dihydrochloride.

17. The method of claim 14, in which the method treats GLK-overexpressing cancer cell metastasis in the subject in need thereof and the administering step administers the AhR-phospho-RORγt protein complex inhibitor verteporfin.

18. A method for treating GLK-overexpressing cancer cell metastasis, comprising:
   administering an effective amount of an inhibitor of GLK-IQGAP1 protein complex identified by the method of claim 9 to a subject in need thereof to treat the GLK-overexpressing cancer cell metastasis in the subject in need thereof.

19. The method of claim 18, wherein the inhibitor of GLK-IQGAP1 protein complex is verteporfin or alexidine dihydrochloride.

20. The method of claim 18, wherein the inhibitor of GLK-IQGAP1 protein complex is verteporfin.

\* \* \* \* \*

SEQUENCE LISTING

```
<160> NUMBER OF SEQ ID NOS: 32

<210> SEQ ID NO 1
<211> LENGTH: 8
<212> TYPE: PRT
<213> ORGANISM: Artificial Sequence
<220> FEATURE:
<223> OTHER INFORMATION: FLAG-tag

<400> SEQUENCE: 1

Asp Tyr Lys Asp Asp Asp Asp Lys
1               5

<210> SEQ ID NO 2
<211> LENGTH: 92
<212> TYPE: DNA
<213> ORGANISM: Artificial Sequence
<220> FEATURE:
<223> OTHER INFORMATION: PKC theta intron 1 and exon 2 deleted sequence

<400> SEQUENCE: 2
ggtggaacac taaaaataat atgtcttaga gccccataca tacagtgttt gtcttttgtc      60
atttttctag ggaacaacca tgtcaccgtt tc                                    92

<210> SEQ ID NO 3
<211> LENGTH: 16
<212> TYPE: PRT
<213> ORGANISM: Artificial Sequence
<220> FEATURE:
<223> OTHER INFORMATION: murine GLK epitope 4 to 19

<400> SEQUENCE: 3

Gly Phe Asp Leu Ser Arg Arg Asn Pro Gln Glu Asp Phe Glu Leu Ile
1               5                   10                  15

<210> SEQ ID NO 4
<211> LENGTH: 19
<212> TYPE: PRT
<213> ORGANISM: Artificial Sequence
<220> FEATURE:
<223> OTHER INFORMATION: murine GLK epitope 514 to 533

<400> SEQUENCE: 4

Glu Gln Arg Gly Thr Asn Leu Ser Arg Lys Glu Lys Lys Asp Val Pro
1               5                   10                  15

Lys Pro Ile

<210> SEQ ID NO 5
<211> LENGTH: 13
<212> TYPE: PRT
<213> ORGANISM: Artificial Sequence
<220> FEATURE:
<223> OTHER INFORMATION: murine ROR gamma t epitope

<400> SEQUENCE: 5

Phe Ser Thr Asp Val Glu Ser Pro Glu Gly Leu Ser Lys
1               5                   10
```

<210> SEQ ID NO 6
<211> LENGTH: 13
<212> TYPE: PRT
<213> ORGANISM: Homo sapiens

<400> SEQUENCE: 6

Phe Ser Thr Glu Thr Glu Ser Pro Val Gly Leu Ser Lys
1               5                   10

<210> SEQ ID NO 7
<211> LENGTH: 22
<212> TYPE: DNA
<213> ORGANISM: Artificial Sequence
<220> FEATURE:
<223> OTHER INFORMATION: human GLK shRNA

<400> SEQUENCE: 7
gtgccactta gaatgtttga aa                                              22

<210> SEQ ID NO 8
<211> LENGTH: 32
<212> TYPE: DNA
<213> ORGANISM: Artificial Sequence
<220> FEATURE:
<223> OTHER INFORMATION: AhR-binding site

<400> SEQUENCE: 8
atgtccatac atacatgata ctgaatcaca gc                                   32

<210> SEQ ID NO 9
<211> LENGTH: 42
<212> TYPE: DNA
<213> ORGANISM: Artificial Sequence
<220> FEATURE:
<223> OTHER INFORMATION: RORgamma t-binding site (-887)

<400> SEQUENCE: 9
ctcaaagaca taaaggcaac cgtgatctca tggagaggag ag                        42

<210> SEQ ID NO 10
<211> LENGTH: 25
<212> TYPE: DNA
<213> ORGANISM: Artificial Sequence
<220> FEATURE:
<223> OTHER INFORMATION: ROR gamma t-binding site (-120)

<400> SEQUENCE: 10
ggttctgtgc tgcaatcatt tgagg                                           25

<210> SEQ ID NO 11
<211> LENGTH: 32
<212> TYPE: DNA
<213> ORGANISM: Artificial Sequence
<220> FEATURE:
<223> OTHER INFORMATION: STAT3-binding site

<400> SEQUENCE: 11
agacagatgt tgcctgtcat aaagggggtgg tt                                  32

<210> SEQ ID NO 12
<211> LENGTH: 21
<212> TYPE: DNA
<213> ORGANISM: Artificial Sequence
<220> FEATURE:
<223> OTHER INFORMATION: ROR gamma t (-877 to -872) forward primer

<400> SEQUENCE: 12

```
ctgaagagct gggacctaat g                                             21

<210> SEQ ID NO 13
<211> LENGTH: 21
<212> TYPE: DNA
<213> ORGANISM: Artificial Sequence
<220> FEATURE:
<223> OTHER INFORMATION: ROR gamma t (-877 to -872) reverse primer

<400> SEQUENCE: 13
gactactaac aggaggagat g                                             21

<210> SEQ ID NO 14
<211> LENGTH: 24
<212> TYPE: DNA
<213> ORGANISM: Artificial Sequence
<220> FEATURE:
<223> OTHER INFORMATION: ROR gamma t -120 to -115  forward primer

<400> SEQUENCE: 14
ggttctgtgc tgacctcatt tgag                                          24

<210> SEQ ID NO 15
<211> LENGTH: 21
<212> TYPE: DNA
<213> ORGANISM: Artificial Sequence
<220> FEATURE:
<223> OTHER INFORMATION: ROR gamma t (-120 to -115) reverse primer

<400> SEQUENCE: 15
cacagatgaa gctctccctg g                                             21

<210> SEQ ID NO 16
<211> LENGTH: 23
<212> TYPE: DNA
<213> ORGANISM: Artificial Sequence
<220> FEATURE:
<223> OTHER INFORMATION: AhR forward primer

<400> SEQUENCE: 16
gagactcaca aaccattact atg                                           23

<210> SEQ ID NO 17
<211> LENGTH: 21
<212> TYPE: DNA
<213> ORGANISM: Artificial Sequence
<220> FEATURE:
<223> OTHER INFORMATION: AhR reverse primer

<400> SEQUENCE: 17
cacagatgaa gctctccctg g                                             21

<210> SEQ ID NO 18
<211> LENGTH: 23
<212> TYPE: DNA
<213> ORGANISM: Artificial Sequence
<220> FEATURE:
<223> OTHER INFORMATION: STAT3 forward primer

<400> SEQUENCE: 18
gagactcaca aaccattact atg                                           23

<210> SEQ ID NO 19
<211> LENGTH: 21
<212> TYPE: DNA
```

```
<213> ORGANISM: Artificial Sequence
<220> FEATURE:
<223> OTHER INFORMATION: STAT3 reverse primer

<400> SEQUENCE: 19
cacagatgaa gctctccctg g                                                 21

<210> SEQ ID NO 20
<211> LENGTH: 20
<212> TYPE: DNA
<213> ORGANISM: Artificial Sequence
<220> FEATURE:
<223> OTHER INFORMATION: IRF4 forward primer

<400> SEQUENCE: 20
gggcaaggga tgctctctag                                                   20

<210> SEQ ID NO 21
<211> LENGTH: 20
<212> TYPE: DNA
<213> ORGANISM: Artificial Sequence
<220> FEATURE:
<223> OTHER INFORMATION: IRF4 reverse primer

<400> SEQUENCE: 21
ctgaagctgc tgcagagctg                                                   20

<210> SEQ ID NO 22
<211> LENGTH: 22
<212> TYPE: DNA
<213> ORGANISM: Artificial Sequence
<220> FEATURE:
<223> OTHER INFORMATION: KLF4 forward primer

<400> SEQUENCE: 22
gggtattatc ccaagggtat cc                                                22

<210> SEQ ID NO 23
<211> LENGTH: 22
<212> TYPE: DNA
<213> ORGANISM: Artificial Sequence
<220> FEATURE:
<223> OTHER INFORMATION: KLF4 reverse primer

<400> SEQUENCE: 23
atgcagcatg aggtggaccg at                                                22

<210> SEQ ID NO 24
<211> LENGTH: 21
<212> TYPE: DNA
<213> ORGANISM: Artificial Sequence
<220> FEATURE:
<223> OTHER INFORMATION: BATF forward primer

<400> SEQUENCE: 24
gaacttctgc ccttcccatc t                                                 21

<210> SEQ ID NO 25
<211> LENGTH: 20
<212> TYPE: DNA
<213> ORGANISM: Artificial Sequence
<220> FEATURE:
<223> OTHER INFORMATION: BATF reverse primer

<400> SEQUENCE: 25
cagcacagaa ccaccccttt                                                   20
```

<210> SEQ ID NO 26
<211> LENGTH: 23
<212> TYPE: DNA
<213> ORGANISM: Artificial Sequence
<220> FEATURE:
<223> OTHER INFORMATION: IL-17A forward primer

<400> SEQUENCE: 26
gagactcaca aaccattact atg                                        23

<210> SEQ ID NO 27
<211> LENGTH: 21
<212> TYPE: DNA
<213> ORGANISM: Artificial Sequence
<220> FEATURE:
<223> OTHER INFORMATION: IL-17A reverse primer

<400> SEQUENCE: 27
cacagatgaa gctctcccctg g                                          21

<210> SEQ ID NO 28
<211> LENGTH: 1657
<212> TYPE: PRT
<213> ORGANISM: Homo sapiens

<400> SEQUENCE: 28

Met Ser Ala Ala Asp Glu Val Asp Gly Leu Gly Val Ala Arg Pro His
1               5                   10                  15

Tyr Gly Ser Val Leu Asp Asn Glu Arg Leu Thr Ala Glu Glu Met Asp
            20                  25                  30

Glu Arg Arg Arg Gln Asn Val Ala Tyr Glu Tyr Leu Cys His Leu Glu
        35                  40                  45

Glu Ala Lys Arg Trp Met Glu Ala Cys Leu Gly Glu Asp Leu Pro Pro
    50                  55                  60

Thr Thr Glu Leu Glu Glu Gly Leu Arg Asn Gly Val Tyr Leu Ala Lys
65                  70                  75                  80

Leu Gly Asn Phe Phe Ser Pro Lys Val Val Ser Leu Lys Lys Ile Tyr
                85                  90                  95

Asp Arg Glu Gln Thr Arg Tyr Lys Ala Thr Gly Leu His Phe Arg His
            100                 105                 110

Thr Asp Asn Val Ile Gln Trp Leu Asn Ala Met Asp Glu Ile Gly Leu
        115                 120                 125

Pro Lys Ile Phe Tyr Pro Glu Thr Thr Asp Ile Tyr Asp Arg Lys Asn
    130                 135                 140

Met Pro Arg Cys Ile Tyr Cys Ile His Ala Leu Ser Leu Tyr Leu Phe
145                 150                 155                 160

Lys Leu Gly Leu Ala Pro Gln Ile Gln Asp Leu Tyr Gly Lys Val Asp
                165                 170                 175

Phe Thr Glu Glu Glu Ile Asn Asn Met Lys Thr Glu Leu Glu Lys Tyr
            180                 185                 190

Gly Ile Gln Met Pro Ala Phe Ser Lys Ile Gly Gly Ile Leu Ala Asn
        195                 200                 205

Glu Leu Ser Val Asp Glu Ala Ala Leu His Ala Ala Val Ile Ala Ile
    210                 215                 220

Asn Glu Ala Ile Asp Arg Arg Ile Pro Ala Asp Thr Phe Ala Ala Leu
225                 230                 235                 240

Lys Asn Pro Asn Ala Met Leu Val Asn Leu Glu Glu Pro Leu Ala Ser

```
                      245                 250                 255
Thr Tyr Gln Asp Ile Leu Tyr Gln Ala Lys Gln Asp Lys Met Thr Asn
                  260                 265                 270

Ala Lys Asn Arg Thr Glu Asn Ser Glu Arg Glu Arg Asp Val Tyr Glu
              275                 280                 285

Glu Leu Leu Thr Gln Ala Glu Ile Gln Gly Asn Ile Asn Lys Val Asn
          290                 295                 300

Thr Phe Ser Ala Leu Ala Asn Ile Asp Leu Ala Leu Glu Gln Gly Asp
305                 310                 315                 320

Ala Leu Ala Leu Phe Arg Ala Leu Gln Ser Pro Ala Leu Gly Leu Arg
                  325                 330                 335

Gly Leu Gln Gln Gln Asn Ser Asp Trp Tyr Leu Lys Gln Leu Leu Ser
              340                 345                 350

Asp Lys Gln Gln Lys Arg Gln Ser Gly Gln Thr Asp Pro Leu Gln Lys
          355                 360                 365

Glu Glu Leu Gln Ser Gly Val Asp Ala Ala Asn Ser Ala Ala Gln Gln
      370                 375                 380

Tyr Gln Arg Arg Leu Ala Ala Val Ala Leu Ile Asn Ala Ala Ile Gln
385                 390                 395                 400

Lys Gly Val Ala Glu Lys Thr Val Leu Glu Leu Met Asn Pro Glu Ala
                  405                 410                 415

Gln Leu Pro Gln Val Tyr Pro Phe Ala Ala Asp Leu Tyr Gln Lys Glu
              420                 425                 430

Leu Ala Thr Leu Gln Arg Gln Ser Pro Glu His Asn Leu Thr His Pro
          435                 440                 445

Glu Leu Ser Val Ala Val Glu Met Leu Ser Ser Val Ala Leu Ile Asn
      450                 455                 460

Arg Ala Leu Glu Ser Gly Asp Val Asn Thr Val Trp Lys Gln Leu Ser
465                 470                 475                 480

Ser Ser Val Thr Gly Leu Thr Asn Ile Glu Glu Glu Asn Cys Gln Arg
                  485                 490                 495

Tyr Leu Asp Glu Leu Met Lys Leu Lys Ala Gln Ala His Ala Glu Asn
              500                 505                 510

Asn Glu Phe Ile Thr Trp Asn Asp Ile Gln Ala Cys Val Asp His Val
          515                 520                 525

Asn Leu Val Val Gln Glu Glu His Glu Arg Ile Leu Ala Ile Gly Leu
      530                 535                 540

Ile Asn Glu Ala Leu Asp Glu Gly Asp Ala Gln Lys Thr Leu Gln Ala
545                 550                 555                 560

Leu Gln Ile Pro Ala Ala Lys Leu Glu Gly Val Leu Ala Glu Val Ala
                  565                 570                 575

Gln His Tyr Gln Asp Thr Leu Ile Arg Ala Lys Arg Glu Lys Ala Gln
              580                 585                 590

Glu Ile Gln Asp Glu Ser Ala Val Leu Trp Leu Asp Glu Ile Gln Gly
          595                 600                 605

Gly Ile Trp Gln Ser Asn Lys Asp Thr Gln Glu Ala Gln Lys Phe Ala
      610                 615                 620

Leu Gly Ile Phe Ala Ile Asn Glu Ala Val Glu Ser Gly Asp Val Gly
625                 630                 635                 640

Lys Thr Leu Ser Ala Leu Arg Ser Pro Asp Val Gly Leu Tyr Gly Val
                  645                 650                 655

Ile Pro Glu Cys Gly Glu Thr Tyr His Ser Asp Leu Ala Glu Ala Lys
              660                 665                 670
```

```
Lys Lys Lys Leu Ala Val Gly Asp Asn Asn Ser Lys Trp Val Lys His
        675                 680                 685

Trp Val Lys Gly Gly Tyr Tyr Tyr His Asn Leu Glu Thr Gln Glu
        690                 695                 700

Gly Gly Trp Asp Glu Pro Pro Asn Phe Val Gln Asn Ser Met Gln Leu
705                 710                 715                 720

Ser Arg Glu Glu Ile Gln Ser Ser Ile Ser Gly Val Thr Ala Ala Tyr
                725                 730                 735

Asn Arg Glu Gln Leu Trp Leu Ala Asn Glu Gly Leu Ile Thr Arg Leu
                740                 745                 750

Gln Ala Arg Cys Arg Gly Tyr Leu Val Arg Gln Glu Phe Arg Ser Arg
                755                 760                 765

Met Asn Phe Leu Lys Lys Gln Ile Pro Ala Ile Thr Cys Ile Gln Ser
        770                 775                 780

Gln Trp Arg Gly Tyr Lys Gln Lys Lys Ala Tyr Gln Asp Arg Leu Ala
785                 790                 795                 800

Tyr Leu Arg Ser His Lys Asp Glu Val Val Lys Ile Gln Ser Leu Ala
                805                 810                 815

Arg Met His Gln Ala Arg Lys Arg Tyr Arg Asp Arg Leu Gln Tyr Phe
                820                 825                 830

Arg Asp His Ile Asn Asp Ile Ile Lys Ile Gln Ala Phe Ile Arg Ala
                835                 840                 845

Asn Lys Ala Arg Asp Asp Tyr Lys Thr Leu Ile Asn Ala Glu Asp Pro
        850                 855                 860

Pro Met Val Val Val Arg Lys Phe Val His Leu Leu Asp Gln Ser Asp
865                 870                 875                 880

Gln Asp Phe Gln Glu Glu Leu Asp Leu Met Lys Met Arg Glu Glu Val
                885                 890                 895

Ile Thr Leu Ile Arg Ser Asn Gln Gln Leu Glu Asn Asp Leu Asn Leu
                900                 905                 910

Met Asp Ile Lys Ile Gly Leu Leu Val Lys Asn Lys Ile Thr Leu Gln
        915                 920                 925

Asp Val Val Ser His Ser Lys Lys Leu Thr Lys Lys Asn Lys Glu Gln
        930                 935                 940

Leu Ser Asp Met Met Met Ile Asn Lys Gln Lys Gly Gly Leu Lys Ala
945                 950                 955                 960

Leu Ser Lys Glu Lys Arg Glu Lys Leu Glu Ala Tyr Gln His Leu Phe
                965                 970                 975

Tyr Leu Leu Gln Thr Asn Pro Thr Tyr Leu Ala Lys Leu Ile Phe Gln
                980                 985                 990

Met Pro Gln Asn Lys Ser Thr Lys Phe Met Asp Ser Val Ile Phe Thr
        995                 1000                1005

Leu Tyr Asn Tyr Ala Ser Asn Gln Arg Glu Glu Tyr Leu Leu Leu
        1010                1015                1020

Arg Leu Phe Lys Thr Ala Leu Gln Glu Glu Ile Lys Ser Lys Val
        1025                1030                1035

Asp Gln Ile Gln Glu Ile Val Thr Gly Asn Pro Thr Val Ile Lys
        1040                1045                1050

Met Val Val Ser Phe Asn Arg Gly Ala Arg Gly Gln Asn Ala Leu
        1055                1060                1065

Arg Gln Ile Leu Ala Pro Val Val Lys Glu Ile Met Asp Asp Lys
        1070                1075                1080
```

-continued

| | | | | | | | | | | | | |
|---|---|---|---|---|---|---|---|---|---|---|---|---|
|Ser|Leu|Asn|Ile|Lys|Thr|Asp|Pro|Val|Asp|Ile|Tyr|Lys|Ser|Trp|
| |1085| | | |1090| | | |1095| | | |

Val Asn Gln Met Glu Ser Gln Thr Gly Glu Ala Ser Lys Leu Pro
     1100            1105            1110

Tyr Asp Val Thr Pro Glu Gln Ala Leu Ala His Glu Glu Val Lys
     1115            1120            1125

Thr Arg Leu Asp Ser Ser Ile Arg Asn Met Arg Ala Val Thr Asp
     1130            1135            1140

Lys Phe Leu Ser Ala Ile Val Ser Ser Val Asp Lys Ile Pro Tyr
     1145            1150            1155

Gly Met Arg Phe Ile Ala Lys Val Leu Lys Asp Ser Leu His Glu
     1160            1165            1170

Lys Phe Pro Asp Ala Gly Glu Asp Glu Leu Leu Lys Ile Ile Gly
     1175            1180            1185

Asn Leu Leu Tyr Tyr Arg Tyr Met Asn Pro Ala Ile Val Ala Pro
     1190            1195            1200

Asp Ala Phe Asp Ile Ile Asp Leu Ser Ala Gly Gly Gln Leu Thr
     1205            1210            1215

Thr Asp Gln Arg Arg Asn Leu Gly Ser Ile Ala Lys Met Leu Gln
     1220            1225            1230

His Ala Ala Ser Asn Lys Met Phe Leu Gly Asp Asn Ala His Leu
     1235            1240            1245

Ser Ile Ile Asn Glu Tyr Leu Ser Gln Ser Tyr Gln Lys Phe Arg
     1250            1255            1260

Arg Phe Phe Gln Thr Ala Cys Asp Val Pro Glu Leu Gln Asp Lys
     1265            1270            1275

Phe Asn Val Asp Glu Tyr Ser Asp Leu Val Thr Leu Thr Lys Pro
     1280            1285            1290

Val Ile Tyr Ile Ser Ile Gly Glu Ile Ile Asn Thr His Thr Leu
     1295            1300            1305

Leu Leu Asp His Gln Asp Ala Ile Ala Pro Glu His Asn Asp Pro
     1310            1315            1320

Ile His Glu Leu Leu Asp Asp Leu Gly Glu Val Pro Thr Ile Glu
     1325            1330            1335

Ser Leu Ile Gly Glu Ser Ser Gly Asn Leu Asn Asp Pro Asn Lys
     1340            1345            1350

Glu Ala Leu Ala Lys Thr Glu Val Ser Leu Thr Leu Thr Asn Lys
     1355            1360            1365

Phe Asp Val Pro Gly Asp Glu Asn Ala Glu Met Asp Ala Arg Thr
     1370            1375            1380

Ile Leu Leu Asn Thr Lys Arg Leu Ile Val Asp Val Ile Arg Phe
     1385            1390            1395

Gln Pro Gly Glu Thr Leu Thr Glu Ile Leu Glu Thr Pro Ala Thr
     1400            1405            1410

Ser Glu Gln Glu Ala Glu His Gln Arg Ala Met Gln Arg Arg Ala
     1415            1420            1425

Ile Arg Asp Ala Lys Thr Pro Asp Lys Met Lys Lys Ser Lys Ser
     1430            1435            1440

Val Lys Glu Asp Ser Asn Leu Thr Leu Gln Glu Lys Lys Glu Lys
     1445            1450            1455

Ile Gln Thr Gly Leu Lys Lys Leu Thr Glu Leu Gly Thr Val Asp
     1460            1465            1470

Pro Lys Asn Lys Tyr Gln Glu Leu Ile Asn Asp Ile Ala Arg Asp

```
                1475                1480                1485

Ile Arg Asn Gln Arg Arg Tyr Arg Gln Arg Arg Lys Ala Glu Leu
        1490                1495                1500

Val Lys Leu Gln Gln Thr Tyr Ala Ala Leu Asn Ser Lys Ala Thr
    1505                1510                1515

Phe Tyr Gly Glu Gln Val Asp Tyr Tyr Lys Ser Tyr Ile Lys Thr
    1520                1525                1530

Cys Leu Asp Asn Leu Ala Ser Lys Gly Lys Val Ser Lys Lys Pro
    1535                1540                1545

Arg Glu Met Lys Gly Lys Lys Ser Lys Lys Ile Ser Leu Lys Tyr
    1550                1555                1560

Thr Ala Ala Arg Leu His Glu Lys Gly Val Leu Leu Glu Ile Glu
    1565                1570                1575

Asp Leu Gln Val Asn Gln Phe Lys Asn Val Ile Phe Glu Ile Ser
    1580                1585                1590

Pro Thr Glu Glu Val Gly Asp Phe Glu Val Lys Ala Lys Phe Met
    1595                1600                1605

Gly Val Gln Met Glu Thr Phe Met Leu His Tyr Gln Asp Leu Leu
    1610                1615                1620

Gln Leu Gln Tyr Glu Gly Val Ala Val Met Lys Leu Phe Asp Arg
    1625                1630                1635

Ala Lys Val Asn Val Asn Leu Leu Ile Phe Leu Leu Asn Lys Lys
    1640                1645                1650

Phe Tyr Gly Lys
    1655

<210> SEQ ID NO 29
<211> LENGTH: 848
<212> TYPE: PRT
<213> ORGANISM: Homo sapiens

<400> SEQUENCE: 29

Met Asn Ser Ser Ser Ala Asn Ile Thr Tyr Ala Ser Arg Lys Arg Arg
1               5                   10                  15

Lys Pro Val Gln Lys Thr Val Lys Pro Ile Pro Ala Glu Gly Ile Lys
            20                  25                  30

Ser Asn Pro Ser Lys Arg His Arg Asp Arg Leu Asn Thr Glu Leu Asp
        35                  40                  45

Arg Leu Ala Ser Leu Leu Pro Phe Pro Gln Asp Val Ile Asn Lys Leu
    50                  55                  60

Asp Lys Leu Ser Val Leu Arg Leu Ser Val Ser Tyr Leu Arg Ala Lys
65                  70                  75                  80

Ser Phe Phe Asp Val Ala Leu Lys Ser Ser Pro Thr Glu Arg Asn Gly
                85                  90                  95

Gly Gln Asp Asn Cys Arg Ala Ala Asn Phe Arg Glu Gly Leu Asn Leu
            100                 105                 110

Gln Glu Gly Glu Phe Leu Leu Gln Ala Leu Asn Gly Phe Val Leu Val
        115                 120                 125

Val Thr Thr Asp Ala Leu Val Phe Tyr Ala Ser Ser Thr Ile Gln Asp
    130                 135                 140

Tyr Leu Gly Phe Gln Gln Ser Asp Val Ile His Gln Ser Val Tyr Glu
145                 150                 155                 160

Leu Ile His Thr Glu Asp Arg Ala Glu Phe Gln Arg Gln Leu His Trp
                165                 170                 175
```

```
Ala Leu Asn Pro Ser Gln Cys Thr Glu Ser Gly Gln Gly Ile Glu Glu
            180                 185                 190

Ala Thr Gly Leu Pro Gln Thr Val Val Cys Tyr Asn Pro Asp Gln Ile
        195                 200                 205

Pro Pro Glu Asn Ser Pro Leu Met Glu Arg Cys Phe Ile Cys Arg Leu
    210                 215                 220

Arg Cys Leu Leu Asp Asn Ser Ser Gly Phe Leu Ala Met Asn Phe Gln
225                 230                 235                 240

Gly Lys Leu Lys Tyr Leu His Gly Gln Lys Lys Gly Lys Asp Gly
                245                 250                 255

Ser Ile Leu Pro Pro Gln Leu Ala Leu Phe Ala Ile Ala Thr Pro Leu
            260                 265                 270

Gln Pro Pro Ser Ile Leu Glu Ile Arg Thr Lys Asn Phe Ile Phe Arg
        275                 280                 285

Thr Lys His Lys Leu Asp Phe Thr Pro Ile Gly Cys Asp Ala Lys Gly
    290                 295                 300

Arg Ile Val Leu Gly Tyr Thr Glu Ala Glu Leu Cys Thr Arg Gly Ser
305                 310                 315                 320

Gly Tyr Gln Phe Ile His Ala Ala Asp Met Leu Tyr Cys Ala Glu Ser
                325                 330                 335

His Ile Arg Met Ile Lys Thr Gly Glu Ser Gly Met Ile Val Phe Arg
            340                 345                 350

Leu Leu Thr Lys Asn Asn Arg Trp Thr Trp Val Gln Ser Asn Ala Arg
        355                 360                 365

Leu Leu Tyr Lys Asn Gly Arg Pro Asp Tyr Ile Ile Val Thr Gln Arg
    370                 375                 380

Pro Leu Thr Asp Glu Glu Gly Thr Glu His Leu Arg Lys Arg Asn Thr
385                 390                 395                 400

Lys Leu Pro Phe Met Phe Thr Thr Gly Glu Ala Val Leu Tyr Glu Ala
                405                 410                 415

Thr Asn Pro Phe Pro Ala Ile Met Asp Pro Leu Pro Leu Arg Thr Lys
            420                 425                 430

Asn Gly Thr Ser Gly Lys Asp Ser Ala Thr Thr Ser Thr Leu Ser Lys
        435                 440                 445

Asp Ser Leu Asn Pro Ser Ser Leu Leu Ala Ala Met Met Gln Gln Asp
    450                 455                 460

Glu Ser Ile Tyr Leu Tyr Pro Ala Ser Ser Thr Ser Ser Thr Ala Pro
465                 470                 475                 480

Phe Glu Asn Asn Phe Asn Glu Ser Met Asn Glu Cys Arg Asn Trp
                485                 490                 495

Gln Asp Asn Thr Ala Pro Met Gly Asn Asp Thr Ile Leu Lys His Glu
            500                 505                 510

Gln Ile Asp Gln Pro Gln Asp Val Asn Ser Phe Ala Gly Gly His Pro
        515                 520                 525

Gly Leu Phe Gln Asp Ser Lys Asn Ser Asp Leu Tyr Ser Ile Met Lys
    530                 535                 540

Asn Leu Gly Ile Asp Phe Glu Asp Ile Arg His Met Gln Asn Glu Lys
545                 550                 555                 560

Phe Phe Arg Asn Asp Phe Ser Gly Glu Val Asp Phe Arg Asp Ile Asp
                565                 570                 575

Leu Thr Asp Glu Ile Leu Thr Tyr Val Gln Asp Ser Leu Ser Lys Ser
            580                 585                 590

Pro Phe Ile Pro Ser Asp Tyr Gln Gln Gln Gln Ser Leu Ala Leu Asn
```

-continued

```
              595                 600                 605
Ser Ser Cys Met Val Gln Glu His Leu His Leu Glu Gln Gln Gln Gln
610                 615                 620

His His Gln Lys Gln Val Val Glu Pro Gln Gln Gln Leu Cys Gln
625                 630                 635                 640

Lys Met Lys His Met Gln Val Asn Gly Met Phe Glu Asn Trp Asn Ser
                645                 650                 655

Asn Gln Phe Val Pro Phe Asn Cys Pro Gln Gln Asp Pro Gln Gln Tyr
                660                 665                 670

Asn Val Phe Thr Asp Leu His Gly Ile Ser Gln Glu Phe Pro Tyr Lys
                675                 680                 685

Ser Glu Met Asp Ser Met Pro Tyr Thr Gln Asn Phe Ile Ser Cys Asn
690                 695                 700

Gln Pro Val Leu Pro Gln His Ser Lys Cys Thr Glu Leu Asp Tyr Pro
705                 710                 715                 720

Met Gly Ser Phe Glu Pro Ser Pro Tyr Pro Thr Thr Ser Ser Leu Glu
                725                 730                 735

Asp Phe Val Thr Cys Leu Gln Leu Pro Glu Asn Gln Lys His Gly Leu
                740                 745                 750

Asn Pro Gln Ser Ala Ile Ile Thr Pro Gln Thr Cys Tyr Ala Gly Ala
                755                 760                 765

Val Ser Met Tyr Gln Cys Gln Pro Glu Pro His Thr His Val Gly
770                 775                 780

Gln Met Gln Tyr Asn Pro Val Leu Pro Gly Gln Gln Ala Phe Leu Asn
785                 790                 795                 800

Lys Phe Gln Asn Gly Val Leu Asn Glu Thr Tyr Pro Ala Glu Leu Asn
                805                 810                 815

Asn Ile Asn Asn Thr Gln Thr Thr Thr His Leu Gln Pro Leu His His
                820                 825                 830

Pro Ser Glu Ala Arg Pro Phe Pro Asp Leu Thr Ser Ser Gly Phe Leu
                835                 840                 845
```

<210> SEQ ID NO 30
<211> LENGTH: 495
<212> TYPE: PRT
<213> ORGANISM: Mus musculus

<400> SEQUENCE: 30

```
Met Arg Thr Gln Ile Glu Val Ile Pro Cys Lys Ile Cys Gly Asp Lys
1               5                   10                  15

Ser Ser Gly Ile His Tyr Gly Val Ile Thr Cys Glu Gly Cys Lys Gly
                20                  25                  30

Phe Phe Arg Arg Ser Gln Gln Cys Asn Val Ala Tyr Ser Cys Thr Arg
            35                  40                  45

Gln Gln Asn Cys Pro Ile Asp Arg Thr Ser Arg Asn Arg Cys Gln His
        50                  55                  60

Cys Arg Leu Gln Lys Cys Leu Ala Leu Gly Met Ser Arg Asp Ala Val
65                  70                  75                  80

Lys Phe Gly Arg Met Ser Lys Lys Gln Arg Asp Ser Leu His Ala Glu
                85                  90                  95

Val Gln Lys Gln Leu Gln Gln Gln Gln Gln Glu Gln Val Ala Lys
                100                 105                 110

Thr Pro Pro Ala Gly Ser Arg Gly Ala Asp Thr Leu Thr Tyr Thr Leu
            115                 120                 125
```

```
Gly Leu Ser Asp Gly Gln Leu Pro Leu Gly Ala Ser Pro Asp Leu Pro
    130                 135                 140
Glu Ala Ser Ala Cys Pro Pro Gly Leu Leu Arg Ala Ser Gly Ser Gly
145                 150                 155                 160
Pro Pro Tyr Ser Asn Thr Leu Ala Lys Thr Glu Val Gln Gly Ala Ser
                165                 170                 175
Cys His Leu Glu Tyr Ser Pro Glu Arg Gly Lys Ala Glu Gly Arg Asp
            180                 185                 190
Ser Ile Tyr Ser Thr Asp Gly Gln Leu Thr Leu Gly Arg Cys Gly Leu
        195                 200                 205
Arg Phe Glu Glu Thr Arg His Pro Glu Leu Gly Glu Pro Gln Gly
    210                 215                 220
Pro Asp Ser His Cys Ile Pro Ser Phe Cys Ser Ala Pro Glu Val Pro
225                 230                 235                 240
Tyr Ala Ser Leu Thr Asp Ile Glu Tyr Leu Val Gln Asn Val Cys Lys
                245                 250                 255
Ser Phe Arg Glu Thr Cys Gln Leu Arg Leu Glu Asp Leu Leu Arg Gln
            260                 265                 270
Arg Thr Asn Leu Phe Ser Arg Glu Val Thr Ser Tyr Gln Arg Lys
    275                 280                 285
Ser Met Trp Glu Met Trp Glu Arg Cys Ala His His Leu Thr Glu Ala
290                 295                 300
Ile Gln Tyr Val Val Glu Phe Ala Lys Arg Leu Ser Gly Phe Met Glu
305                 310                 315                 320
Leu Cys Gln Asn Asp Gln Ile Ile Leu Leu Lys Ala Gly Ala Met Glu
                325                 330                 335
Val Val Leu Val Arg Met Cys Arg Ala Tyr Asn Ala Asn Asn His Thr
            340                 345                 350
Val Phe Phe Glu Gly Lys Tyr Gly Gly Val Glu Leu Phe Arg Ala Leu
        355                 360                 365
Gly Cys Ser Glu Leu Ile Ser Ser Ile Phe Asp Phe Ser His Phe Leu
    370                 375                 380
Ser Ala Leu Cys Phe Ser Glu Asp Glu Ile Ala Leu Tyr Thr Ala Leu
385                 390                 395                 400
Val Leu Ile Asn Ala Asn Arg Pro Gly Leu Gln Glu Lys Arg Arg Val
                405                 410                 415
Glu His Leu Gln Tyr Asn Leu Glu Leu Ala Phe His His His Leu Cys
            420                 425                 430
Lys Thr His Arg Gln Gly Leu Leu Ala Lys Leu Pro Pro Lys Gly Lys
    435                 440                 445
Leu Arg Ser Leu Cys Ser Gln His Val Glu Lys Leu Gln Ile Phe Gln
450                 455                 460
His Leu His Pro Ile Val Val Gln Ala Ala Phe Pro Pro Leu Tyr Lys
465                 470                 475                 480
Glu Leu Phe Ser Thr Asp Val Glu Ser Pro Glu Gly Leu Ser Lys
                485                 490                 495

<210> SEQ ID NO 31
<211> LENGTH: 1520
<212> TYPE: DNA
<213> ORGANISM: Mus musculus

<400> SEQUENCE: 31
atgggaaaag acctggcaat cagaggtgtg tgtgagcatt atcccaggga taatgccaag    60
```

```
ggtattatcc caagggtatc ccaagaagtg tcagaaaagc aaacatgatc caaacaggtg      120
aaagtcagag ttaccagcca gcaaaagacc tagaaagaag agcaaggtgt gaggtgctgc      180
aacttctgag aacacggtga tcatgaacag aatccagcaa tcctaccaga catgccatct      240
attgaacagg agctatcggt ccacctcatg ctgcatgtca gacaaaagct gaagagctgg      300
gacctaatga cccccatatt caccatcttg tcctcatatc tgctattcct gaagaaaaag      360
acttctcaaa gacataaagg caaaggtcat ctcatggaga ggagagaaca tgagagagct      420
gtttccatct tcccttctca tccctcatct cctcctgtta gtagtctcca cccggcagtg      480
cctcagtgtc tccactgtct ttcagccttc atcttgattt ctaattcttt cttcgattta      540
tccaatcagt cccttattct ttcacttcat ttccttcctc cttaaaagaa aggcttgata      600
ccgaacctca aaacagcaaa tattaacagg tttcttgata acatgcaacc gtaatgactt      660
cactagtaaa cctcatgtct ctcgctactc cttaataact aactagcctt tgtgattgtt      720
tcttgcagag aatagacatt caaggaaaaa cagttgcggt actcagttaa atagaacgtg      780
ttccgttggt gttaaattat ttatttttgta tgtctgttta catactaaga cattgagtgg      840
gtttctttgg gcaagggatg ctctctagcc agggaatttg gtagaaaagt gagaaagatc      900
aagtcaaaat tcaaagtgtg tgtcactagg agactgtcaa gagactcaca aaccattact      960
atggagccca gctctgcagc agcttcagat atgtccatac acacatgata ctgaatcaca     1020
gcaaagcatc tctgttcagc tcccaagaag tcatgcttct ttgcatagtg aacttctgcc     1080
cttcccatct accttcgaga cagatgttgc ccgtcataaa ggggtggttc tgtgctgacc     1140
tcatttgagg atggaatctt tactcaaatg tgtgtcacccc ccaacccact cttgacgtaa     1200
gtgaccacag aggtagtaaa accgtataaa aagagagaaa ggagcactac tcttcatcca     1260
cctcacacga ggcacaagtg cacccagcac cagctgatca ggacgcgcaa acatgagtcc     1320
agggagagct tcatctgtgg tgagtcctgc actaatgtac aaggcgcttg ttgattgtga     1380
ccaggttgcg ttattgcacg tgatatgaaa tgctctattc cagctgttgg ggtccatgaa     1440
tctgtacatg tagaactgga aatgaaacct ttggtagatg tcgaaatcat tgtacagcat     1500
tttcaagaac tgataggcat                                                 1520
```

<210> SEQ ID NO 32
<211> LENGTH: 15
<212> TYPE: PRT
<213> ORGANISM: Homo sapiens

<400> SEQUENCE: 32

```
Asn Thr Val Trp Lys Gln Leu Ser Ser Ser Val Thr Gly Leu Thr
1               5                   10                  15
```